US012612455B2

(12) United States Patent
Bergeron et al.

(10) Patent No.: US 12,612,455 B2
(45) Date of Patent: Apr. 28, 2026

(54) FELINE ANTIBODY VARIANTS

(71) Applicant: Zoetis Services LLC, Parsippany, NJ (US)

(72) Inventors: Lisa Marie Bergeron, Boulder, CO (US); Henry Luis Campos, Kalamazoo, MI (US)

(73) Assignee: Zoetis Services LLC, Parsippany, NJ (US)

( * ) Notice: Subject to any disclaimer, the term of this patent is extended or adjusted under 35 U.S.C. 154(b) by 447 days.

(21) Appl. No.: 18/246,725

(22) PCT Filed: Sep. 29, 2021

(86) PCT No.: PCT/US2021/052579
§ 371 (c)(1),
(2) Date: Mar. 27, 2023

(87) PCT Pub. No.: WO2022/072446
PCT Pub. Date: Apr. 7, 2022

(65) Prior Publication Data
US 2023/0382986 A1      Nov. 30, 2023

Related U.S. Application Data

(60) Provisional application No. 63/084,693, filed on Sep. 29, 2020.

(51) Int. Cl.
*C07K 16/22* (2006.01)
*C07K 16/00* (2006.01)
*C07K 16/18* (2006.01)

(52) U.S. Cl.
CPC .............. *C07K 16/22* (2013.01); *C07K 16/00* (2013.01); *C07K 16/18* (2013.01); *C07K 2317/20* (2013.01); *C07K 2317/52* (2013.01); *C07K 2317/524* (2013.01); *C07K 2317/526* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 4,946,778 A | 8/1990 | Ladner et al. | |
| 5,225,539 A | 7/1993 | Winter | |
| 5,585,089 A | 12/1996 | Queen et al. | |
| 5,698,762 A | 12/1997 | Dauerman | |
| 5,807,715 A | 9/1998 | Morrison et al. | |
| 6,284,471 B1 | 9/2001 | Le et al. | |
| 8,012,482 B2 | 9/2011 | Adams et al. | |
| 8,088,376 B2 | 1/2012 | Chamberlain et al. | |
| 8,394,925 B2 | 3/2013 | Chamberlain et al. | |
| 8,546,543 B2 | 10/2013 | Lazar | |
| 8,790,651 B2 | 7/2014 | Bammert et al. | |
| 9,206,253 B2 | 12/2015 | Bammert et al. | |
| 9,505,829 B2 | 11/2016 | Lacy et al. | |
| 9,617,334 B2 | 4/2017 | Bergeron et al. | |
| 9,803,023 B2 | 10/2017 | Chamberlain et al. | |
| 9,951,128 B2 | 4/2018 | Bergeron et al. | |
| 10,093,725 B2 | 10/2018 | Lacy et al. | |
| 10,125,192 B2 | 11/2018 | Lacy et al. | |
| 10,336,818 B2 | 7/2019 | Chamberlain et al. | |
| 10,421,807 B2 | 9/2019 | Gonzales et al. | |
| 10,526,405 B2 | 1/2020 | Mann et al. | |
| 2003/0031671 A1 | 2/2003 | Welt et al. | |
| 2006/0067930 A1 | 3/2006 | Adams et al. | |
| 2022/0048981 A1 | 2/2022 | Nakao et al. | |

FOREIGN PATENT DOCUMENTS

| | | |
|---|---|---|
| WO | 1986001533 A1 | 3/1986 |
| WO | 2019113123 A1 | 6/2019 |
| WO | 2020082048 A1 | 4/2020 |
| WO | 2021212084 A1 | 10/2021 |
| WO | 2022072446 A1 | 4/2022 |
| WO | 2022133252 A1 | 6/2022 |

OTHER PUBLICATIONS

Bird R.E., et al., Science, 1988, vol. 240, pp. 423-426.
Bowie J.U., et al., "Deciphering the Message in Protein Sequences: Tolerance to Amino Acid Substitutions," Science, 1990, vol. 247, pp. 1306-1310.
Buhren J., et al., "Optical Effects of Anti-TGFBeta Treatment after Photorefractive Keratectomy in a Cat Model," Investigative Ophthalmology and Visual Science, Feb. 1, 2009, vol. 50, No. 2, pp. 634-643, doi: 10.1167/iovs. 08-2277, XP055858622.
Burmeister W.P., et al., "Crystal Structure of the Complex of Rat Neonatal Fc Receptor with Fc", Letters Of Nature, Nov. 24, 1994, vol. 372, No. 6504, pp. 379-383, doi: 10.1038/372379a0.
Cunningham B.C., et al., "High-Resolution Epitope Mapping of hGH-Receptor Interactions by Alanine-Scanning Mutagenesis", Science, Jun. 2, 1989, vol. 244, pp. 1081-1085.
De Vos A.M., et al., "Human Growth Hormone and Extracellular Domain of Its Receptor: Crystal Structure of the Complex", Science, 1992, vol. 255, pp. 306-312.
Ellman, et al., Methods in Enzymology, 1991, vol. 202, pp. 301-336.
Gorman M.C., et al., "The Rous Sarcoma Virus Long Terminal Repeat is a Strong Promoter When Introduced into a Variety of Eukaryotic cells by DNA-mediated Transfection", Proceedings of the National Academy of Sciences, USA, 1982, vol. 79, pp. 6777-6781.
Grosschedi R., et al., "Cell-Type Specificity of Immunoglobulin Gene Expression is Regulated by at Least Three DNA Sequence Elements," Cell, Jul. 1985, vol. 41, pp. 885-897(13 Pages).

(Continued)

*Primary Examiner* — Nora M Rooney
(74) *Attorney, Agent, or Firm* — Prakash Subbiah

(57) ABSTRACT

The invention relates generally to feline antibody variants and uses thereof. Specifically, the invention relates to mutations in the constant region of feline antibody for improving its half-life and other characters.

15 Claims, 22 Drawing Sheets
Specification includes a Sequence Listing.

(56)　　　　　References Cited

OTHER PUBLICATIONS

Guyer R.L., et al., "Immunoglobulin Binding by Mouse Intestinal Epithelial Cell Receptors", Journal of Immunology, vol. 117, No. 2, 1976, pp. 587-593.

International Preliminary Report on Patentability for International Application No. PCT/US2021/052579, dated Apr. 13, 2023, 11 Pages.

International Search Report and Written Opinion for International Application No. PCT/US2021/052579, dated Mar. 15, 2022, 18 Pages.

Izaki, Japanese Journal of Bacteriology, 1978, vol. 33, pp. 729-742.

John J.F., et al., "Plasmids as Epidemiologic Markers in Nosocomial Gram-Negative Bacilli: Experience at a University and Review of the Literature", Reviews of Infectious Diseases, 1986, vol. 8, No. 5, pp. 693-704.

Kendall, et al., Journal of Bacteriology, 1987, vol. 169, pp. 4177-4183.

Kim J-K., et al., "Localization of the Site of the Murine IgG1 Molecule that is Involved in Binding to the Murine Intestinal Fc Receptor," The European Journal of Immunology, 1994, vol. 24, pp. 2429-2434.

Lathe R., "Synthetic Oligonucleotide Probes Deduced from Amino Acid Sequence Data: Theoretical and Practical Considerations", Journal of Molecular Biology, vol. 183, 1985, pp. 1-12.

Lawson U.S., et al., "Characterisation of Feline Renal Cortical Fibroblast Cultures and Their Transcriptional Response to Transforming Growth Factor Beta1", BMC Veterinary Research, Mar. 9, 2018, vol. 14, No. 1, 76, Retrieved from https://doi.org/10.1186/s12917-018-1387-2, 11 Pages.

Lawson U.S., et al., "The Cat as a Naturally Occurring Model of Renal Interstitial Fibrosis: Characterisation of Primary Feline Proximal Tubular Epithelial Cells and Comparative Pro-Fibrotic Effects of TGF-[beta]1," Plos One, Aug. 23, 2018, vol. 13, No. 8, e0202577, pp. 1-24, DOI: 10.1371/journal.pone.0202577, XP055840441.

Newman R., et al., Biotechnology, 1993, vol. 10, pp. 1455-1460.

Oganesyan V., et al., "Structural Insights into Neonatal Fc Receptor-based Recycling Mechanisms", Journal of Biological Chemistry, Mar. 14, 2014, vol. 289, No. 11, pp. 7812-7824, doi:10.1074/jbc.M113.537563.

Okayama H., et al., "A cDNA Cloning Vector That Permits Expression of cDNA Inserts in Mammalian Cells", Molecular and Cellular Biology, Feb. 1983, vol. 3, No. 2, pp. 280-312.

Pearson W.R., et al., "Improved Tools for Biological Sequence Comparison", Proceedings of the National Academy of Sciences of the United States of America, Apr. 1988, vol. 85, pp. 2444-2448.

Perez J.M., et al., "Critical Approach to the Alternative Treatment of Chronic Kidney Disease in Dogs and Cats", Slovenian Veterinary Research, Jul. 23, 2018, vol. 55, No. 2, pp. 59-71, DOI: 10.26873/SVR-273-2017, ISSN 1580-4003, XP055859441, 14 Pages.

Pluckthunkerra , Methods in Enzymology, 1989, vol. 178, pp. 497-515.

Rattan S.I., et al., "Protein Synthesis, Posttranslational Modifications, and Aging", Annals of the New York Academy of Sciences, 1992, vol. 663, pp. 48-62.

Saxena A., et al., "Advances in Therapeutic Fc Engineering - Modulation of IgG-Associated Effector Functions and Serum Half-life", Frontiers Immunology, Dec. 12, 2016, Sec. Vaccines and Molecular Therapeutics, vol. 7, Retrieved from https://doi.org/10.3389/fimmu.2016.00580, pp. 1-11.

Seifter S., et al., "Analysis for Protein Modifications and Nonprotein Cofactors", Methods in Enzymology, 1990, vol. 182, pp. 626-646.

Shields R.L., et al., "High Resolution Mapping of the Binding Site on Human IgG1 for Fc Gamma RI, Fc Gamma RII, Fc Gamma RIII, and FcRn and Design of IgG1 Variants with Improved Binding to the Fc Gamma R", Journal of Biological Chemistry, Mar. 2, 2001, vol. 276, No. 9, pp. 6591-6604, doi:10.1074/jbc.M009483200.

Smith L.J., et al., "Human Interlukin 4 The Solution Structure of a Four-Helix Bundle Protein", Journal of Molecular Biology, 1992, vol. 224, pp. 899-904.

Strietzel C.J., et al., "In Vitro Functional Characterization of Feline IgGs", Veterinary Immunology and Immunopathology, Apr. 15, 2014, vol. 158, No. 3, pp. 214-223, Retrieved from http://dx.doi.org/10.1016/j.vetimm.2014.01.012, See figure 4.

"TGF-beta 1, 2, 3 Antibody", Catalog #MAB1835, Monoclonal Mouse IgG1 Clone #1D11, R&D Systems, Retrieved from https://www.rndsystems.com/products/tgf-beta1-2-3-antibody-1d11_mab1835.

Weidle U.H., et al., "Reconstitution of Functionally Active Antibody Directed Against Creatine Kinase from Separately Expressed Heavy and Light Chains in Non-lymphoid Cells", Gene, 1987, vol. 51, pp. 21-29.

Whittle, et al., Protein Engineering, 1987, vol. 1, p. 499.

>Human IgG1_EU Index

| 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 |
|---|---|---|---|---|---|---|---|---|---|---|---|---|---|---|---|---|---|---|---|---|---|---|---|---|---|---|---|---|---|---|
| A | S | T | K | G | P | S | V | F | P | L | A | P | S | S | K | S | T | S | G | G | T | A | A | L | G | C | L | V | K | D |

(1)

>Feline IgG1a_EU Index

| 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 |
|---|---|---|---|---|---|---|---|---|---|---|---|---|---|---|---|---|---|---|---|---|---|---|---|---|---|---|---|---|---|---|
| A | S | T | A | P | S | V | F | P | L | A | P | S | C | G | T | T | S | G | A | T | V | A | L | A | C | L | V | L | G |

>Feline IgG1b_EU Index

| 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 |
|---|---|---|---|---|---|---|---|---|---|---|---|---|---|---|---|---|---|---|---|---|---|---|---|---|---|---|---|---|---|---|
| A | S | T | A | P | S | V | F | P | L | A | P | S | C | G | T | T | S | G | A | T | V | A | L | A | C | L | V | L | G |

>Feline IgG2_EU Index

| 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 |
|---|---|---|---|---|---|---|---|---|---|---|---|---|---|---|---|---|---|---|---|---|---|---|---|---|---|---|---|---|---|---|
| A | S | T | A | S | S | V | F | P | L | A | P | S | C | G | T | T | S | G | A | T | V | A | L | A | C | L | V | L | G |

>Feline IgG2_Hinge mut_EU Index

| 118 | 119 | 120 | 121 | 122 | 123 | 124 | 125 | 126 | 127 | 128 | 129 | 130 | 131 | 132 | 133 | 134 | 135 | 136 | 137 | 138 | 139 | 140 | 141 | 142 | 143 | 144 | 145 | 146 | 147 | 148 |
|---|---|---|---|---|---|---|---|---|---|---|---|---|---|---|---|---|---|---|---|---|---|---|---|---|---|---|---|---|---|---|
| A | S | T | A | S | S | V | F | P | L | A | P | S | C | G | T | T | S | G | A | T | V | A | L | A | C | L | V | L | G |

FIGURE 2A

>Human IgG1_EU Index

| 149 | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 | 179 |
|---|---|---|---|---|---|---|---|---|---|---|---|---|---|---|---|---|---|---|---|---|---|---|---|---|---|---|---|---|---|---|
| Y | F | P | E | P | V | T | V | S | W | N | S | G | A | L | T | S | G | V | H | T | F | P | A | V | L | Q | S | S | G | L |

2

>Feline IgG1a_EU Index

| 149 | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 | 179 |
|---|---|---|---|---|---|---|---|---|---|---|---|---|---|---|---|---|---|---|---|---|---|---|---|---|---|---|---|---|---|---|
| Y | F | P | E | P | V | T | V | S | W | N | S | G | A | L | T | S | G | V | H | T | F | P | A | V | L | Q | A | S | G | L |

>Feline IgG1b_EU Index

| 149 | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 | 179 |
|---|---|---|---|---|---|---|---|---|---|---|---|---|---|---|---|---|---|---|---|---|---|---|---|---|---|---|---|---|---|---|
| Y | F | P | E | P | V | T | V | S | W | N | S | G | A | L | T | S | G | V | H | T | F | P | A | V | L | Q | A | S | G | L |

>Feline IgG2_EU Index

| 149 | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 | 179 |
|---|---|---|---|---|---|---|---|---|---|---|---|---|---|---|---|---|---|---|---|---|---|---|---|---|---|---|---|---|---|---|
| Y | F | P | E | P | V | T | V | S | W | N | S | G | A | L | T | S | G | V | H | T | F | P | S | V | L | Q | A | S | G | L |

>Feline IgG2_Hinge mut_EU Index

| 149 | 150 | 151 | 152 | 153 | 154 | 155 | 156 | 157 | 158 | 159 | 160 | 161 | 162 | 163 | 164 | 165 | 166 | 167 | 168 | 169 | 170 | 171 | 172 | 173 | 174 | 175 | 176 | 177 | 178 | 179 |
|---|---|---|---|---|---|---|---|---|---|---|---|---|---|---|---|---|---|---|---|---|---|---|---|---|---|---|---|---|---|---|
| Y | F | P | E | P | V | T | V | S | W | N | S | G | A | L | T | S | G | V | H | T | F | P | S | V | L | Q | A | S | G | L |

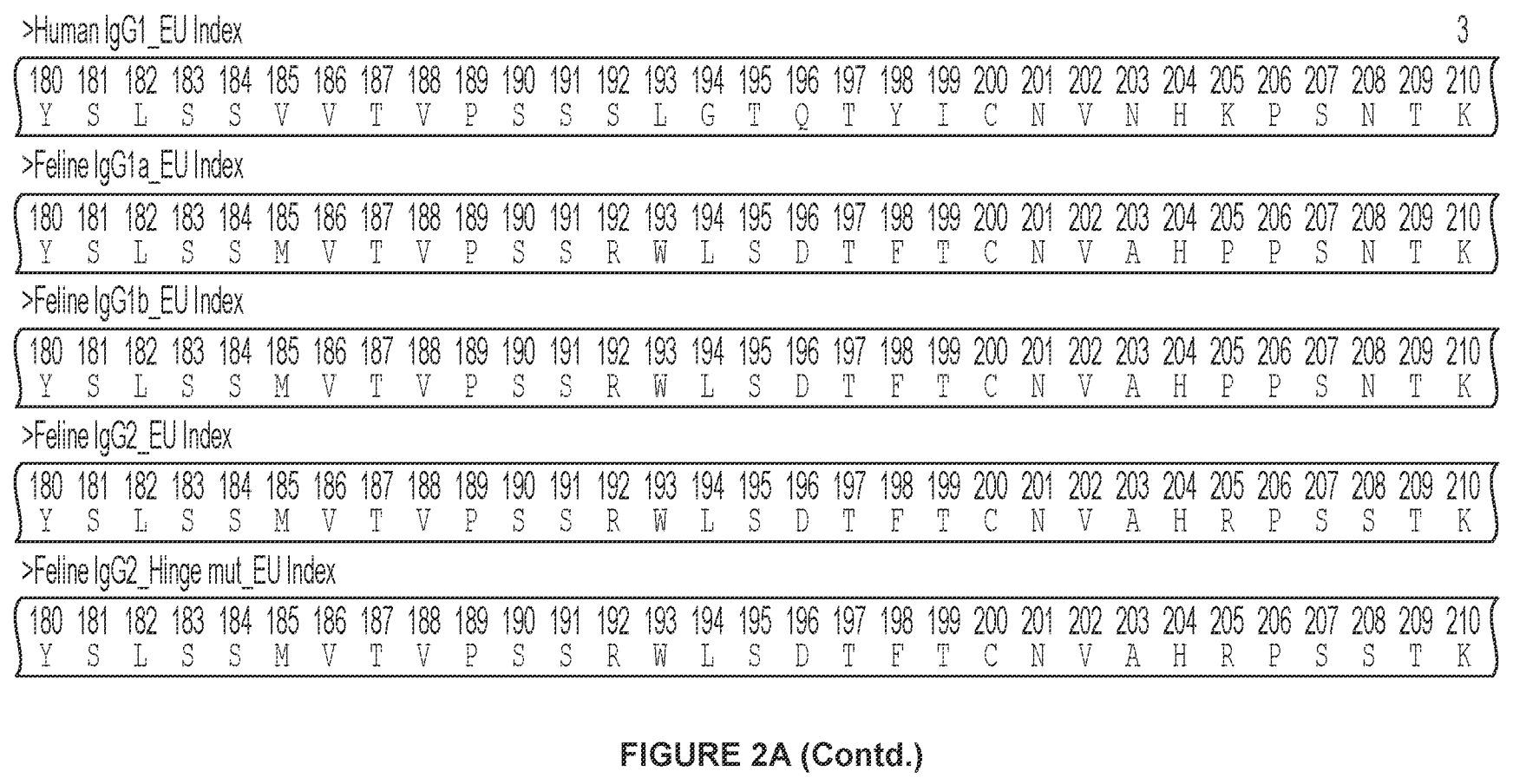

>Human IgG1_EU Index

| 180 | 181 | 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 | 207 | 208 | 209 | 210 |
|---|---|---|---|---|---|---|---|---|---|---|---|---|---|---|---|---|---|---|---|---|---|---|---|---|---|---|---|---|---|---|
| Y | S | L | S | S | V | V | T | V | P | S | S | S | L | G | T | Q | T | Y | I | C | N | V | N | H | K | P | S | N | T | K |

>Feline IgG1a_EU Index

| 180 | 181 | 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 | 207 | 208 | 209 | 210 |
|---|---|---|---|---|---|---|---|---|---|---|---|---|---|---|---|---|---|---|---|---|---|---|---|---|---|---|---|---|---|---|
| Y | S | L | S | S | M | V | T | V | P | S | S | R | W | L | S | D | T | F | I | C | N | V | A | H | P | P | S | N | T | K |

>Feline IgG1b_EU Index

| 180 | 181 | 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 | 207 | 208 | 209 | 210 |
|---|---|---|---|---|---|---|---|---|---|---|---|---|---|---|---|---|---|---|---|---|---|---|---|---|---|---|---|---|---|---|
| Y | S | L | S | S | M | V | T | V | P | S | S | R | W | L | S | D | T | F | I | C | N | V | A | H | P | P | S | N | T | K |

>Feline IgG2_EU Index

| 180 | 181 | 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 | 207 | 208 | 209 | 210 |
|---|---|---|---|---|---|---|---|---|---|---|---|---|---|---|---|---|---|---|---|---|---|---|---|---|---|---|---|---|---|---|
| Y | S | L | S | S | M | V | T | V | P | S | S | R | W | L | S | D | T | F | I | C | N | V | A | H | R | P | S | S | T | K |

>Feline IgG2_Hinge mut_EU Index

| 180 | 181 | 182 | 183 | 184 | 185 | 186 | 187 | 188 | 189 | 190 | 191 | 192 | 193 | 194 | 195 | 196 | 197 | 198 | 199 | 200 | 201 | 202 | 203 | 204 | 205 | 206 | 207 | 208 | 209 | 210 |
|---|---|---|---|---|---|---|---|---|---|---|---|---|---|---|---|---|---|---|---|---|---|---|---|---|---|---|---|---|---|---|
| Y | S | L | S | S | M | V | T | V | P | S | S | R | W | L | S | D | T | F | I | C | N | V | A | H | R | P | S | S | T | K |

FIGURE 2A (Contd.)

Figure 2A:
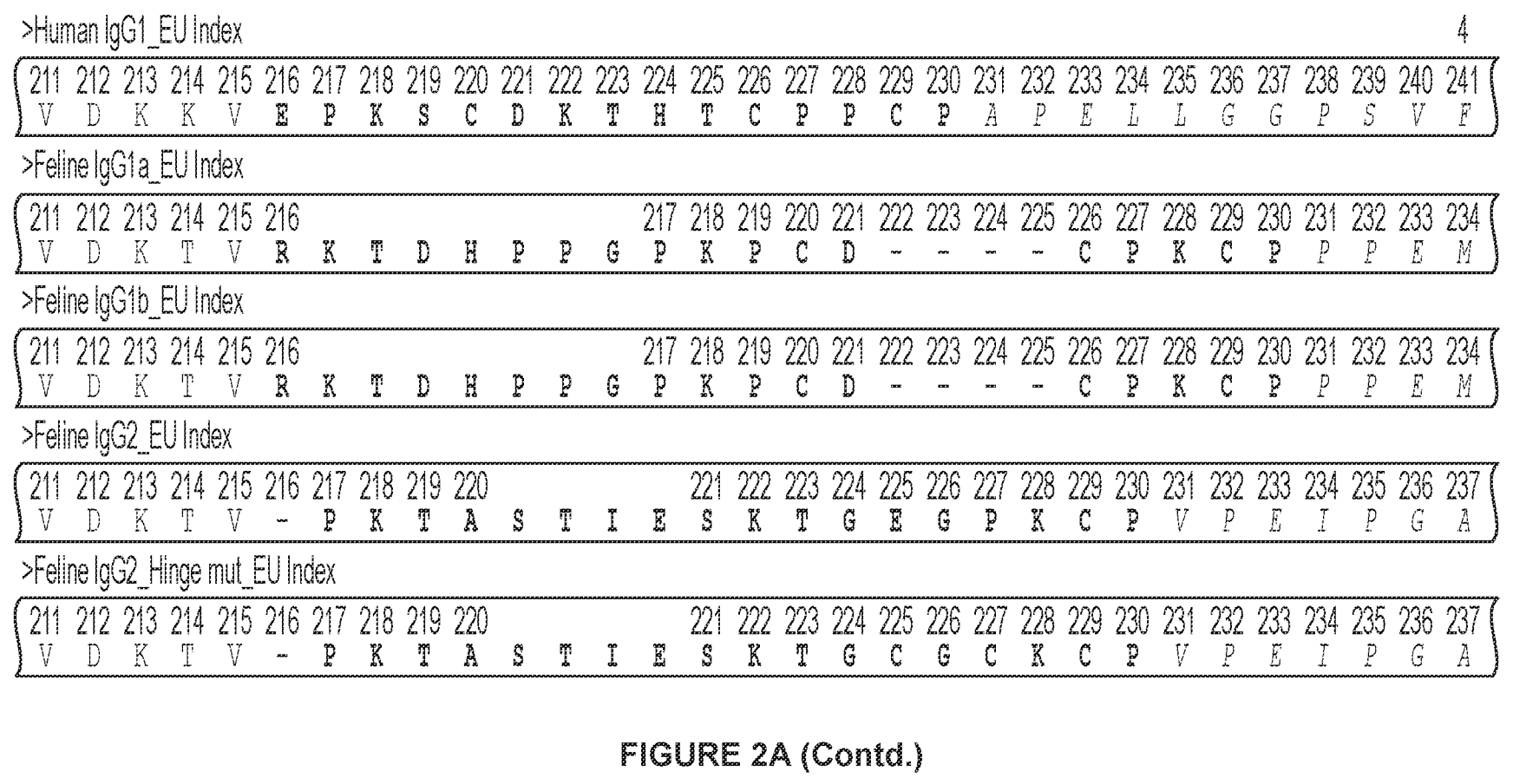

>Human IgG1_EU Index

| 211 | 212 | 213 | 214 | 215 | 216 | 217 | 218 | 219 | 220 | 221 | 222 | 223 | 224 | 225 | 226 | 227 | 228 | 229 | 230 | 231 | 232 | 233 | 234 | 235 | 236 | 237 | 238 | 239 | 240 | 241 |
|---|---|---|---|---|---|---|---|---|---|---|---|---|---|---|---|---|---|---|---|---|---|---|---|---|---|---|---|---|---|---|
| V | D | K | K | V | E | P | K | S | C | D | K | T | H | T | C | P | P | C | P | A | P | E | L | L | G | G | P | S | V | F |

4

>Feline IgG1a_EU Index

| 211 | 212 | 213 | 214 | 215 | 216 | 217 | 218 | 219 | 220 | 221 | 222 | 223 | 224 | 225 | 226 | 227 | 228 | 229 | 230 | 231 | 232 | 233 | 234 |
|---|---|---|---|---|---|---|---|---|---|---|---|---|---|---|---|---|---|---|---|---|---|---|---|
| V | D | K | T | V | R | K | T | D | H | P | P | G | P | K | P | C | – | – | C | P | P | E | M |

>Feline IgG1b_EU Index

| 211 | 212 | 213 | 214 | 215 | 216 | 217 | 218 | 219 | 220 | 221 | 222 | 223 | 224 | 225 | 226 | 227 | 228 | 229 | 230 | 231 | 232 | 233 | 234 |
|---|---|---|---|---|---|---|---|---|---|---|---|---|---|---|---|---|---|---|---|---|---|---|---|
| V | D | K | T | V | R | K | T | D | H | P | P | G | P | K | P | C | – | – | C | P | P | E | M |

>Feline IgG2_EU Index

| 211 | 212 | 213 | 214 | 215 | 216 | 217 | 218 | 219 | 220 | 221 | 222 | 223 | 224 | 225 | 226 | 227 | 228 | 229 | 230 | 231 | 232 | 233 | 234 | 235 | 236 | 237 |
|---|---|---|---|---|---|---|---|---|---|---|---|---|---|---|---|---|---|---|---|---|---|---|---|---|---|---|
| V | D | K | T | V | – | P | K | T | A | S | T | I | E | S | K | T | G | G | P | K | C | P | V | P | E | I | P | G | A |

>Feline IgG2_Hinge mut_EU Index

| 211 | 212 | 213 | 214 | 215 | 216 | 217 | 218 | 219 | 220 | 221 | 222 | 223 | 224 | 225 | 226 | 227 | 228 | 229 | 230 | 231 | 232 | 233 | 234 | 235 | 236 | 237 |
|---|---|---|---|---|---|---|---|---|---|---|---|---|---|---|---|---|---|---|---|---|---|---|---|---|---|---|
| V | D | K | T | V | – | P | K | T | A | S | T | I | E | S | K | T | G | C | K | C | P | V | P | E | I | P | G | A |

>Human IgG1_EU Index

| 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 | 266 | 267 | 268 | 269 | 270 | 271 | 272 |
|---|---|---|---|---|---|---|---|---|---|---|---|---|---|---|---|---|---|---|---|---|---|---|---|---|---|---|---|---|---|---|
| L | F | P | P | K | P | K | D | T | L | M | I | S | R | T | P | E | V | T | C | V | V | V | D | V | S | H | E | D | P | E |

>Feline IgG1a_EU Index

| 235 | 236 | 237 | 238 | 239 | 240 | 241 | 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 |
|---|---|---|---|---|---|---|---|---|---|---|---|---|---|---|---|---|---|---|---|---|---|---|---|---|---|---|---|---|---|---|
| L | G | P | S | I | F | I | F | P | P | K | P | K | D | T | L | S | I | S | R | T | P | E | V | T | C | L | V | V | D |

>Feline IgG1b_EU Index

| 235 | 236 | 237 | 238 | 239 | 240 | 241 | 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 |
|---|---|---|---|---|---|---|---|---|---|---|---|---|---|---|---|---|---|---|---|---|---|---|---|---|---|---|---|---|---|---|---|
| L | G | P | S | I | F | I | F | P | P | K | P | K | D | T | L | S | I | S | R | T | P | E | V | T | C | L | V | V | D |

>Feline IgG2_EU Index

| 238 | 239 | 240 | 241 | 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 | 266 | 267 | 268 |
|---|---|---|---|---|---|---|---|---|---|---|---|---|---|---|---|---|---|---|---|---|---|---|---|---|---|---|---|---|---|---|---|
| P | S | V | F | I | F | P | P | K | P | K | D | T | L | S | I | S | R | T | P | E | V | T | C | L | V | V | D | L | G | P |

>Feline IgG2_Hinge mut_EU index

| 238 | 239 | 240 | 241 | 242 | 243 | 244 | 245 | 246 | 247 | 248 | 249 | 250 | 251 | 252 | 253 | 254 | 255 | 256 | 257 | 258 | 259 | 260 | 261 | 262 | 263 | 264 | 265 | 266 | 267 | 268 |
|---|---|---|---|---|---|---|---|---|---|---|---|---|---|---|---|---|---|---|---|---|---|---|---|---|---|---|---|---|---|---|---|
| P | S | V | F | I | F | P | P | K | P | K | D | T | L | S | I | S | R | T | P | E | V | T | C | L | V | V | D | L | G | P |

FIGURE 2A (Contd.)

>Human IgG1_EU Index

| 273 | 274 | 275 | 276 | 277 | 278 | 279 | 280 | 281 | 282 | 283 | 284 | 285 | 286 | 287 | 288 | 289 | 290 | 291 | 292 | 293 | 294 | 295 | 296 | 297 | 298 | 299 | 300 | 301 | 302 | 303 |
|---|---|---|---|---|---|---|---|---|---|---|---|---|---|---|---|---|---|---|---|---|---|---|---|---|---|---|---|---|---|---|
| V | K | F | N | W | Y | V | D | G | V | E | V | H | N | A | K | T | K | P | R | E | E | Q | Y | N | S | T | Y | R | V | V |

>Feline IgG1a_EU Index

| 266 | 267 | 268 | 269 | 270 | 271 | 272 | 273 | 274 | 275 | 276 | 277 | 278 | 279 | 280 | 281 | 282 | 283 | 284 | 285 | 286 | 287 | 288 | 289 | 290 | 291 | 292 | 293 | 294 | 295 | 296 |
|---|---|---|---|---|---|---|---|---|---|---|---|---|---|---|---|---|---|---|---|---|---|---|---|---|---|---|---|---|---|---|
| L | G | P | D | D | S | D | V | Q | I | T | W | F | V | D | N | T | Q | V | Y | T | A | K | T | S | P | R | E | E | Q | F |

>Feline IgG1b_EU Index

| 266 | 267 | 268 | 269 | 270 | 271 | 272 | 273 | 274 | 275 | 276 | 277 | 278 | 279 | 280 | 281 | 282 | 283 | 284 | 285 | 286 | 287 | 288 | 289 | 290 | 291 | 292 | 293 | 294 | 295 | 296 |
|---|---|---|---|---|---|---|---|---|---|---|---|---|---|---|---|---|---|---|---|---|---|---|---|---|---|---|---|---|---|---|---|
| L | G | P | D | S | D | V | Q | I | T | W | F | V | D | N | T | Q | V | Y | T | A | K | T | S | P | R | E | E | Q | F | |

>Feline IgG2_EU Index

| 269 | 270 | 271 | 272 | 273 | 274 | 275 | 276 | 277 | 278 | 279 | 280 | 281 | 282 | 283 | 284 | 285 | 286 | 287 | 288 | 289 | 290 | 291 | 292 | 293 | 294 | 295 | 296 | 297 | 298 | 299 |
|---|---|---|---|---|---|---|---|---|---|---|---|---|---|---|---|---|---|---|---|---|---|---|---|---|---|---|---|---|---|---|---|
| D | D | S | N | V | Q | I | T | W | F | V | D | N | T | E | M | H | T | A | K | T | R | P | R | E | E | Q | F | N | S | T |

>Feline IgG2_Hinge mut_EU Index

| 269 | 270 | 271 | 272 | 273 | 274 | 275 | 276 | 277 | 278 | 279 | 280 | 281 | 282 | 283 | 284 | 285 | 286 | 287 | 288 | 289 | 290 | 291 | 292 | 293 | 294 | 295 | 296 | 297 | 298 | 299 |
|---|---|---|---|---|---|---|---|---|---|---|---|---|---|---|---|---|---|---|---|---|---|---|---|---|---|---|---|---|---|---|---|
| D | D | S | N | V | Q | I | T | W | F | V | D | N | T | E | M | H | T | A | K | T | R | P | R | E | E | Q | F | N | S | T |

FIGURE 2A (Contd.)

>Human IgG1_EU Index

| 304 | 305 | 306 | 307 | 308 | 309 | 310 | 311 | 312 | 313 | 314 | 315 | 316 | 317 | 318 | 319 | 320 | 321 | 322 | 323 | 324 | 325 | 326 | 327 | 328 | 329 | 330 | 331 | 332 | 333 | 334 |
|---|---|---|---|---|---|---|---|---|---|---|---|---|---|---|---|---|---|---|---|---|---|---|---|---|---|---|---|---|---|---|
| S | V | L | T | V | L | H | Q | D | W | L | N | G | K | E | Y | K | C | K | V | S | N | K | A | L | P | A | P | I | E | K |

>Feline IgG1a_EU Index

| 297 | 298 | 299 | 300 | 301 | 302 | 303 | 304 | 305 | 306 | 307 | 308 | 309 | 310 | 311 | 312 | 313 | 314 | 315 | 316 | 317 | 318 | 319 | 320 | 321 | 322 | 323 | 324 | 325 | 326 | 327 |
|---|---|---|---|---|---|---|---|---|---|---|---|---|---|---|---|---|---|---|---|---|---|---|---|---|---|---|---|---|---|---|
| N | S | T | Y | R | V | V | S | V | L | P | I | L | H | Q | D | W | L | K | G | K | E | F | K | C | K | V | N | S | K | S |

>Feline IgG1b_EU Index

| 297 | 298 | 299 | 300 | 301 | 302 | 303 | 304 | 305 | 306 | 307 | 308 | 309 | 310 | 311 | 312 | 313 | 314 | 315 | 316 | 317 | 318 | 319 | 320 | 321 | 322 | 323 | 324 | 325 | 326 | 327 |
|---|---|---|---|---|---|---|---|---|---|---|---|---|---|---|---|---|---|---|---|---|---|---|---|---|---|---|---|---|---|---|---|
| N | S | T | Y | R | V | V | S | V | L | P | I | L | H | Q | D | W | L | K | G | K | E | F | K | C | K | V | N | S | K | S |

>Feline IgG2_EU Index

| 300 | 301 | 302 | 303 | 304 | 305 | 306 | 307 | 308 | 309 | 310 | 311 | 312 | 313 | 314 | 315 | 316 | 317 | 318 | 319 | 320 | 321 | 322 | 323 | 324 | 325 | 326 | 327 | 328 | 329 | 330 |
|---|---|---|---|---|---|---|---|---|---|---|---|---|---|---|---|---|---|---|---|---|---|---|---|---|---|---|---|---|---|---|---|
| Y | R | V | V | S | V | L | P | I | L | H | Q | D | W | L | K | G | K | E | F | K | C | K | V | N | S | K | S | L | P | S |

>Feline IgG2_Hinge mut_EU Index

| 300 | 301 | 302 | 303 | 304 | 305 | 306 | 307 | 308 | 309 | 310 | 311 | 312 | 313 | 314 | 315 | 316 | 317 | 318 | 319 | 320 | 321 | 322 | 323 | 324 | 325 | 326 | 327 | 328 | 329 | 330 |
|---|---|---|---|---|---|---|---|---|---|---|---|---|---|---|---|---|---|---|---|---|---|---|---|---|---|---|---|---|---|---|---|
| Y | R | V | V | S | V | L | P | I | L | H | Q | D | W | L | K | G | K | E | F | K | C | K | V | N | S | K | S | L | P | S |

FIGURE 2A (Contd.)

Figure 2A:
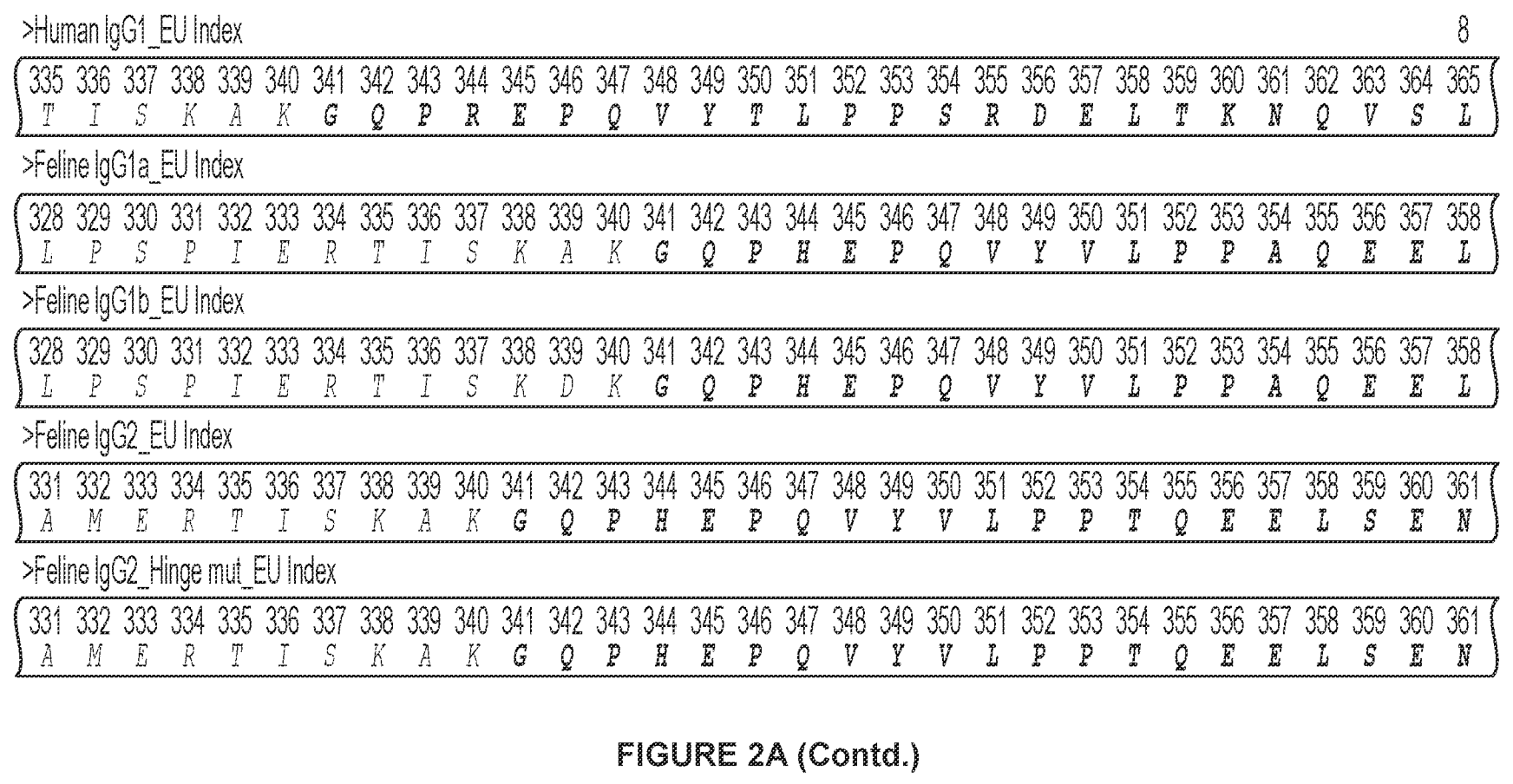

>Human IgG1_EU Index
335 336 337 338 339 340 341 342 343 344 345 346 347 348 349 350 351 352 353 354 355 356 357 358 359 360 361 362 363 364 365
T   I   S   K   A   K   G   Q   P   R   E   P   Q   V   Y   T   L   P   P   S   R   D   E   L   T   K   N   Q   V   S   L >Feline IgG1a_EU Index
328 329 330 331 332 333 334 335 336 337 338 339 340 341 342 343 344 345 346 347 348 349 350 351 352 353 354 355 356 357 358
L   P   S   P   I   E   R   T   I   S   K   A   K   G   Q   P   H   E   P   Q   V   Y   V   L   P   P   A   Q   E   E   L >Feline IgG1b_EU Index
328 329 330 331 332 333 334 335 336 337 338 339 340 341 342 343 344 345 346 347 348 349 350 351 352 353 354 355 356 357 358
L   P   S   P   I   E   R   T   I   S   K   D   K   G   Q   P   H   E   P   Q   V   Y   V   L   P   P   A   Q   E   E   L >Feline IgG2_EU Index
331 332 333 334 335 336 337 338 339 340 341 342 343 344 345 346 347 348 349 350 351 352 353 354 355 356 357 358 359 360 361
A   M   E   R   T   I   S   K   A   K   G   Q   P   H   E   P   Q   V   Y   V   L   P   P   T   Q   E   E   L   S   E   N >Feline IgG2_Hinge mut_EU Index
331 332 333 334 335 336 337 338 339 340 341 342 343 344 345 346 347 348 349 350 351 352 353 354 355 356 357 358 359 360 361
A   M   E   R   T   I   S   K   A   K   G   Q   P   H   E   P   Q   V   Y   V   L   P   P   T   Q   E   E   L   S   E   N FIGURE 2A (Contd.)

>Human IgG1_EU Index

| 366 | 367 | 368 | 369 | 370 | 371 | 372 | 373 | 374 | 375 | 376 | 377 | 378 | 379 | 380 | 381 | 382 | 383 | 384 | 385 | 386 | 387 | 388 | 389 | 390 | 391 | 392 | 393 | 394 | 395 | 396 |
|---|---|---|---|---|---|---|---|---|---|---|---|---|---|---|---|---|---|---|---|---|---|---|---|---|---|---|---|---|---|---|
| T | C | L | V | K | G | F | Y | P | S | D | I | A | V | E | W | E | S | N | G | Q | P | E | N | N | Y | K | T | T | P | P |

(9)

>Feline IgG1a_EU Index

| 359 | 360 | 361 | 362 | 363 | 364 | 365 | 366 | 367 | 368 | 369 | 370 | 371 | 372 | 373 | 374 | 375 | 376 | 377 | 378 | 379 | 380 | 381 | 382 | 383 | 384 | 385 | 386 | 387 |
|---|---|---|---|---|---|---|---|---|---|---|---|---|---|---|---|---|---|---|---|---|---|---|---|---|---|---|---|---|
| S | R | N | K | V | S | V | T | C | L | I | K | S | F | H | P | P | D | I | A | V | E | W | E | I | T | G | Q | P |

>Feline IgG1b_EU Index

| 359 | 360 | 361 | 362 | 363 | 364 | 365 | 366 | 367 | 368 | 369 | 370 | 371 | 372 | 373 | 374 | 375 | 376 | 377 | 378 | 379 | 380 | 381 | 382 | 383 | 384 | 385 | 386 | 387 |
|---|---|---|---|---|---|---|---|---|---|---|---|---|---|---|---|---|---|---|---|---|---|---|---|---|---|---|---|---|---|
| S | R | N | K | V | S | V | T | C | L | I | E | G | F | Y | P | S | D | I | A | V | E | W | E | I | T | G | Q | P |

>Feline IgG2_EU Index

| 362 | 363 | 364 | 365 | 366 | 367 | 368 | 369 | 370 | 371 | 372 | 373 | 374 | 375 | 376 | 377 | 378 | 379 | 380 | 381 | 382 | 383 | 384 | 385 | 386 | 387 | 388 | 389 | 390 |
|---|---|---|---|---|---|---|---|---|---|---|---|---|---|---|---|---|---|---|---|---|---|---|---|---|---|---|---|---|---|
| K | V | S | V | T | C | L | I | K | G | F | H | P | P | D | I | A | V | E | W | E | I | T | G | Q | P | E | N | N |

>Feline IgG2_Hinge mut_EU Index

| 362 | 363 | 364 | 365 | 366 | 367 | 368 | 369 | 370 | 371 | 372 | 373 | 374 | 375 | 376 | 377 | 378 | 379 | 380 | 381 | 382 | 383 | 384 | 385 | 386 | 387 | 388 | 389 | 390 |
|---|---|---|---|---|---|---|---|---|---|---|---|---|---|---|---|---|---|---|---|---|---|---|---|---|---|---|---|---|---|
| K | V | S | V | T | C | L | I | K | G | F | H | P | P | D | I | A | V | E | W | E | I | T | G | Q | P | E | N | N |

FIGURE 2A (Contd.)

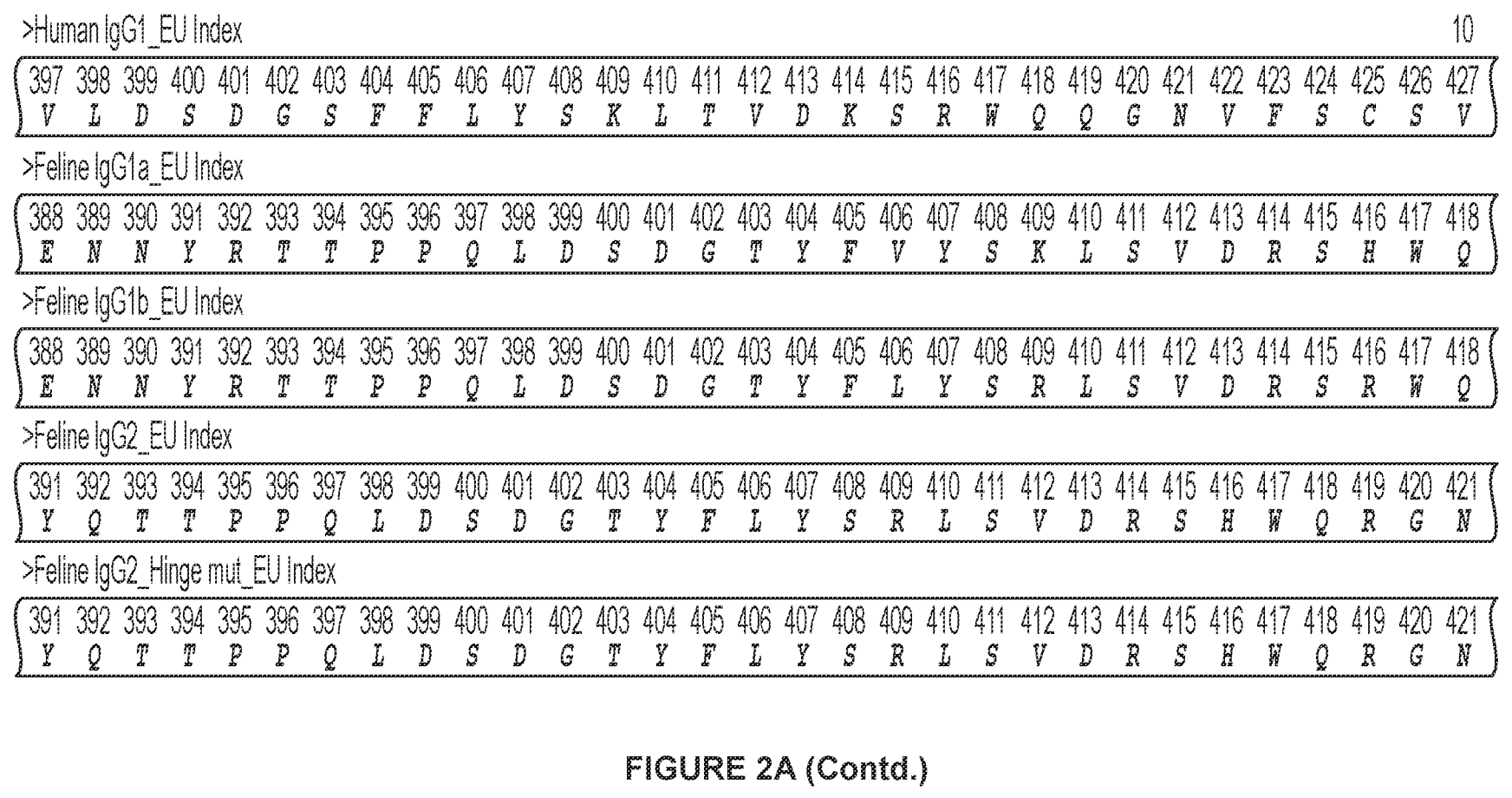

>Human IgG1_EU Index

| 397 | 398 | 399 | 400 | 401 | 402 | 403 | 404 | 405 | 406 | 407 | 408 | 409 | 410 | 411 | 412 | 413 | 414 | 415 | 416 | 417 | 418 | 419 | 420 | 421 | 422 | 423 | 424 | 425 | 426 | 427 |
|---|---|---|---|---|---|---|---|---|---|---|---|---|---|---|---|---|---|---|---|---|---|---|---|---|---|---|---|---|---|---|
| V | L | D | S | D | G | S | F | F | L | Y | S | K | L | T | V | D | K | S | R | W | Q | Q | G | N | V | F | S | C | S | V |

10

>Feline IgG1a_EU Index

| 388 | 389 | 390 | 391 | 392 | 393 | 394 | 395 | 396 | 397 | 398 | 399 | 400 | 401 | 402 | 403 | 404 | 405 | 406 | 407 | 408 | 409 | 410 | 411 | 412 | 413 | 414 | 415 | 416 | 417 | 418 |
|---|---|---|---|---|---|---|---|---|---|---|---|---|---|---|---|---|---|---|---|---|---|---|---|---|---|---|---|---|---|---|
| E | N | N | Y | R | T | T | P | P | Q | L | D | S | D | G | T | Y | F | V | Y | S | K | L | S | V | D | R | S | H | W | Q |

>Feline IgG1b_EU Index

| 388 | 389 | 390 | 391 | 392 | 393 | 394 | 395 | 396 | 397 | 398 | 399 | 400 | 401 | 402 | 403 | 404 | 405 | 406 | 407 | 408 | 409 | 410 | 411 | 412 | 413 | 414 | 415 | 416 | 417 | 418 |
|---|---|---|---|---|---|---|---|---|---|---|---|---|---|---|---|---|---|---|---|---|---|---|---|---|---|---|---|---|---|---|---|
| E | N | N | Y | R | T | T | P | P | Q | L | D | S | D | G | T | Y | F | L | Y | S | R | L | S | V | D | R | S | R | W | Q |

>Feline IgG2_EU Index

| 391 | 392 | 393 | 394 | 395 | 396 | 397 | 398 | 399 | 400 | 401 | 402 | 403 | 404 | 405 | 406 | 407 | 408 | 409 | 410 | 411 | 412 | 413 | 414 | 415 | 416 | 417 | 418 | 419 | 420 | 421 |
|---|---|---|---|---|---|---|---|---|---|---|---|---|---|---|---|---|---|---|---|---|---|---|---|---|---|---|---|---|---|---|---|
| Y | Q | T | T | P | P | Q | L | D | S | D | G | T | Y | F | L | Y | S | R | L | S | V | D | R | S | H | W | Q | R | G | N |

>Feline IgG2_Hinge mut_EU Index

| 391 | 392 | 393 | 394 | 395 | 396 | 397 | 398 | 399 | 400 | 401 | 402 | 403 | 404 | 405 | 406 | 407 | 408 | 409 | 410 | 411 | 412 | 413 | 414 | 415 | 416 | 417 | 418 | 419 | 420 | 421 |
|---|---|---|---|---|---|---|---|---|---|---|---|---|---|---|---|---|---|---|---|---|---|---|---|---|---|---|---|---|---|---|---|
| Y | Q | T | T | P | P | Q | L | D | S | D | G | T | Y | F | L | Y | S | R | L | S | V | D | R | S | H | W | Q | R | G | N |

FIGURE 2A (Contd.)

>Human IgG1_EU Index

| 428 | 429 | 430 | 431 | 432 | 433 | 434 | 435 | 436 | 437 | 438 | 439 | 440 | 441 | 442 | 443 | 444 | 445 | 446 | 447 |
|---|---|---|---|---|---|---|---|---|---|---|---|---|---|---|---|---|---|---|---|
| M | H | E | A | L | H | N | H | Y | T | Q | K | S | L | S | L | S | P | G | K |

>Feline IgG1a_EU Index

| 419 | 420 | 421 | 422 | 423 | 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 | 447 |
|---|---|---|---|---|---|---|---|---|---|---|---|---|---|---|---|---|---|---|---|---|---|---|---|---|---|---|---|---|
| R | G | N | T | Y | T | C | S | V | S | H | E | A | L | H | S | H | H | T | Q | K | S | L | T | Q | S | P | G | K |

>Feline IgG1b_EU Index

| 419 | 420 | 421 | 422 | 423 | 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 | 447 |
|---|---|---|---|---|---|---|---|---|---|---|---|---|---|---|---|---|---|---|---|---|---|---|---|---|---|---|---|---|
| R | G | N | T | Y | T | C | S | V | S | H | E | A | L | H | S | H | H | T | Q | K | S | L | T | Q | S | P | G | K |

>Feline IgG2_EU Index

| 422 | 423 | 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 | 447 |
|---|---|---|---|---|---|---|---|---|---|---|---|---|---|---|---|---|---|---|---|---|---|---|---|---|---|
| T | Y | T | C | S | V | S | H | E | A | L | H | S | H | H | T | Q | K | S | L | T | Q | S | P | G | K |

>Feline IgG2_Hinge mut_EU Index

| 422 | 423 | 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 | 447 |
|---|---|---|---|---|---|---|---|---|---|---|---|---|---|---|---|---|---|---|---|---|---|---|---|---|---|
| T | Y | T | C | S | V | S | H | E | A | L | H | S | H | H | T | Q | K | S | L | T | Q | S | P | G | K |

FIGURE 2A (Contd.)

Feline Fc IgG1a WT nucleotide sequence

```
CCCCCTGAGATGCTTGGAGGACCGTCCATCTTCATCTTCCCCCAA
AACCCAAGGACACCCTCTCGATTTCCCGGACGCCCGAGGTCACAT
GCTTGGTGGTGGGACTTGGGCCCCAGATGACTCCGATGTCCAGATCA
CATGGTTTGTGGATAACACCACCCAGGTGTACACAGACGAGTC
CGCGTGGAGGAGCAGTTCAACACCACCTACCGTGTGGTCAGTGTCC
TCCCCATCCTACACACCAGGACTGGCTCAAGGGGAAGGAGTTCAAGT
GCAAGGTCAACACAGCAAATCCCTCCCCCCACGAGCCCCAGGTACGTCC
TCTCCAAGGCCAAAGGACACAGCCCCACGAGCCCCAGGTGTACGTCC
TGCCTCCAGCCCCAGGAGCTCAGCAGGAACAAAGTCAGTGTGA
CCTGCCTGATCAAATCCTTCCACCCGCCTGACATTGCCGTCGAGTG
GGAGATCACCGGACAGCCGGACAGCGGGACCTACTTCGTGTACAGCA
CCCCGCCCCAGCTGGACAGGTCCCACTGGCAGAGGGGAAACACCTACA
AGCTCTCGGTGGACAGGTCTCACGAGCTCTGCACGAGCTCCACCACACAGA
CCTGCTCGGTCGTCACGAGCTCTGCACGAGCTCCACCACACAGA
AATCCCTCACCCAGTCTCCGGGTAAA
```

FIGURE 2B

Feline Fc IgG1a S434H nucleotide sequence

```
CCCCCTGAGATGCTTGGGAGGACCGTCCATCTTCATCTTCCCCCCAA
AACCCAAGGACACCCTCTCGATTTCCCGGACGCCCGAGGTCACAT
GCTTGGTGGTGGACTTGGGCCCCAGATGACTCCGATGTCCAGATCA
CATGGTTTGTGGATAACACCCCAGGTGTACACAGCCAAGACGAGTC
CGCGTGAGGAGCAGTTCAACACCTACCGTGTGGTCAGTGTCC
TCCCCATCCTACACACCAGGACTGGCTCAAGGGGAAGGAGTTCAAGT
GCAAGGTCAACACCAGCAAATCCCTCCCCACGAGCCCATCGAGGACCA
TCTCCAAGGCCAAAGGACACAGCCCCACGAGCCCCAGGTGTACGTCC
TGCCTCCAGCCCAGGAGGAGCTCAGCAGGAACAAAGTCAGTGTGA
CCTGCCTGATCAAATCCTTCCACCCGCCTGACATTGCCGTCGAGTG
GGAGATCACCGGACAGCCGGACAGCGGACGGGACCTACTTCGTGTACAGCA
CCCCGCCCCAGCTGGACAGCGGACAGGTCCCACTGGCAGAGGGGAAACACCTACA
AGCTCTCGGTGGACAGGTCTCACGACGAGCTCTGCACCACCACACAGA
CCTGCTCGGTGTCACGACGAGCTCTGCACCACCACACAGA
AATCCCTCACCCAGTCTCCGGGTAAA
```

FIGURE 2C

Feline Fc IgG1a S428L nucleotide sequence

CCCCCTGAGATGCTTGGAGGAGGACCGTCCATCTTCATCTTCCCCCAA
AACCCAAGGACACCCCTCTCGATTTCCCGACGCCCGAGGTCACAT
GCTTGGTGGTGGACTTGGGCCCAGATGACTCCGATGTCCAGATCA
CATGGTTTGTGGATAACACCCAGGTGTACACAGACCAAGACGAGTC
CGCGTGGAGGAGCAGTTCAACACCTACCGTGTGGTCAGTGTCC
TCCCCATCCTACACCAGGACTGGCTCAAGGGGAAGGAGTTCAAGT
GCAAGGTCAACACCAGGACAAATCCCTCCCCCATCCGAGAGGACCA
TCTCCAAGGCCAAAGGACAGCAGCCCCACGAGGTGTACGTCC
TGCCTCCAGCCCAGGAGGAGCTCAGCAGGAACAAAGTCAGTGTGA
CCTGCCTGATCAAATCCTTCCACCCGCCTGACATTGCCGTCGAGTG
GGAGATCACCGGACAGCCGGACAGCGGACGGGAACAACTACCGGACGA
CCCCGCCCAGCTGGACAGCGGACAGCGGGACGGGGAAACACCTACA
AGCTCTCGGTGACAGGTCCCACTGGCACAGAGGGGAAACACCTACA
CCTGCTCGGTGCTGCACGAGCTCTGCACCACACAGA
AATCCCTCACCCAGTCTCCGGGTAAA

FIGURE 2D

SEQUENCE LISTING

<160> NUMBER OF SEQ ID NOS: 138

<210> SEQ ID NO 1
<211> LENGTH: 335
<212> TYPE: PRT
<213> ORGANISM: Felis catus

<400> SEQUENCE: 1

```
Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ala Ser Gly Leu Tyr Ser
        50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
            115                 120                 125

Phe Pro Pro Lys Pro Lys Asp Thr Leu Ser Ile Ser Arg Thr Pro Glu
        130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
            195                 200                 205

Val Asn Ser Lys Ser Leu Pro Ser Pro Ile Glu Arg Thr Ile Ser Lys
        210                 215                 220

Ala Lys Gly Gln Pro His Glu Pro Gln Val Tyr Val Leu Pro Pro Ala
225                 230                 235                 240
```

-continued

```
Gln Glu Glu Leu Ser Arg Asn Lys Val Ser Val Thr Cys Leu Ile Lys
                245                 250                 255

Ser Phe His Pro Pro Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
            275                 280                 285

Asp Gly Thr Tyr Phe Val Tyr Ser Lys Leu Ser Val Asp Arg Ser His
        290                 295                 300

Trp Gln Arg Gly Asn Thr Tyr Thr Cys Ser Val Leu His Glu Ala Leu
    305                 310                 315                 320

His Ser His His Thr Gln Lys Ser Leu Thr Gln Ser Pro Gly Lys
                325                 330                 335

<210> SEQ ID NO 2
<211> LENGTH: 335
<212> TYPE: PRT
<213> ORGANISM: Felis catus

<400> SEQUENCE: 2

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ala Ser Gly Leu Tyr Ser
        50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val Arg Lys Thr Asp His Pro Pro Gly Pro Lys Pro Cys Asp Cys
            100                 105                 110

Pro Lys Cys Pro Pro Pro Glu Met Leu Gly Gly Pro Ser Ile Phe Ile
            115                 120                 125

Phe Pro Pro Lys Pro Lys Asp Thr Leu Ser Ile Ser Arg Thr Pro Glu
        130                 135                 140

Val Thr Cys Leu Val Val Asp Leu Gly Pro Asp Asp Ser Asp Val Gln
145                 150                 155                 160

Ile Thr Trp Phe Val Asp Asn Thr Gln Val Tyr Thr Ala Lys Thr Ser
                165                 170                 175

Pro Arg Glu Glu Gln Phe Asn Ser Thr Tyr Arg Val Val Ser Val Leu
            180                 185                 190

Pro Ile Leu His Gln Asp Trp Leu Lys Gly Lys Glu Phe Lys Cys Lys
            195                 200                 205

Val Asn Ser Lys Ser Leu Pro Ser Pro Ile Glu Arg Thr Ile Ser Lys
        210                 215                 220

Ala Lys Gly Gln Pro His Glu Pro Gln Val Tyr Val Leu Pro Pro Ala
225                 230                 235                 240

Gln Glu Glu Leu Ser Arg Asn Lys Val Ser Val Thr Cys Leu Ile Lys
                245                 250                 255

Ser Phe His Pro Pro Asp Ile Ala Val Glu Trp Glu Ile Thr Gly Gln
            260                 265                 270

Pro Glu Pro Glu Asn Asn Tyr Arg Thr Thr Pro Pro Gln Leu Asp Ser
            275                 280                 285
```

```
Asp Gly Thr Tyr Phe Val Tyr Ser Lys Leu Ser Val Asp Arg Ser His
    290             295             300

Trp Gln Arg Gly Asn Thr Tyr Thr Cys Ser Val Ser His Glu Ala Leu
305             310             315             320

His His His His Thr Gln Lys Ser Leu Thr Gln Ser Pro Gly Lys
            325             330             335

<210> SEQ ID NO 3
<211> LENGTH: 335
<212> TYPE: PRT
<213> ORGANISM: Felis catus

<400> SEQUENCE: 3

Ala Ser Thr Thr Ala Pro Ser Val Phe Pro Leu Ala Pro Ser Cys Gly
1               5               10              15

Thr Thr Ser Gly Ala Thr Val Ala Leu Ala Cys Leu Val Leu Gly Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ala Ser Gly Leu Tyr Ser
    50              55              60

Leu Ser Ser Met Val Thr Val Pro Ser Ser Arg Trp Leu Ser Asp Thr
65              70              75              80

Phe Thr Cys Asn Val Ala His Pro Pro Ser Asn Thr Lys Val Asp Lys
            85              90              95

Thr Val Arg Lys Thr Asp His Pro Pro Gly Pro Lys Pro Cys Asp Cys
            100             105             110

Pro Lys Cys Pro Pro Pro Glu Met Leu Gly Gly Pro Ser Ile Phe Ile
            115             120             125

Phe Pro Pro Lys Pro Lys Asp Thr Leu Ser Ile Ser Arg Thr Pro Glu
            130             135             140

Val Thr Cys Leu Val Val Asp Leu Gly Pro Asp Asp Ser Asp Val Gln
145             150             155             160

Ile Thr Trp Phe Val Asp Asn Thr Gln Val Tyr Thr Ala Lys Thr Ser
            165             170             175

Pro Arg Glu Glu Gln Phe Asn Ser Thr Tyr Arg Val Val Ser Val Leu
            180             185             190

Pro Ile Leu His Gln Asp Trp Leu Lys Gly Lys Glu Phe Lys Cys Lys
            195             200             205

Val Asn Ser Lys Ser Leu Pro Ser Pro Ile Glu Arg Thr Ile Ser Lys
    210             215             220

Ala Lys Gly Gln Pro His Glu Pro Gln Val Tyr Val Leu Pro Pro Ala
225             230             235             240

Gln Glu Glu Leu Ser Arg Asn Lys Val Ser Val Thr Cys Leu Ile Lys
            245             250             255

Ser Phe His Pro Pro Asp Ile Ala Val Glu Trp Glu Ile Thr Gly Gln
            260             265             270

Pro Glu Pro Glu Asn Asn Tyr Arg Thr Thr Pro Pro Gln Leu Asp Ser
            275             280             285

Asp Gly Thr Tyr Phe Val Tyr Ser Lys Leu Ser Val Asp Arg Ser His
    290             295             300

Trp Gln Arg Gly Asn Thr Tyr Thr Cys Ser Val Ser His Glu Ala Leu
305             310             315             320

His Ser His His Thr Gln Lys Ser Leu Thr Gln Ser Pro Gly Lys
```

```
                 325              330              335

<210> SEQ ID NO 4
<211> LENGTH: 1005
<212> TYPE: DNA
<213> ORGANISM: Felis catus

<400> SEQUENCE: 4
gcctccacca cggccccatc ggtgttccca ctggcccca gctgcgggac cacatctggc        60
gccaccgtgg ccctggcctg cctggtgtta ggctacttcc ctgagccggt gaccgtgtcc       120
tggaactccg gcgccctgac cagcggtgtg cacaccttcc cggccgtcct gcaggcctcg       180
gggctgtact ctctcagcag catggtgaca gtgccctcca gcaggtggct cagtgacacc       240
ttcacctgca acgtggccca cccgcccagc aacaccaagg tggacaagac cgtgcgcaaa       300
acagaccacc caccgggacc caaaccctgc gactgtccca atgcccacc ccctgagatg        360 cttggaggac cgtccatctt catcttcccc ccaaaaccca aggacaccct ctcgatttcc       420
cggacgcccg aggtcacatg cttggtggtg acttgggcc cagatgactc cgatgtccag        480
atcacatggt ttgtggataa cacccaggtg tacacagcca agacgagtcc gcgtgaggag       540
cagttcaaca gcacctaccg tgtggtcagt gtcctcccca tcctacacca ggactggctc       600 aagggggaagg agttcaagtg caaggtcaac agcaaatccc tcccctcccc catcgagagg      660
accatctcca aggccaaagg acagcccac gagccccagg tgtacgtcct gcctccagcc        720
caggaggagc tcagcaggaa caaagtcagt gtgacctgcc tgatcaaatc cttccacccg       780
cctgacattg ccgtcgagtg gggagatcacc ggacagccgg agccagagaa caactaccgg      840 acgacccgc cccagctgga cagcgacggg acctacttcg tgtacagcaa gctctcggtg        900
gacaggtccc actggcagag gggaaacacc tacacctgct cggtgtcaca cgaagctctg       960
cacagccacc acacacagaa atccctcacc cagtctccgg gtaaa                      1005

<210> SEQ ID NO 5
<211> LENGTH: 98
<212> TYPE: PRT
<213> ORGANISM: Felis catus

<400> SEQUENCE: 5

Ala Ser Thr Thr Ala Pro Ser Val Phe Pro Leu Ala Pro Ser Cys Gly
1               5                   10                  15

Thr Thr Ser Gly Ala Thr Val Ala Leu Ala Cys Leu Val Leu Gly Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ala Ser Gly Leu Tyr Ser
    50                  55                  60

Leu Ser Ser Met Val Thr Val Pro Ser Ser Arg Trp Leu Ser Asp Thr
65                  70                  75                  80

Phe Thr Cys Asn Val Ala His Pro Pro Ser Asn Thr Lys Val Asp Lys
                85                  90                  95

Thr Val

<210> SEQ ID NO 6
<211> LENGTH: 18
<212> TYPE: PRT
<213> ORGANISM: Felis catus

<400> SEQUENCE: 6
```

-continued

```
Arg Lys Thr Asp His Pro Pro Gly Pro Lys Pro Cys Asp Cys Pro Lys
1               5                   10                  15

Cys Pro

<210> SEQ ID NO 7
<211> LENGTH: 110
<212> TYPE: PRT
<213> ORGANISM: Felis catus

<400> SEQUENCE: 7

Pro Pro Glu Met Leu Gly Gly Pro Ser Ile Phe Ile Phe Pro Pro Lys
1               5                   10                  15

Pro Lys Asp Thr Leu Ser Ile Ser Arg Thr Pro Glu Val Thr Cys Leu
            20                  25                  30

Val Val Asp Leu Gly Pro Asp Asp Ser Asp Val Gln Ile Thr Trp Phe
            35                  40                  45

Val Asp Asn Thr Gln Val Tyr Thr Ala Lys Thr Ser Pro Arg Glu Glu
            50                  55                  60

Gln Phe Asn Ser Thr Tyr Arg Val Val Ser Val Leu Pro Ile Leu His
65                  70                  75                  80

Gln Asp Trp Leu Lys Gly Lys Glu Phe Lys Cys Lys Val Asn Ser Lys
                85                  90                  95

Ser Leu Pro Ser Pro Ile Glu Arg Thr Ile Ser Lys Ala Lys
            100                 105                 110

<210> SEQ ID NO 8
<211> LENGTH: 109
<212> TYPE: PRT
<213> ORGANISM: Felis catus

<400> SEQUENCE: 8

Gly Gln Pro His Glu Pro Gln Val Tyr Val Leu Pro Pro Ala Gln Glu
1               5                   10                  15

Glu Leu Ser Arg Asn Lys Val Ser Val Thr Cys Leu Ile Lys Ser Phe
            20                  25                  30

His Pro Pro Asp Ile Ala Val Glu Trp Glu Ile Thr Gly Gln Pro Glu
            35                  40                  45

Pro Glu Asn Asn Tyr Arg Thr Thr Pro Pro Gln Leu Asp Ser Asp Gly
            50                  55                  60

Thr Tyr Phe Val Tyr Ser Lys Leu Ser Val Asp Arg Ser His Trp Gln
65                  70                  75                  80

Arg Gly Asn Thr Tyr Thr Cys Ser Val Ser His Glu Ala Leu His Ser
                85                  90                  95

His His Thr Gln Lys Ser Leu Thr Gln Ser Pro Gly Lys
            100                 105

<210> SEQ ID NO 9
<211> LENGTH: 294
<212> TYPE: DNA
<213> ORGANISM: Felis catus

<400> SEQUENCE: 9
gcctccacca cggccccatc ggtgttccca ctggcccca gctgcgggac cacatctggc        60
gccaccgtgg ccctggcctg cctggtgtta ggctacttcc ctgagccggt gaccgtgtcc       120
tggaactccg gcgccctgac cagcggtgtg cacaccttcc cggccgtcct gcaggcctcg       180
gggctgtact ctctcagcag catggtgaca gtgccctcca gcaggtggct cagtgacacc       240
```

-continued

```
ttcacctgca acgtggccca cccgcccagc aacaccaagg tggacaagac cgtg          294

<210> SEQ ID NO 10
<211> LENGTH: 54
<212> TYPE: DNA
<213> ORGANISM: Felis catus

<400> SEQUENCE: 10
cgcaaaacag accacccacc gggacccaaa ccctgcgact gtcccaaatg ccca          54

<210> SEQ ID NO 11
<211> LENGTH: 330
<212> TYPE: DNA
<213> ORGANISM: Felis catus

<400> SEQUENCE: 11
ccccctgaga tgcttggagg accgtccatc ttcatcttcc ccccaaaacc caaggacacc    60
ctctcgattt cccggacgcc cgaggtcaca tgcttggtgg tggacttggg cccagatgac    120
tccgatgtcc agatcacatg gtttgtggat aacacccagg tgtacacagc caagacgagt    180
ccgcgtgagg agcagttcaa cagcacctac cgtgtggtca gtgtcctccc catcctacac    240
caggactggc tcaaggggaa ggagttcaag tgcaaggtca acagcaaatc cctcccctcc    300
cccatcgaga ggaccatctc caaggccaaa                                      330

<210> SEQ ID NO 12
<211> LENGTH: 327
<212> TYPE: DNA
<213> ORGANISM: Felis catus

<400> SEQUENCE: 12
ggacagcccc acgagcccca ggtgtacgtc ctgcctccag cccaggagga gctcagcagg    60
aacaaagtca gtgtgacctg cctgatcaaa tccttccacc cgcctgacat tgccgtcgag    120
tgggagatca ccggacagcc ggagccagag aacaactacc ggacgacccc gccccagctg    180
gacagcgacg ggacctactt cgtgtacagc aagctctcgg tggacaggtc ccactggcag    240
aggggaaaca cctacacctg ctcggtgtca cacgaagctc tgcacagcca ccacacacag    300
aaatccctca cccagtctcc gggtaaa                                        327

<210> SEQ ID NO 13
<211> LENGTH: 351
<212> TYPE: DNA
<213> ORGANISM: Artificial Sequence
<220> FEATURE:
<223> OTHER INFORMATION: ZTS-5864 Heavy Chain Variable Region

<400> SEQUENCE: 13
gacgtgcaat tggtggagtc tgggggagac ctggtgaagc ctgggggggtc cctgagactc   60 acctgtgtgg cctctggatt caccttcagt gactatgcaa tgagctgggt ccgccaggct    120
ccagggaagg ggctgcagtg ggtcgcaggt attgacagtg ttggaagtgg cacaagctac    180
gcagactccg tgaagggccg attcaccatc tccagagaca tgccaagaa cacgctgtat     240 ctgcagatga acagcctcaa gaccgaggac acggccacat attactgtgc gagcgggttc    300
cctgggtcct ttgagcactg gggccaagga accctggtga cggtctcgag c             351

<210> SEQ ID NO 14
<211> LENGTH: 117
<212> TYPE: PRT
```

-continued

<213> ORGANISM: Artificial Sequence
<220> FEATURE:
<223> OTHER INFORMATION: ZTS-5864 Heavy Chain Variable Region

<400> SEQUENCE: 14

Asp Val Gln Leu Val Glu Ser Gly Gly Asp Leu Val Lys Pro Gly Gly
1               5                   10                  15

Ser Leu Arg Leu Thr Cys Val Ala Ser Gly Phe Thr Phe Ser Asp Tyr
            20                  25                  30

Ala Met Ser Trp Val Arg Gln Ala Pro Gly Lys Gly Leu Gln Trp Val
        35                  40                  45

Ala Gly Ile Asp Ser Val Gly Ser Gly Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Thr Glu Asp Thr Ala Thr Tyr Tyr Cys
                85                  90                  95

Ala Ser Gly Phe Pro Gly Ser Phe Glu His Trp Gly Gln Gly Thr Leu
            100                 105                 110

Val Thr Val Ser Ser
        115

<210> SEQ ID NO 15
<211> LENGTH: 5
<212> TYPE: PRT
<213> ORGANISM: Canis familiaris

<400> SEQUENCE: 15

Asp Tyr Ala Met Ser
1               5

<210> SEQ ID NO 16
<211> LENGTH: 17
<212> TYPE: PRT
<213> ORGANISM: Canis familiaris

<400> SEQUENCE: 16

Gly Ile Asp Ser Val Gly Ser Gly Thr Ser Tyr Ala Asp Ser Val Lys
1               5                   10                  15

Gly

<210> SEQ ID NO 17
<211> LENGTH: 8
<212> TYPE: PRT
<213> ORGANISM: Canis familiaris

<400> SEQUENCE: 17

Gly Phe Pro Gly Ser Phe Glu His
1               5

<210> SEQ ID NO 18
<211> LENGTH: 312
<212> TYPE: DNA
<213> ORGANISM: Artificial Sequence
<220> FEATURE:
<223> OTHER INFORMATION: ZTS-5864 Light Chain Variable Region

<400> SEQUENCE: 18
cagtctgtgc tgactcagcc atcctcagtg tctgggaccc taggccagag gatcaccatc        60
tcctgcaccg gaagcagctc caacatcggg agtggttatg tgggctggta tcaacaagtc       120

-continued

```
ccaggaatgg gccccaaaac cgtcatctat tataatagcg accgaccctc tggagtccca      180
gataggttct ccggctccaa gtctggcagc tcaggcaccc tgaccatcac tggattgcag      240
gctgaagacg aggctgacta ttactgttca gtatatgaca gaactttcaa tgctgtgttc      300
ggcggaggga cc                                                         312
```

```
<210> SEQ ID NO 19
<211> LENGTH: 104
<212> TYPE: PRT
<213> ORGANISM: Artificial Sequence
<220> FEATURE:
<223> OTHER INFORMATION: ZTS-5864 Light Chain Variable Region

<400> SEQUENCE: 19

Gln Ser Val Leu Thr Gln Pro Ser Ser Val Ser Gly Thr Leu Gly Gln
1               5                   10                  15

Arg Ile Thr Ile Ser Cys Thr Gly Ser Ser Ser Asn Ile Gly Ser Gly
            20                  25                  30

Tyr Val Gly Trp Tyr Gln Gln Val Pro Gly Met Gly Pro Lys Thr Val
        35                  40                  45

Ile Tyr Tyr Asn Ser Asp Arg Pro Ser Gly Val Pro Asp Arg Phe Ser
    50                  55                  60

Gly Ser Lys Ser Gly Ser Ser Gly Thr Leu Thr Ile Thr Gly Leu Gln
65                  70                  75                  80

Ala Glu Asp Glu Ala Asp Tyr Tyr Cys Ser Val Tyr Asp Arg Thr Phe
                85                  90                  95

Asn Ala Val Phe Gly Gly Gly Thr
            100
```

```
<210> SEQ ID NO 20
<211> LENGTH: 13
<212> TYPE: PRT
<213> ORGANISM: Canis familiaris

<400> SEQUENCE: 20

Thr Gly Ser Ser Ser Asn Ile Gly Ser Gly Tyr Val Gly
1               5                   10
```

```
<210> SEQ ID NO 21
<211> LENGTH: 7
<212> TYPE: PRT
<213> ORGANISM: Canis familiaris

<400> SEQUENCE: 21

Tyr Tyr Asn Ser Asp Arg Pro
1               5
```

```
<210> SEQ ID NO 22
<211> LENGTH: 10
<212> TYPE: PRT
<213> ORGANISM: Canis familiaris

<400> SEQUENCE: 22

Ser Val Tyr Asp Arg Thr Phe Asn Ala Val
1               5                   10
```

```
<210> SEQ ID NO 23
<211> LENGTH: 453
<212> TYPE: PRT
<213> ORGANISM: Artificial Sequence
<220> FEATURE:
<223> OTHER INFORMATION: ZTS768_Heavy_chain
```

-continued

```
<400> SEQUENCE: 23

Asp Val Gln Leu Val Glu Ser Gly Gly Asp Leu Val Lys Pro Gly Gly
1               5                   10                  15

Ser Leu Arg Leu Thr Cys Val Ala Ser Gly Phe Thr Tyr Ser Asn Tyr
            20                  25                  30

Trp Met His Trp Val Arg Gln Ala Pro Gly Lys Gly Leu Gln Trp Val
        35                  40                  45

Ala Arg Ile Asp Pro Tyr Gly Gly Gly Thr Lys His Asn Glu Lys Phe
    50                  55                  60

Lys Arg Arg Phe Thr Ile Ser Arg Asp Asn Ala Lys Asn Thr Leu Tyr
65                  70                  75                  80

Leu Gln Met Asn Ser Leu Lys Thr Glu Asp Thr Ala Thr Tyr Tyr Cys
                85                  90                  95

Val Arg Ser Gly Tyr Asp Tyr Tyr Phe Asp Val Trp Gly Gln Gly Thr
            100                 105                 110

Leu Val Thr Val Ser Ser Ala Ser Thr Thr Ala Pro Ser Val Phe Pro
        115                 120                 125

Leu Ala Pro Ser Cys Gly Thr Thr Ser Gly Ala Thr Val Ala Leu Ala
    130                 135                 140

Cys Leu Val Leu Gly Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ala Ser Gly Leu Tyr Ser Leu Ser Ser Met Val Thr Val Pro Ser Ser
            180                 185                 190

Arg Trp Leu Ser Asp Thr Phe Thr Cys Asn Val Ala His Pro Pro Ser
        195                 200                 205

Asn Thr Lys Val Asp Lys Thr Val Arg Lys Thr Asp His Pro Pro Gly
    210                 215                 220

Pro Lys Pro Cys Asp Cys Pro Lys Cys Pro Pro Pro Glu Met Leu Gly
225                 230                 235                 240

Gly Pro Ser Ile Phe Ile Phe Pro Pro Lys Pro Lys Asp Thr Leu Ser
            245                 250                 255

Ile Ser Arg Thr Pro Glu Val Thr Cys Leu Val Val Asp Leu Gly Pro
            260                 265                 270

Asp Asp Ser Asp Val Gln Ile Thr Trp Phe Val Asp Asn Thr Gln Val
        275                 280                 285

Tyr Thr Ala Lys Thr Ser Pro Arg Glu Glu Gln Phe Asn Ser Thr Tyr
    290                 295                 300

Arg Val Val Ser Val Leu Pro Ile Leu His Gln Asp Trp Leu Lys Gly
305                 310                 315                 320

Lys Glu Phe Lys Cys Lys Val Asn Ser Lys Ser Leu Pro Ser Pro Ile
            325                 330                 335

Glu Arg Thr Ile Ser Lys Ala Lys Gly Gln Pro His Glu Pro Gln Val
            340                 345                 350

Tyr Val Leu Pro Pro Ala Gln Glu Glu Leu Ser Arg Asn Lys Val Ser
        355                 360                 365

Val Thr Cys Leu Ile Lys Ser Phe His Pro Pro Asp Ile Ala Val Glu
    370                 375                 380

Trp Glu Ile Thr Gly Gln Pro Glu Pro Glu Asn Asn Tyr Arg Thr Thr
385                 390                 395                 400

Pro Pro Gln Leu Asp Ser Asp Gly Thr Tyr Phe Val Tyr Ser Lys Leu
```

-continued

```
                405              410              415
Ser Val Asp Arg Ser His Trp Gln Arg Gly Asn Thr Tyr Thr Cys Ser
            420              425              430

Val Ser His Glu Ala Leu His Ser His His Thr Gln Lys Ser Leu Thr
        435              440              445

Gln Ser Pro Gly Lys
    450

<210> SEQ ID NO 24
<211> LENGTH: 5
<212> TYPE: PRT
<213> ORGANISM: Mus musculus

<400> SEQUENCE: 24

Asn Tyr Trp Met His
1               5

<210> SEQ ID NO 25
<211> LENGTH: 17
<212> TYPE: PRT
<213> ORGANISM: Mus musculus

<400> SEQUENCE: 25

Arg Ile Asp Pro Tyr Gly Gly Gly Thr Lys His Asn Glu Lys Phe Lys
1               5              10              15

Arg

<210> SEQ ID NO 26
<211> LENGTH: 9
<212> TYPE: PRT
<213> ORGANISM: Mus musculus

<400> SEQUENCE: 26

Ser Gly Tyr Asp Tyr Tyr Phe Asp Val
1               5

<210> SEQ ID NO 27
<211> LENGTH: 217
<212> TYPE: PRT
<213> ORGANISM: Artificial Sequence
<220> FEATURE:
<223> OTHER INFORMATION: ZTS768_Light_chain

<400> SEQUENCE: 27

Glu Ile Gln Met Thr Gln Ser Pro Ser Ser Leu Ser Ala Ser Pro Gly
1               5              10              15

Asp Arg Val Thr Ile Thr Cys Arg Ala Ser Glu Asn Ile Tyr Ser Phe
            20              25              30

Leu Ala Trp Tyr Gln Gln Lys Pro Gly Lys Val Pro Lys Leu Leu Ile
        35              40              45

Tyr Asn Ala Asn Thr Leu Ala Glu Gly Val Pro Ser Arg Phe Ser Gly
    50              55              60

Ser Gly Ser Gly Thr Asp Phe Thr Leu Thr Ile Ser Ser Leu Glu Pro
65              70              75              80

Glu Asp Ala Ala Thr Tyr Tyr Cys Gln His His Phe Gly Thr Pro Phe
                85              90              95

Thr Phe Gly Ser Gly Thr Lys Leu Glu Ile Lys Arg Ser Asp Ala Gln
            100             105             110

Pro Ser Val Phe Leu Phe Gln Pro Ser Leu Asp Glu Leu His Thr Gly
        115             120             125
```

```
Ser Ala Ser Ile Val Cys Ile Leu Asn Asp Phe Tyr Pro Lys Glu Val
    130                 135             140

Asn Val Lys Trp Lys Val Asp Gly Val Val Gln Asn Lys Gly Ile Gln
145             150             155             160

Glu Ser Thr Thr Glu Gln Asn Ser Lys Asp Ser Thr Tyr Ser Leu Ser
            165             170             175

Ser Thr Leu Thr Met Ser Ser Thr Glu Tyr Gln Ser His Glu Lys Phe
        180             185             190

Ser Cys Glu Val Thr His Lys Ser Leu Ala Ser Thr Leu Val Lys Ser
        195             200             205

Phe Gln Arg Ser Glu Cys Gln Arg Glu
    210             215
```

```
<210> SEQ ID NO 28
<211> LENGTH: 11
<212> TYPE: PRT
<213> ORGANISM: Mus musculus

<400> SEQUENCE: 28

Arg Ala Ser Glu Asn Ile Tyr Ser Phe Leu Ala
1               5               10
```

```
<210> SEQ ID NO 29
<211> LENGTH: 7
<212> TYPE: PRT
<213> ORGANISM: Mus musculus

<400> SEQUENCE: 29

Asn Ala Asn Thr Leu Ala Glu
1               5
```

```
<210> SEQ ID NO 30
<211> LENGTH: 9
<212> TYPE: PRT
<213> ORGANISM: Mus musculus

<400> SEQUENCE: 30

Gln His His Phe Gly Thr Pro Phe Thr
1               5
```

```
<210> SEQ ID NO 31
<211> LENGTH: 457
<212> TYPE: PRT
<213> ORGANISM: Artificial Sequence
<220> FEATURE:
<223> OTHER INFORMATION: NV02_Heavy chain

<400> SEQUENCE: 31

Gln Val Gln Leu Val Glu Ser Gly Ala Glu Leu Val Gln Pro Gly Glu
1               5               10              15

Ser Leu Arg Leu Thr Cys Ala Ala Ser Gly Phe Ser Leu Thr Asn Asn
            20              25              30

Asn Val Asn Trp Val Arg Gln Ala Pro Gly Lys Gly Leu Glu Trp Met
        35              40              45

Gly Gly Val Trp Ala Gly Gly Ala Thr Asp Tyr Asn Ser Ala Leu Lys
    50              55              60

Ser Arg Leu Thr Ile Thr Arg Asp Thr Ser Lys Asn Thr Val Phe Leu
65              70              75              80

Gln Met His Ser Leu Gln Ser Glu Asp Thr Ala Thr Tyr Tyr Cys Ala
            85              90              95
```

```
Arg Asp Gly Gly Tyr Ser Ser Ser Thr Leu Tyr Ala Met Asp Ala Trp
        100             105             110

Gly Gln Gly Thr Thr Val Thr Val Ser Ala Ala Ser Thr Thr Ala Pro
        115             120             125

Ser Val Phe Pro Leu Ala Pro Ser Cys Gly Thr Thr Ser Gly Ala Thr
        130             135             140

Val Ala Leu Ala Cys Leu Val Leu Gly Tyr Phe Pro Glu Pro Val Thr
145             150             155             160

Val Ser Trp Asn Ser Gly Ala Leu Thr Ser Gly Val His Thr Phe Pro
            165             170             175

Ala Val Leu Gln Ala Ser Gly Leu Tyr Ser Leu Ser Ser Met Val Thr
        180             185             190

Val Pro Ser Ser Arg Trp Leu Ser Asp Thr Phe Thr Cys Asn Val Ala
        195             200             205

His Pro Pro Ser Asn Thr Lys Val Asp Lys Thr Val Arg Lys Thr Asp
        210             215             220

His Pro Pro Gly Pro Lys Pro Cys Asp Cys Pro Lys Cys Pro Pro Pro
225             230             235             240

Glu Met Leu Gly Gly Pro Ser Ile Phe Ile Phe Pro Pro Lys Pro Lys
            245             250             255

Asp Thr Leu Ser Ile Ser Arg Thr Pro Glu Val Thr Cys Leu Val Val
            260             265             270

Asp Leu Gly Pro Asp Asp Ser Asp Val Gln Ile Thr Trp Phe Val Asp
        275             280             285

Asn Thr Gln Val Tyr Thr Ala Lys Thr Ser Pro Arg Glu Glu Gln Phe
        290             295             300

Asn Ser Thr Tyr Arg Val Val Ser Val Leu Pro Ile Leu His Gln Asp
305             310             315             320

Trp Leu Lys Gly Lys Glu Phe Lys Cys Lys Val Asn Ser Lys Ser Leu
            325             330             335

Pro Ser Pro Ile Glu Arg Thr Ile Ser Lys Ala Lys Gly Gln Pro His
            340             345             350

Glu Pro Gln Val Tyr Val Leu Pro Pro Ala Gln Glu Glu Leu Ser Arg
        355             360             365

Asn Lys Val Ser Val Thr Cys Leu Ile Lys Ser Phe His Pro Pro Asp
        370             375             380

Ile Ala Val Glu Trp Glu Ile Thr Gly Gln Pro Glu Pro Glu Asn Asn
385             390             395             400

Tyr Arg Thr Thr Pro Pro Gln Leu Asp Ser Asp Gly Thr Tyr Phe Val
            405             410             415

Tyr Ser Lys Leu Ser Val Asp Arg Ser His Trp Gln Arg Gly Asn Thr
            420             425             430

Tyr Thr Cys Ser Val Ser His Glu Ala Leu His Ser His His Thr Gln
            435             440             445

Lys Ser Leu Thr Gln Ser Pro Gly Lys
        450             455
```

```
<210> SEQ ID NO 32
<211> LENGTH: 10
<212> TYPE: PRT
<213> ORGANISM: Rattus rattus

<400> SEQUENCE: 32

Gly Phe Ser Leu Thr Asn Asn Asn Val Asn
```

1                5                      10

<210> SEQ ID NO 33
<211> LENGTH: 16
<212> TYPE: PRT
<213> ORGANISM: Rattus rattus

<400> SEQUENCE: 33

Gly Val Trp Ala Gly Gly Ala Thr Asp Tyr Asn Ser Ala Leu Lys Ser
1               5                   10                  15

<210> SEQ ID NO 34
<211> LENGTH: 14
<212> TYPE: PRT
<213> ORGANISM: Rattus rattus

<400> SEQUENCE: 34

Asp Gly Gly Tyr Ser Ser Ser Thr Leu Tyr Ala Met Asp Ala
1               5                   10

<210> SEQ ID NO 35
<211> LENGTH: 217
<212> TYPE: PRT
<213> ORGANISM: Artificial Sequence
<220> FEATURE:
<223> OTHER INFORMATION: >NV02_Kappa chain

<400> SEQUENCE: 35

Asp Ile Glu Met Thr Gln Ser Pro Leu Ser Leu Ser Val Thr Pro Gly
1               5                   10                  15

Glu Ser Val Ser Ile Ser Cys Arg Ala Ser Glu Asp Ile Tyr Asn Ala
            20                  25                  30

Leu Ala Trp Tyr Leu Gln Lys Pro Gly Arg Ser Pro Arg Leu Leu Ile
        35                  40                  45

Tyr Asn Thr Asp Thr Leu His Thr Gly Val Pro Asp Arg Phe Ser Gly
    50                  55                  60

Ser Gly Ser Gly Thr Asp Phe Thr Leu Lys Ile Ser Arg Val Gln Thr
65                  70                  75                  80

Glu Asp Val Gly Val Tyr Phe Cys Gln His Tyr Phe His Tyr Pro Arg
                85                  90                  95

Thr Phe Gly Gln Gly Thr Lys Leu Glu Leu Lys Arg Ser Asp Ala Gln
            100                 105                 110

Pro Ser Val Phe Leu Phe Gln Pro Ser Leu Asp Glu Leu His Thr Gly
            115                 120                 125

Ser Ala Ser Ile Val Cys Ile Leu Asn Asp Phe Tyr Pro Lys Glu Val
    130                 135                 140

Asn Val Lys Trp Lys Val Asp Gly Val Val Gln Asn Lys Gly Ile Gln
145                 150                 155                 160

Glu Ser Thr Thr Glu Gln Asn Ser Lys Asp Ser Thr Tyr Ser Leu Ser
                165                 170                 175

Ser Thr Leu Thr Met Ser Ser Thr Glu Tyr Gln Ser His Glu Lys Phe
            180                 185                 190

Ser Cys Glu Val Thr His Lys Ser Leu Ala Ser Thr Leu Val Lys Ser
            195                 200                 205

Phe Gln Arg Ser Glu Cys Gln Arg Glu
    210                 215

<210> SEQ ID NO 36
<211> LENGTH: 11

-continued

<212> TYPE: PRT
<213> ORGANISM: Rattus rattus

<400> SEQUENCE: 36

Arg Ala Ser Glu Asp Ile Tyr Asn Ala Leu Ala
1               5                   10

<210> SEQ ID NO 37
<211> LENGTH: 7
<212> TYPE: PRT
<213> ORGANISM: Rattus rattus

<400> SEQUENCE: 37

Asn Thr Asp Thr Leu His Thr
1               5

<210> SEQ ID NO 38
<211> LENGTH: 9
<212> TYPE: PRT
<213> ORGANISM: Rattus rattus

<400> SEQUENCE: 38

Gln His Tyr Phe His Tyr Pro Arg Thr
1               5

<210> SEQ ID NO 39
<211> LENGTH: 5
<212> TYPE: PRT
<213> ORGANISM: Mus musculus

<400> SEQUENCE: 39

Ser Ser Trp Met Asn
1               5

<210> SEQ ID NO 40
<211> LENGTH: 17
<212> TYPE: PRT
<213> ORGANISM: Mus musculus

<400> SEQUENCE: 40

Gln Ile Tyr Pro Gly Asp Gly Asp Thr Asn Tyr Asn Gly Lys Phe Lys
1               5                   10                  15

Gly

<210> SEQ ID NO 41
<211> LENGTH: 10
<212> TYPE: PRT
<213> ORGANISM: Mus musculus

<400> SEQUENCE: 41

Ala Arg His Tyr Asp Gly Ser Thr Asp Tyr
1               5                   10

<210> SEQ ID NO 42
<211> LENGTH: 11
<212> TYPE: PRT
<213> ORGANISM: Mus musculus

<400> SEQUENCE: 42

Arg Ala Ser Glu Asn Ile Tyr Ser Asn Leu Ala
1               5                   10

<210> SEQ ID NO 43
<211> LENGTH: 7

```
<212> TYPE: PRT
<213> ORGANISM: Mus musculus

<400> SEQUENCE: 43

Ala Ala Thr Asn Leu Ala Asp
1               5

<210> SEQ ID NO 44
<211> LENGTH: 9
<212> TYPE: PRT
<213> ORGANISM: Mus musculus

<400> SEQUENCE: 44

Gln His Phe Trp Gly Thr Pro Tyr Thr
1               5

<210> SEQ ID NO 45
<211> LENGTH: 117
<212> TYPE: PRT
<213> ORGANISM: Artificial Sequence
<220> FEATURE:
<223> OTHER INFORMATION: Felinized Sequence - Variable Heavy Region
      Engineered to Have Sequences from Mus musculus and Felis

<400> SEQUENCE: 45

Gln Val Leu Leu Val Gln Ser Gly Ala Glu Val Arg Arg Pro Gly Ala
1               5                   10                  15

Ser Val Lys Ile Phe Cys Lys Ala Ser Gly Tyr Ser Phe Thr Ser Ser
                20                  25                  30

Trp Met Asn Trp Leu Arg Gln Ala Pro Ala Gln Gly Phe Glu Trp Met
            35                  40                  45

Gly Gln Ile Tyr Pro Gly Asp Gly Asp Thr Asn Tyr Asn Gly Lys Phe
        50                  55                  60

Lys Gly Arg Leu Thr Leu Thr Ala Asp Thr Ser Thr Asp Thr Ala Tyr
65                  70                  75                  80

Met Glu Leu Ser Ser Leu Arg Ser Ala Asp Thr Ala Val Tyr Tyr Cys
                85                  90                  95

Ala Arg His Tyr Asp Gly Ser Thr Asp Tyr Trp Gly His Gly Thr Ile
            100                 105                 110

Val Thr Val Ser Ser
        115

<210> SEQ ID NO 46
<211> LENGTH: 351
<212> TYPE: DNA
<213> ORGANISM: Artificial Sequence
<220> FEATURE:
<223> OTHER INFORMATION: Felinized Sequence - Variable Heavy Region
      Engineered to Have Sequences from Mus musculus and Felis

<400> SEQUENCE: 46
caggtgctgc tggtgcagag cggcgcggaa gtgcgccgcc cgggcgcgag cgtgaaaatt     60
ttttgcaaag cgagcggcta tagctttacc agcagctgga tgaactggct cgcgccaggcg    120 ccggcgcagg gctttgaatg gatgggccag atttatccgg gcgatggcga taccaactat    180
aacggcaaat ttaaaggccg cctgaccctg accgcggata ccagcaccga taccgcgtat    240
atggaactga gcagcctgcg cagcgcggat accgcggtgt attattgcgc gcgccattat    300
gatggcagca ccgattattg gggccatggc accattgtga ccgtgagcag c             351

<210> SEQ ID NO 47
```

```
<211> LENGTH: 103
<212> TYPE: PRT
<213> ORGANISM: Artificial Sequence
<220> FEATURE:
<223> OTHER INFORMATION: Felinized Sequence - Variable Light Region
      Engineered to Have Sequences from Mus musculus and Felis

<400> SEQUENCE: 47

Ala Ile Thr Met Thr Gln Ser Pro Gly Ser Leu Ala Gly Ser Pro Gly
1               5                   10                  15

Gln Gln Val Thr Met Asn Cys Arg Ala Ser Glu Asn Ile Tyr Ser Asn
            20                  25                  30

Leu Ala Trp Tyr Gln Gln Lys Pro Gly Gln His Pro Lys Leu Leu Ile
        35                  40                  45

Tyr Ala Ala Thr Asn Leu Ala Asp Gly Val Pro Asp Arg Phe Ser Gly
    50                  55                  60

Ser Gly Ser Gly Thr Asp Phe Thr Leu Thr Ile Ser Asn Leu Gln Ala
65                  70                  75                  80

Glu Asp Val Ala Ser Tyr Tyr Cys Gln His Phe Trp Gly Thr Pro Tyr
                85                  90                  95

Thr Phe Gly Gly Gly Thr Lys
                100

<210> SEQ ID NO 48
<211> LENGTH: 309
<212> TYPE: DNA
<213> ORGANISM: Artificial Sequence
<220> FEATURE:
<223> OTHER INFORMATION: Felinized Sequence - Variable Light Region
      Engineered to Have Sequences from Mus musculus and Felis

<400> SEQUENCE: 48
gcgattacca tgacccagag cccgggcagc ctggcgggca gcccgggcca gcaggtgacc      60
atgaactgcc gcgcgagcga aaacatttat agcaacctgg cgtggtatca gcagaaaccg     120
ggccagcatc cgaaactgct gatttatgcg gcgaccaacc tggcggatgg cgtgccggat     180
cgctttagcg gcagcggcag cggcaccgat tttaccctga ccattagcaa cctgcaggcg     240
gaagatgtgg cgagctatta ttgccagcat ttttggggca ccccgtatac ctttggcggc     300
ggcaccaaa                                                             309

<210> SEQ ID NO 49
<211> LENGTH: 5
<212> TYPE: PRT
<213> ORGANISM: Homo sapiens

<400> SEQUENCE: 49

Ser Asn Val Ile Ser
1               5

<210> SEQ ID NO 50
<211> LENGTH: 18
<212> TYPE: PRT
<213> ORGANISM: Homo sapiens

<400> SEQUENCE: 50

Gly Val Ile Pro Ile Val Asp Ile Ala Asn Tyr Ala Gln Arg Phe Lys
1               5                   10                  15

Gly Arg

<210> SEQ ID NO 51
```

```
<211> LENGTH: 11
<212> TYPE: PRT
<213> ORGANISM: Homo sapiens

<400> SEQUENCE: 51

Thr Leu Gly Leu Val Leu Asp Ala Met Asp Tyr
1               5                   10

<210> SEQ ID NO 52
<211> LENGTH: 10
<212> TYPE: PRT
<213> ORGANISM: Homo sapiens

<400> SEQUENCE: 52

Arg Ala Ser Gln Ser Leu Gly Ser Ser Tyr
1               5                   10

<210> SEQ ID NO 53
<211> LENGTH: 7
<212> TYPE: PRT
<213> ORGANISM: Homo sapiens

<400> SEQUENCE: 53

Gly Ala Ser Ser Arg Ala Pro
1               5

<210> SEQ ID NO 54
<211> LENGTH: 9
<212> TYPE: PRT
<213> ORGANISM: Homo sapiens

<400> SEQUENCE: 54

Gln Gln Tyr Ala Asp Ser Pro Ile Thr
1               5

<210> SEQ ID NO 55
<211> LENGTH: 120
<212> TYPE: PRT
<213> ORGANISM: Artificial Sequence
<220> FEATURE:
<223> OTHER INFORMATION: Felinized Sequence - Variable Heavy Region
      Engineered to Have Sequences from Homo sapiens and Felis

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser
        115                 120

<210> SEQ ID NO 56
```

-continued

```
<211> LENGTH: 360
<212> TYPE: DNA
<213> ORGANISM: Artificial Sequence
<220> FEATURE:
<223> OTHER INFORMATION: Felinized Sequence - Variable Heavy Region
      Engineered to Have Sequences from Homo sapiens and Felis

<400> SEQUENCE: 56
caggtgcagc tggtgcagtc cggagctgag gtgaagaagc caggctccag cgtgaaggtg      60
tcttgcaagg cttccggcta caccttctct tccaacgtga tcagctgggt gagacaggct     120
ccaggacagg gactggagtg gatgggaggc gtgatcccta tcgtggacat cgccaattac     180
gctcagaggt ttaagggccg ggtgaccatc acagctgatg agtccacaag caccacatat     240
atggagctga gctctctgcg cagcgaggac accgccgtgt actattgtgc ttctacactg     300
ggcctggtgc tggacgctat ggactattgg ggccagggca ccctggtgac agtctcgagc     360

<210> SEQ ID NO 57
<211> LENGTH: 108
<212> TYPE: PRT
<213> ORGANISM: Artificial Sequence
<220> FEATURE:
<223> OTHER INFORMATION: Felinized Sequence - Variable Light Region
      Engineered to Have Sequences from Homo sapiens and Felis

<400> SEQUENCE: 57

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Lys Leu Glu Ile Lys
            100                 105

<210> SEQ ID NO 58
<211> LENGTH: 324
<212> TYPE: DNA
<213> ORGANISM: Artificial Sequence
<220> FEATURE:
<223> OTHER INFORMATION: Felinized Sequence - Variable Light Region
      Engineered to Have Sequences from Homo sapiens and Felis

<400> SEQUENCE: 58
gagaccgtgc tgacacagtc tcctggcacc ctgagcctgt ctccaggaga gagggccaca      60
ctgtcctgca gggcttccca gagcctgggc tccagctacc tggcctggta tcagcagaag     120
ccaggccagg ctcccaggct gctgatctac ggagcctctt ccagagctcc aggcatccct     180
gaccgcttct ctggatccgg aagcggcacc gacttcaccc tgacaatcag cagactggag     240
cccgaggact cgccgtgta ctattgtcag cagtatgctg attctcctat cacatttggc      300
cagggtacca agctggagat caaa                                            324

<210> SEQ ID NO 59
<211> LENGTH: 5
```

```
<212> TYPE: PRT
<213> ORGANISM: Homo sapiens

<400> SEQUENCE: 59

Ser Asn Val Ile Ser
1               5

<210> SEQ ID NO 60
<211> LENGTH: 17
<212> TYPE: PRT
<213> ORGANISM: Homo sapiens

<400> SEQUENCE: 60

Gly Val Ile Pro Ile Val Asp Ile Ala Asn Tyr Ala Gln Arg Phe Lys
1               5                   10                  15

Gly

<210> SEQ ID NO 61
<211> LENGTH: 13
<212> TYPE: PRT
<213> ORGANISM: Homo sapiens

<400> SEQUENCE: 61

Ala Ser Thr Leu Gly Leu Val Leu Asp Ala Met Asp Tyr
1               5                   10

<210> SEQ ID NO 62
<211> LENGTH: 10
<212> TYPE: PRT
<213> ORGANISM: Homo sapiens

<400> SEQUENCE: 62

Arg Ala Ser Gln Ser Leu Gly Ser Ser Tyr
1               5                   10

<210> SEQ ID NO 63
<211> LENGTH: 7
<212> TYPE: PRT
<213> ORGANISM: Homo sapiens

<400> SEQUENCE: 63

Gly Ala Ser Ser Arg Ala Pro
1               5

<210> SEQ ID NO 64
<211> LENGTH: 9
<212> TYPE: PRT
<213> ORGANISM: Homo sapiens

<400> SEQUENCE: 64

Gln Gln Tyr Ala Asp Ser Pro Ile Thr
1               5

<210> SEQ ID NO 65
<211> LENGTH: 120
<212> TYPE: PRT
<213> ORGANISM: Artificial Sequence
<220> FEATURE:
<223> OTHER INFORMATION: Felinized Sequence - Variable Heavy Region
      Engineered to Have Sequences from Homo sapiens and Felis

<400> SEQUENCE: 65

Gln Val Leu Leu Val Gln Ser Gly Ala Asp Val Arg Lys Pro Gly Ala
1               5                   10                  15
```

-continued

```
Ser Val Lys Ile Phe Cys Lys Ala Ser Gly Tyr Thr Phe Thr Ser Asn
            20                  25                  30

Val Ile Ser Trp Val Arg Gln Thr Pro Ala Gln Gly Phe Glu Trp Met
        35                  40                  45

Gly Gly Val Ile Pro Ile Val Asp Ile Ala Asn Tyr Ala Gln Arg Phe
        50                  55                  60

Lys Gly Arg Leu Val Leu Thr Ala Asp Thr Ser Thr Asn Thr Ala Tyr
65                  70                  75                  80

Met Glu Leu Arg Ser Leu Lys Ser Ala Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Ser Leu Val Thr Val Ser Ser
        115                 120
```

```
<210> SEQ ID NO 66
<211> LENGTH: 360
<212> TYPE: DNA
<213> ORGANISM: Artificial Sequence
<220> FEATURE:
<223> OTHER INFORMATION: Felinized Sequence - Variable Heavy Region
      Engineered to Have Sequences from Homo sapiens and Felis

<400> SEQUENCE: 66
caggtgctgc tggtgcagtc tggcgccgat gtgagaaagc caggcgctag cgtgaagatc        60
ttctgcaagg cctctggcta cacctttaca tctaacgtga tctcctgggt gcgccagaca       120
ccagctcagg gattcgagtg gatgggaggc gtgatcccta tcgtggacat cgccaactac       180
gctcagaggt ttaagggccg gctggtgctg accgctgata cctccacaaa taccgcttat       240
atggagctga ggtccctgaa gagcgccgac acagccgtgt actattgtgc ctccaccctg       300
ggactggtgc tggacgctat ggattattgg ggccagggca gcctggtgac agtctcgagc       360
```

```
<210> SEQ ID NO 67
<211> LENGTH: 108
<212> TYPE: PRT
<213> ORGANISM: Artificial Sequence
<220> FEATURE:
<223> OTHER INFORMATION: Felinized Sequence - Variable Light Region
      Engineered to Have Sequences from Homo sapiens and Felis

<400> SEQUENCE: 67
```

```
Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Ser Leu Gly Ser Ser
            20                  25                  30

Tyr Leu Ala Trp Tyr Gln Gln Lys Pro Gly Lys Val Pro Lys Leu Leu
        35                  40                  45

Ile Tyr Gly Ala Ser Ser Arg Ala Pro Gly Val Pro Ser Arg Phe Ser
        50                  55                  60

Gly Ser Gly Ser Gly Thr Asp Phe Thr Leu Thr Ile Ser Ser Leu Glu
65                  70                  75                  80

Pro Glu Asp Ala Ala Thr Tyr Tyr Cys Gln Gln Tyr Ala Asp Ser Pro
                85                  90                  95

Ile Thr Phe Gly Gln Gly Thr Lys Leu Glu Ile Lys
            100                 105
```

```
<210> SEQ ID NO 68
<211> LENGTH: 324
```

<212> TYPE: DNA
<213> ORGANISM: Artificial Sequence
<220> FEATURE:
<223> OTHER INFORMATION: Felinized Sequence - Variable Light Region
     Engineered to Have Sequences from Homo sapiens and Felis

<400> SEQUENCE: 68
gagatccaga tgacccagtc tccttccagc ctgtctgcct ccccaggcga cagggtgacc        60
atcacatgcc gggccagcca gtctctgggc tcttcctacc tggcttggta tcagcagaag       120
ccaggcaagg tgcccaagct gctgatctac ggagccagct ctagagctcc aggcgtgcct       180
tcccgcttct ccggaagcgg atctggcaca gacttcaccc tgacaatctc cagcctggag       240
ccagaggacg ctgctaccta ctattgtcag cagtatgctg atagccctat cacattcggc       300
cagggtacca agctggagat caaa                                              324

<210> SEQ ID NO 69
<211> LENGTH: 5
<212> TYPE: PRT
<213> ORGANISM: Homo sapiens

<400> SEQUENCE: 69

Ser Asn Val Ile Ser
1               5

<210> SEQ ID NO 70
<211> LENGTH: 17
<212> TYPE: PRT
<213> ORGANISM: Homo sapiens

<400> SEQUENCE: 70

Gly Val Ile Pro Ile Val Asp Ile Ala Asn Tyr Ala Gln Arg Phe Lys
1               5                   10                  15

Gly

<210> SEQ ID NO 71
<211> LENGTH: 13
<212> TYPE: PRT
<213> ORGANISM: Homo sapiens

<400> SEQUENCE: 71

Ala Ser Thr Leu Gly Leu Val Leu Asp Ala Met Asp Tyr
1               5                   10

<210> SEQ ID NO 72
<211> LENGTH: 12
<212> TYPE: PRT
<213> ORGANISM: Homo sapiens

<400> SEQUENCE: 72

Arg Ala Ser Gln Ser Leu Gly Ser Ser Tyr Leu Ala
1               5                   10

<210> SEQ ID NO 73
<211> LENGTH: 7
<212> TYPE: PRT
<213> ORGANISM: Homo sapiens

<400> SEQUENCE: 73

Gly Ala Ser Ser Arg Ala Pro
1               5

<210> SEQ ID NO 74

<211> LENGTH: 9
<212> TYPE: PRT
<213> ORGANISM: Homo sapiens

<400> SEQUENCE: 74

Gln Gln Tyr Ala Asp Ser Pro Ile Thr
1               5

<210> SEQ ID NO 75
<211> LENGTH: 120
<212> TYPE: PRT
<213> ORGANISM: Artificial Sequence
<220> FEATURE:
<223> OTHER INFORMATION: Felinized Sequence - Variable Heavy Region
      Engineered to Have Sequences from Homo sapiens and Felis

<400> SEQUENCE: 75

Gln Val Leu Leu Val Gln Ser Gly Ala Glu Val Arg Thr Pro Gly Ala
1               5                   10                  15

Ser Val Lys Ile Phe Cys Lys Ala Ser Gly Tyr Gly Phe Thr Ser Asn
            20                  25                  30

Val Ile Ser Trp Val Arg Gln Ser Pro Ala Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Leu Thr Leu Thr Ala Asp Thr Ser Thr Asp Thr Ala Tyr
65                  70                  75                  80

Met Glu Leu Ser Ser Leu Arg Ser Ala Asp Thr Ala Met Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser
        115                 120

<210> SEQ ID NO 76
<211> LENGTH: 363
<212> TYPE: DNA
<213> ORGANISM: Artificial Sequence
<220> FEATURE:
<223> OTHER INFORMATION: Felinized Sequence - Variable Heavy Region
      Engineered to Have Sequences from Homo sapiens and Felis

<400> SEQUENCE: 76
caggtgctgc tggtgcagtc tggcgccgag gtgagaacac caggcgctag cgtgaagatc      60
ttctgcaagg cctctggcta cggctttacc tctaacgtga tctcctgggt cgcgcagtcc     120
ccagctcagg gactggagtg gatgggaggc gtgatcccta tcgtggacat cgccaattac     180
gctcagaggt tcaagggccg gctgaccctg acagctgaca cctccacaga taccgcttat     240
atggagctgt ccagcctgag gtccgccgat acagctatgt actattgtgc cagcaccctg     300
ggactggtgc tggacgctat ggattattgg ggccagggca cactggtgac cgtggtctcg     360
agc                                                                    363

<210> SEQ ID NO 77
<211> LENGTH: 108
<212> TYPE: PRT
<213> ORGANISM: Artificial Sequence
<220> FEATURE:
<223> OTHER INFORMATION: Felinized Sequence - Variable Light Region
      Engineered to Have Sequences from Homo sapiens and Felis

<400> SEQUENCE: 77

-continued

```
Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Ser Leu Gly Ser Ser
                20                  25                  30

Tyr Leu Ala Trp Tyr Gln Gln Lys Pro Gly Lys Val Pro Lys Leu Leu
        35                  40                  45

Ile Tyr Gly Ala Ser Ser Arg Ala Pro Gly Val Pro Ser Arg Phe Ser
    50                  55                  60

Gly Ser Gly Ser Gly Thr Asp Phe Thr Leu Thr Ile Ser Ser Leu Glu
65                  70                  75                  80

Pro Glu Asp Ala Ala Thr Tyr Tyr Cys Gln Gln Tyr Ala Asp Ser Pro
                85                  90                  95

Ile Thr Phe Gly Gln Gly Thr Lys Leu Glu Ile Lys
            100                 105
```

```
<210> SEQ ID NO 78
<211> LENGTH: 324
<212> TYPE: DNA
<213> ORGANISM: Artificial Sequence
<220> FEATURE:
<223> OTHER INFORMATION: Felinized Sequence - Variable Light Region
      Engineered to Have Sequences from Homo sapiens and Felis

<400> SEQUENCE: 78
gagatccaga tgacccagtc tccttccagc ctgtctgcct ccccaggcga cagggtgacc         60
atcacatgcc gggccagcca gtctctgggc tcttcctacc tggcttggta tcagcagaag        120
ccaggcaagg tgcccaagct gctgatctac ggagccagct ctagagctcc aggcgtgcct        180
tcccgcttct ccggaagcgg atctggcaca gacttcaccc tgacaatctc cagcctggag        240
ccagaggacg ctgctaccta ctattgtcag cagtatgctg atagccctat cacattcggc        300
cagggtacca agctggagat caaa                                              324
```

```
<210> SEQ ID NO 79
<211> LENGTH: 8
<212> TYPE: PRT
<213> ORGANISM: Homo sapiens

<400> SEQUENCE: 79

Gly Tyr Thr Phe Ser Ser Asn Val
1               5
```

```
<210> SEQ ID NO 80
<211> LENGTH: 8
<212> TYPE: PRT
<213> ORGANISM: Homo sapiens

<400> SEQUENCE: 80

Val Ile Pro Ile Val Asp Ile Ala
1               5
```

```
<210> SEQ ID NO 81
<211> LENGTH: 10
<212> TYPE: PRT
<213> ORGANISM: Homo sapiens

<400> SEQUENCE: 81

Leu Gly Leu Val Leu Asp Ala Met Asp Tyr
1               5                   10
```

```
<210> SEQ ID NO 82
<211> LENGTH: 12
<212> TYPE: PRT
<213> ORGANISM: Homo sapiens

<400> SEQUENCE: 82

Arg Ala Ser Gln Ser Leu Gly Ser Ser Tyr Leu Ala
1               5                   10

<210> SEQ ID NO 83
<211> LENGTH: 7
<212> TYPE: PRT
<213> ORGANISM: Homo sapiens

<400> SEQUENCE: 83

Gly Ala Ser Ser Arg Ala Pro
1               5

<210> SEQ ID NO 84
<211> LENGTH: 9
<212> TYPE: PRT
<213> ORGANISM: Homo sapiens

<400> SEQUENCE: 84

Gln Gln Tyr Ala Asp Ser Pro Ile Thr
1               5

<210> SEQ ID NO 85
<211> LENGTH: 120
<212> TYPE: PRT
<213> ORGANISM: Artificial Sequence
<220> FEATURE:
<223> OTHER INFORMATION: Felinized Sequence - Variable Heavy Region
      Engineered to Have Sequences from Homo sapiens and Felis

<400> SEQUENCE: 85

Gln Val Leu Leu Val Gln Ser Gly Ala Asp Val Arg Lys Pro Gly Ala
1               5                   10                  15

Ser Val Lys Ile Phe Cys Lys Ala Ser Gly Tyr Thr Phe Ser Ser Asn
            20                  25                  30

Val Met His Trp Val Arg Gln Thr Pro Ala Gln Gly Phe Glu Trp Met
        35                  40                  45

Gly Ser Val Ile Pro Ile Val Asp Ile Ala Thr Tyr Ala Arg Arg Phe
    50                  55                  60

Gln Gly Arg Leu Val Leu Thr Ala Asp Thr Ser Thr Asn Thr Ala Tyr
65                  70                  75                  80

Met Glu Leu Arg Ser Leu Lys Ser Ala Asp Thr Ala Val Tyr Tyr Cys
                85                  90                  95

Ala Arg Thr Leu Gly Leu Val Leu Asp Ala Met Asp Tyr Trp Gly Gln
                100                 105                 110

Gly Ser Leu Val Thr Val Ser Ser
        115                 120

<210> SEQ ID NO 86
<211> LENGTH: 360
<212> TYPE: DNA
<213> ORGANISM: Artificial Sequence
<220> FEATURE:
<223> OTHER INFORMATION: Felinized Sequence - Variable Heavy Region
      Engineered to Have Sequences from Homo sapiens and Felis

<400> SEQUENCE: 86
caggtgctgc tggtgcagtc tggcgccgat gtgaggaagc caggcgctag cgtgaagatc      60
```

-continued

```
ttctgcaagg cctctggcta cacattttcc agcaacgtga tgcactgggt gagacagacc          120
cccgctcagg gcttcgagtg gatgggctcc gtgatcccta tcgtggacat cgccacatac          180
gctaggcggt ttcagggcag gctggtgctg accgccgata ccagcacaaa taccgcttat          240
atggagctga atctctgaa gtccgccgac acagccgtgt actattgtgc tcgcaccctg           300
ggactggtgc tggacgctat ggattattgg ggccagggct ccctggtgac agtctcgagc          360
```

```
<210> SEQ ID NO 87
<211> LENGTH: 108
<212> TYPE: PRT
<213> ORGANISM: Artificial Sequence
<220> FEATURE:
<223> OTHER INFORMATION: Felinized Sequence - Variable Light Region
      Engineered to Have Sequences from Homo sapiens and Felis

<400> SEQUENCE: 87

Glu Ile Gln Met Thr Gln Ser Pro Ser Ser Leu Ser Ala Ser Pro Gly
1               5                   10                  15

Asp Arg Val Thr Ile Thr Cys Arg Ala Ser Gln Ser Leu Gly Ser Ser
            20                  25                  30

Tyr Leu Ala Trp Tyr Gln Gln Lys Pro Gly Lys Val Pro Lys Leu Leu
        35                  40                  45

Ile Tyr Gly Ala Ser Ser Arg Ala Pro Gly Val Pro Ser Arg Phe Ser
    50                  55                  60

Gly Ser Gly Ser Gly Thr Asp Phe Thr Leu Thr Ile Ser Ser Leu Glu
65                  70                  75                  80

Pro Glu Asp Ala Ala Thr Tyr Tyr Cys Gln Gln Tyr Ala Asp Ser Pro
                85                  90                  95

Ile Thr Phe Gly Gln Gly Thr Lys Leu Glu Ile Lys
            100                 105
```

```
<210> SEQ ID NO 88
<211> LENGTH: 324
<212> TYPE: DNA
<213> ORGANISM: Artificial Sequence
<220> FEATURE:
<223> OTHER INFORMATION: Felinized Sequence - Variable Light Region
      Engineered to Have Sequences from Homo sapiens and Felis

<400> SEQUENCE: 88
gagatccaga tgacccagtc tccttccagc ctgtctgcct ccccaggcga cagggtgacc            60
atcacatgcc gggccagcca gtctctgggc tcttcctacc tggcttggta tcagcagaag          120
ccaggcaagg tgcccaagct gctgatctac ggagccagct ctagagctcc aggcgtgcct          180
tcccgcttct ccggaagcgg atctggcaca gacttcaccc tgacaatctc cagcctggag          240
ccagaggacg ctgctaccta ctattgtcag cagtatgctg atagccctat cacattcggc          300
cagggtacca agctggagat caaa                                                  324
```

```
<210> SEQ ID NO 89
<211> LENGTH: 8
<212> TYPE: PRT
<213> ORGANISM: Homo sapiens

<400> SEQUENCE: 89

Gly Tyr Thr Phe Ser Ser Asn Val
1               5
```

```
<210> SEQ ID NO 90
```

```
<211> LENGTH: 8
<212> TYPE: PRT
<213> ORGANISM: Homo sapiens

<400> SEQUENCE: 90

Val Ile Pro Ile Val Asp Ile Ala
1               5

<210> SEQ ID NO 91
<211> LENGTH: 8
<212> TYPE: PRT
<213> ORGANISM: Homo sapiens

<400> SEQUENCE: 91

Leu Val Leu Asp Ala Met Asp Tyr
1               5

<210> SEQ ID NO 92
<211> LENGTH: 12
<212> TYPE: PRT
<213> ORGANISM: Homo sapiens

<400> SEQUENCE: 92

Arg Ala Ser Gln Ser Leu Gly Ser Ser Tyr Leu Ala
1               5                   10

<210> SEQ ID NO 93
<211> LENGTH: 7
<212> TYPE: PRT
<213> ORGANISM: Homo sapiens

<400> SEQUENCE: 93

Gly Ala Ser Ser Arg Ala Pro
1               5

<210> SEQ ID NO 94
<211> LENGTH: 9
<212> TYPE: PRT
<213> ORGANISM: Homo sapiens

<400> SEQUENCE: 94

Gln Gln Tyr Ala Asp Ser Pro Ile Thr
1               5

<210> SEQ ID NO 95
<211> LENGTH: 120
<212> TYPE: PRT
<213> ORGANISM: Artificial Sequence
<220> FEATURE:
<223> OTHER INFORMATION: Felinized Sequence - Variable Heavy Region
      Engineered to Have Sequences from Homo sapiens and Felis

<400> SEQUENCE: 95

Asp Val Gln Leu Val Glu Ser Gly Gly Asp Leu Val Lys Pro Gly Gly
1               5                   10                  15

Ser Leu Arg Leu Thr Cys Val Ala Ser Gly Tyr Thr Phe Ser Ser Asn
            20                  25                  30

Val Met His Trp Val Arg Gln Ala Pro Gly Lys Gly Leu Gln Trp Val
        35                  40                  45

Ala Tyr Val Ile Pro Ile Val Asp Ile Ala Tyr Tyr Ala Asp Ser Val
    50                  55                  60

Lys Gly Arg Phe Thr Ile Ser Ile Asp Asn Ser Lys Asn Thr Leu Tyr
65                  70                  75                  80
```

```
Leu Gln Met Asn Ser Leu Lys Thr Glu Asp Thr Ala Thr Tyr Tyr Cys
                85              90              95

Ala Arg Thr Leu Gly Leu Val Leu Asp Ala Met Asp Tyr Trp Gly Gln
        100             105             110

Gly Thr Leu Val Thr Val Ser Ser
        115             120

<210> SEQ ID NO 96
<211> LENGTH: 360
<212> TYPE: DNA
<213> ORGANISM: Artificial Sequence
<220> FEATURE:
<223> OTHER INFORMATION: Felinized Sequence - Variable Heavy Region
      Engineered to Have Sequences from Homo sapiens and Felis

<400> SEQUENCE: 96
gacgtgcagc tggtggagtc tggaggcgat ctggtgaagc caggaggcag cctgaggctg     60
acctgcgtgg cttctggcta cacattctcc agcaacgtga tgcactgggt gcggcaggct    120
ccaggcaagg gactgcagtg ggtggcttat gtgatcccta tcgtggacat cgcctactat    180
gctgattccg tgaagggcag gttcaccatc tctatcgaca actccaagaa tacactgtac    240
ctgcagatga atagcctgaa gaccgaggat accgccacat actattgtgc tcgcacactg    300
ggcctggtgc tggacgctat ggattattgg ggccagggca ccctggtgac agtctcgagc    360

<210> SEQ ID NO 97
<211> LENGTH: 108
<212> TYPE: PRT
<213> ORGANISM: Artificial Sequence
<220> FEATURE:
<223> OTHER INFORMATION: Felinized Sequence - Variable Light Region
      Engineered to Have Sequences from Homo sapiens and Felis

<400> SEQUENCE: 97

Glu Ile Gln Met Thr Gln Ser Pro Ser Ser Leu Ser Ala Ser Pro Gly
1               5               10              15

Asp Arg Val Thr Ile Thr Cys Arg Ala Ser Gln Ser Leu Gly Ser Ser
            20              25              30

Tyr Leu Ala Trp Tyr Gln Gln Lys Pro Gly Lys Val Pro Lys Leu Leu
        35              40              45

Ile Tyr Gly Ala Ser Ser Arg Ala Pro Gly Val Pro Ser Arg Phe Ser
    50              55              60

Gly Ser Gly Ser Gly Thr Asp Phe Thr Leu Thr Ile Ser Ser Leu Glu
65              70              75              80

Pro Glu Asp Ala Ala Thr Tyr Tyr Cys Gln Gln Tyr Ala Asp Ser Pro
                85              90              95

Ile Thr Phe Gly Gln Gly Thr Lys Leu Glu Ile Lys
            100             105

<210> SEQ ID NO 98
<211> LENGTH: 324
<212> TYPE: DNA
<213> ORGANISM: Artificial Sequence
<220> FEATURE:
<223> OTHER INFORMATION: Felinized Sequence - Variable Light Region
      Engineered to Have Sequences from Homo sapiens and Felis

<400> SEQUENCE: 98
gagatccaga tgacccagtc tccttccagc ctgtctgcct ccccaggcga cagggtgacc     60
atcacatgcc gggccagcca gtctctgggc tcttcctacc tggcttggta tcagcagaag    120
```

-continued

```
ccaggcaagg tgcccaagct gctgatctac ggagccagct ctagagctcc aggcgtgcct    180
tcccgcttct ccggaagcgg atctggcaca gacttcaccc tgacaatctc cagcctggag    240
ccagaggacg ctgctaccta ctattgtcag cagtatgctg atagccctat cacattcggc    300
cagggtacca agctggagat caaa                                           324
```

```
<210> SEQ ID NO 99
<211> LENGTH: 8
<212> TYPE: PRT
<213> ORGANISM: Homo sapiens

<400> SEQUENCE: 99

Gly Tyr Thr Phe Ser Ser Asn Val
1               5

<210> SEQ ID NO 100
<211> LENGTH: 8
<212> TYPE: PRT
<213> ORGANISM: Homo sapiens

<400> SEQUENCE: 100

Val Ile Pro Ile Val Asp Ile Ala
1               5

<210> SEQ ID NO 101
<211> LENGTH: 10
<212> TYPE: PRT
<213> ORGANISM: Homo sapiens

<400> SEQUENCE: 101

Leu Gly Leu Val Leu Asp Ala Met Asp Tyr
1               5                   10

<210> SEQ ID NO 102
<211> LENGTH: 12
<212> TYPE: PRT
<213> ORGANISM: Homo sapiens

<400> SEQUENCE: 102

Arg Ala Ser Gln Ser Leu Gly Ser Ser Tyr Leu Ala
1               5                   10

<210> SEQ ID NO 103
<211> LENGTH: 7
<212> TYPE: PRT
<213> ORGANISM: Homo sapiens

<400> SEQUENCE: 103

Gly Ala Ser Ser Arg Ala Pro
1               5

<210> SEQ ID NO 104
<211> LENGTH: 9
<212> TYPE: PRT
<213> ORGANISM: Homo sapiens

<400> SEQUENCE: 104

Gln Gln Tyr Ala Asp Ser Pro Ile Thr
1               5

<210> SEQ ID NO 105
<211> LENGTH: 120
<212> TYPE: PRT
<213> ORGANISM: Artificial Sequence
```

<220> FEATURE:
<223> OTHER INFORMATION: Felinized Sequence - Variable Heavy Region
       Engineered to Have Sequences from Homo sapiens and Felis

<400> SEQUENCE: 105

```
Gln Val Leu Leu Val Gln Ser Gly Ala Asp Val Arg Lys Pro Gly Ala
1               5                   10                  15

Ser Val Lys Ile Phe Cys Lys Ala Ser Gly Tyr Thr Phe Ser Ser Asn
            20                  25                  30

Val Met His Trp Val Arg Gln Thr Pro Ala Gln Gly Phe Glu Trp Met
        35                  40                  45

Gly Ser Val Ile Pro Ile Val Asp Ile Ala Thr Tyr Ala Arg Arg Phe
    50                  55                  60

Gln Gly Arg Leu Val Leu Thr Ala Asp Thr Ser Thr Asn Thr Ala Tyr
65                  70                  75                  80

Met Glu Leu Arg Ser Leu Lys Ser Ala Asp Thr Ala Val Tyr Tyr Cys
                85                  90                  95

Ala Arg Thr Leu Gly Leu Val Leu Asp Ala Met Asp Tyr Trp Gly Gln
            100                 105                 110

Gly Ser Leu Val Thr Val Ser Ser
            115                 120
```

<210> SEQ ID NO 106
<211> LENGTH: 360
<212> TYPE: DNA
<213> ORGANISM: Artificial Sequence
<220> FEATURE:
<223> OTHER INFORMATION: Felinized Sequence - Variable Heavy Region
       Engineered to Have Sequences from Homo sapiens and Felis

<400> SEQUENCE: 106

```
caggtgctgc tggtgcagtc tggcgccgat gtgaggaagc caggcgctag cgtgaagatc      60
ttctgcaagg cctctggcta cacatttttcc agcaacgtga tgcactgggt gagacagacc     120
cccgctcagg gcttcgagtg gatgggctcc gtgatcccta tcgtggacat cgccacatac     180
gctaggcggt ttcagggcag gctggtgctg accgccgata ccagcacaaa taccgcttat     240
atggagctga gatctctgaa gtccgccgac acagccgtgt actattgtgc tcgcaccctg     300
ggactggtgc tggacgctat ggattattgg ggccagggct ccctggtgac agtctcgagc     360
```

<210> SEQ ID NO 107
<211> LENGTH: 107
<212> TYPE: PRT
<213> ORGANISM: Artificial Sequence
<220> FEATURE:
<223> OTHER INFORMATION: Felinized Sequence - Variable Light Region
       Engineered to Have Sequences from Homo sapiens and Felis

<400> SEQUENCE: 107

```
Asp Ile Val Leu Thr Gln Pro Pro Ser Leu Ser Val Asn Leu Gly Gln
1               5                   10                  15

Thr Ala Arg Ile Thr Cys Arg Ala Ser Gln Ser Leu Gly Ser Ser Tyr
            20                  25                  30

Leu Ala Trp Tyr Gln Gln Lys Pro Gly Gln Ala Pro Lys Leu Val Thr
        35                  40                  45

Tyr Gly Ala Ser Ser Arg Ala Pro Gly Ile Pro Asp Arg Phe Ser Gly
    50                  55                  60

Thr Asn Ser Gly Ile Thr Ala Thr Leu Thr Ile Ser Gly Ala Arg Ala
65                  70                  75                  80
```

```
Glu Asp Glu Ala Asp Tyr Tyr Cys Gln Gln Tyr Ala Asp Ser Pro Ile
                85                  90                  95

Thr Phe Gly Gln Gly Thr Lys Leu Glu Ile Lys
            100                 105

<210> SEQ ID NO 108
<211> LENGTH: 321
<212> TYPE: DNA
<213> ORGANISM: Artificial Sequence
<220> FEATURE:
<223> OTHER INFORMATION: Felinized Sequence - Variable Light Region
      Engineered to Have Sequences from Homo sapiens and Felis

<400> SEQUENCE: 108
gacatcgtgc tgacacagcc ccctagcctg tctgtgaacc tgggacagac agctaggatc      60
acctgcaggg cttcccagag cctgggctcc agctacctgg cctggtatca gcagaagcct     120
ggccaggctc caaagctggt gacatacggc gcctcttcca gagctccagg catccccgac     180
cgcttctctg gcaccaattc cggcatcacc gccacactga ccatcagcgg agccagggct     240
gaggacgagg ctgattacta ttgtcagcag tatgctgatt ctcccatcac ctttggccag     300
ggtaccaagc tggagatcaa a                                               321

<210> SEQ ID NO 109
<211> LENGTH: 8
<212> TYPE: PRT
<213> ORGANISM: Homo sapiens

<400> SEQUENCE: 109

Gly Tyr Thr Phe Ser Ser Asn Val
1               5

<210> SEQ ID NO 110
<211> LENGTH: 8
<212> TYPE: PRT
<213> ORGANISM: Homo sapiens

<400> SEQUENCE: 110

Val Ile Pro Ile Val Asp Ile Ala
1               5

<210> SEQ ID NO 111
<211> LENGTH: 8
<212> TYPE: PRT
<213> ORGANISM: Homo sapiens

<400> SEQUENCE: 111

Leu Val Leu Asp Ala Met Asp Tyr
1               5

<210> SEQ ID NO 112
<211> LENGTH: 12
<212> TYPE: PRT
<213> ORGANISM: Homo sapiens

<400> SEQUENCE: 112

Arg Ala Ser Gln Ser Leu Gly Ser Ser Tyr Leu Ala
1               5                   10

<210> SEQ ID NO 113
<211> LENGTH: 7
<212> TYPE: PRT
<213> ORGANISM: Homo sapiens
```

<400> SEQUENCE: 113

Gly Ala Ser Ser Arg Ala Pro
1               5

<210> SEQ ID NO 114
<211> LENGTH: 9
<212> TYPE: PRT
<213> ORGANISM: Homo sapiens

<400> SEQUENCE: 114

Gln Gln Tyr Ala Asp Ser Pro Ile Thr
1               5

<210> SEQ ID NO 115
<211> LENGTH: 120
<212> TYPE: PRT
<213> ORGANISM: Artificial Sequence
<220> FEATURE:
<223> OTHER INFORMATION: Felinized Sequence - Variable Heavy Region
      Engineered to Have Sequences from Homo sapiens and Felis

<400> SEQUENCE: 115

Asp Val Gln Leu Val Glu Ser Gly Gly Asp Leu Val Lys Pro Gly Gly
1               5                   10                  15

Ser Leu Arg Leu Thr Cys Val Ala Ser Gly Tyr Thr Phe Ser Ser Asn
            20                  25                  30

Val Met His Trp Val Arg Gln Ala Pro Gly Lys Gly Leu Gln Trp Val
        35                  40                  45

Ala Tyr Val Ile Pro Ile Val Asp Ile Ala Tyr Ala Asp Ser Val
    50                  55                  60

Lys Gly Arg Phe Thr Ile Ser Ile Asp Asn Ser Lys Asn Thr Leu Tyr
65                  70                  75                  80

Leu Gln Met Asn Ser Leu Lys Thr Glu Asp Thr Ala Thr Tyr Tyr Cys
            85                  90                  95

Ala Arg Thr Leu Gly Leu Val Leu Asp Ala Met Asp Tyr Trp Gly Gln
            100                 105                 110

Gly Thr Leu Val Thr Val Ser Ser
        115                 120

<210> SEQ ID NO 116
<211> LENGTH: 360
<212> TYPE: DNA
<213> ORGANISM: Artificial Sequence
<220> FEATURE:
<223> OTHER INFORMATION: Felinized Sequence - Variable Heavy Region
      Engineered to Have Sequences from Homo sapiens and Felis

<400> SEQUENCE: 116
gacgtgcagc tggtggagtc tggaggcgat ctggtgaagc aggaggcag cctgaggctg        60 acctgcgtgg cttctggcta cacattctcc agcaacgtga tgcactgggt gcggcaggct       120
ccaggcaagg gactgcagtg ggtggcttat gtgatcccta tcgtggacat cgcctactat       180
gctgattccg tgaagggcag gttcaccatc tctatcgaca actccaagaa tacactgtac       240
ctgcagatga atagcctgaa gaccgaggat accgccacat actattgtgc tcgcacactg       300
ggcctggtgc tggacgctat ggattattgg ggccagggca ccctggtgac agtctcgagc       360

<210> SEQ ID NO 117
<211> LENGTH: 107
<212> TYPE: PRT
<213> ORGANISM: Artificial Sequence -continued

```
<220> FEATURE:
<223> OTHER INFORMATION: Felinized Sequence - Variable Light Region
      Engineered to Have Sequences from Homo sapiens and Felis

<400> SEQUENCE: 117

Asp Ile Val Leu Thr Gln Pro Pro Ser Leu Ser Val Asn Leu Gly Gln
1               5                   10                  15

Thr Ala Arg Ile Thr Cys Arg Ala Ser Gln Ser Leu Gly Ser Ser Tyr
            20                  25                  30

Leu Ala Trp Tyr Gln Gln Lys Pro Gly Gln Ala Pro Lys Leu Val Thr
        35                  40                  45

Tyr Gly Ala Ser Ser Arg Ala Pro Gly Ile Pro Asp Arg Phe Ser Gly
    50                  55                  60

Thr Asn Ser Gly Ile Thr Ala Thr Leu Thr Ile Ser Gly Ala Arg Ala
65                  70                  75                  80

Glu Asp Glu Ala Asp Tyr Tyr Cys Gln Gln Tyr Ala Asp Ser Pro Ile
                85                  90                  95

Thr Phe Gly Gln Gly Thr Lys Leu Glu Ile Lys
            100                 105

<210> SEQ ID NO 118
<211> LENGTH: 321
<212> TYPE: DNA
<213> ORGANISM: Artificial Sequence
<220> FEATURE:
<223> OTHER INFORMATION: Felinized Sequence - Variable Light Region
      Engineered to Have Sequences from Homo sapiens and Felis

<400> SEQUENCE: 118
gacatcgtgc tgacacagcc ccctagcctg tctgtgaacc tgggacagac agctaggatc       60
acctgcaggg cttcccagag cctgggctcc agctacctgg cctggtatca gcagaagcct      120
ggccaggctc caaagctggt gacatacggc gcctcttcca gagctccagg catccccgac      180
cgcttctctg gcaccaattc cggcatcacc gccacactga ccatcagcgg agccagggct      240
gaggacgagg ctgattacta ttgtcagcag tatgctgatt ctcccatcac ctttggccag      300
ggtaccaagc tggagatcaa a                                                321

<210> SEQ ID NO 119
<211> LENGTH: 5
<212> TYPE: PRT
<213> ORGANISM: Homo sapiens

<400> SEQUENCE: 119

Ser Asn Val Ile Ser
1               5

<210> SEQ ID NO 120
<211> LENGTH: 17
<212> TYPE: PRT
<213> ORGANISM: Homo sapiens

<400> SEQUENCE: 120

Gly Val Ile Pro Ile Val Asp Ile Ala Asn Tyr Ala Gln Arg Phe Lys
1               5                   10                  15

Gly

<210> SEQ ID NO 121
<211> LENGTH: 13
<212> TYPE: PRT
<213> ORGANISM: Homo sapiens
```

<400> SEQUENCE: 121

Ala Ser Thr Leu Gly Leu Val Leu Asp Ala Met Asp Tyr
1               5                   10

<210> SEQ ID NO 122
<211> LENGTH: 12
<212> TYPE: PRT
<213> ORGANISM: Homo sapiens

<400> SEQUENCE: 122

Arg Ala Ser Gln Ser Leu Gly Ser Ser Tyr Leu Ala
1               5                   10

<210> SEQ ID NO 123
<211> LENGTH: 7
<212> TYPE: PRT
<213> ORGANISM: Homo sapiens

<400> SEQUENCE: 123

Gly Ala Ser Ser Arg Ala Pro
1               5

<210> SEQ ID NO 124
<211> LENGTH: 9
<212> TYPE: PRT
<213> ORGANISM: Homo sapiens

<400> SEQUENCE: 124

Gln Gln Tyr Ala Asp Ser Pro Ile Thr
1               5

<210> SEQ ID NO 125
<211> LENGTH: 120
<212> TYPE: PRT
<213> ORGANISM: Artificial Sequence
<220> FEATURE:
<223> OTHER INFORMATION: Felinized Sequence - Variable Heavy Region
      Engineered to Have Sequences from Homo sapiens and Felis

<400> SEQUENCE: 125

Gln Val Leu Leu Val Gln Ser Gly Ala Asp Val Arg Lys Pro Gly Ala
1               5                   10                  15

Ser Val Lys Ile Phe Cys Lys Ala Ser Gly Tyr Thr Phe Thr Ser Asn
            20                  25                  30

Val Ile Ser Trp Val Arg Gln Thr Pro Ala Gln Gly Phe Glu Trp Met
        35                  40                  45

Gly Gly Val Ile Pro Ile Val Asp Ile Ala Asn Tyr Ala Gln Arg Phe
    50                  55                  60

Lys Gly Arg Leu Val Leu Thr Ala Asp Thr Ser Thr Asn Thr Ala Tyr
65                  70                  75                  80

Met Glu Leu Arg Ser Leu Lys Ser Ala Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Ser Leu Val Thr Val Ser Ser
        115                 120

<210> SEQ ID NO 126
<211> LENGTH: 360
<212> TYPE: DNA
<213> ORGANISM: Artificial Sequence

```
<220> FEATURE:
<223> OTHER INFORMATION: Felinized Sequence - Variable Heavy Region
     Engineered to Have Sequences from Homo sapiens and Felis

<400> SEQUENCE: 126
caggtgctgc tggtgcagtc tggcgccgat gtgagaaagc caggcgctag cgtgaagatc      60
ttctgcaagg cctctggcta cacctttaca tctaacgtga tctcctgggt gcgccagaca     120
ccagctcagg gattcgagtg gatgggaggc gtgatcccta tcgtggacat cgccaactac     180
gctcagaggt ttaagggccg gctggtgctg accgctgata cctccacaaa taccgcttat     240
atggagctga ggtccctgaa gagcgccgac acagccgtgt actattgtgc ctccaccctg     300
ggactggtgc tggacgctat ggattattgg ggccagggca gcctggtgac agtctcgagc     360

<210> SEQ ID NO 127
<211> LENGTH: 108
<212> TYPE: PRT
<213> ORGANISM: Artificial Sequence
<220> FEATURE:
<223> OTHER INFORMATION: Felinized Sequence - Variable Light Region
     Engineered to Have Sequences from Homo sapiens and Felis

<400> SEQUENCE: 127

Asp Ile Val Met Thr Gln Ser Pro Gly Ser Leu Ala Gly Ser Pro Gly
1               5                   10                  15

Gln Gln Val Thr Met Asn Cys Arg Ala Ser Gln Ser Leu Gly Ser Ser
            20                  25                  30

Tyr Leu Ala Trp Tyr Gln Gln Lys Pro Gly Gln His Pro Glu Leu Leu
        35                  40                  45

Ile Tyr Gly Ala Ser Ser Arg Ala Pro Gly Val Pro Asp Arg Phe Ser
    50                  55                  60

Gly Ser Gly Ser Gly Thr Asp Phe Thr Leu Thr Ile Ser Asn Leu Gln
65                  70                  75                  80

Ala Glu Asp Val Ala Asn Tyr Tyr Cys Gln Gln Tyr Ala Asp Ser Pro
                85                  90                  95

Ile Thr Phe Gly Gln Gly Thr Lys Leu Glu Ile Lys
            100                 105

<210> SEQ ID NO 128
<211> LENGTH: 324
<212> TYPE: DNA
<213> ORGANISM: Artificial Sequence
<220> FEATURE:
<223> OTHER INFORMATION: Felinized Sequence - Variable Light Region
     Engineered to Have Sequences from Homo sapiens and Felis

<400> SEQUENCE: 128
gacatcgtga tgacccagtc ccctggcagc ctggctggaa gcccaggaca gcaggtgaca      60
atgaactgca gggccagcca gtctctgggc tccagctacc tggcttggta tcagcagaag     120
ccaggccagc accccgagct gctgatctac ggagcctctt ccagggctcc aggcgtgcct     180
gaccggttct ccggaagcgg atctggcacc gacttcaccc tgacaatctc taacctgcag     240
gccgaggacg tggctaatta ctattgtcag cagtatgctg attcccccat cacattcggc     300
cagggtacca agctggagat caaa                                            324

<210> SEQ ID NO 129
<211> LENGTH: 8
<212> TYPE: PRT
<213> ORGANISM: Homo sapiens
```

-continued

```
<400> SEQUENCE: 129

Gly Tyr Thr Phe Ser Ser Asn Val
1               5

<210> SEQ ID NO 130
<211> LENGTH: 8
<212> TYPE: PRT
<213> ORGANISM: Homo sapiens

<400> SEQUENCE: 130

Val Ile Pro Ile Val Asp Ile Ala
1               5

<210> SEQ ID NO 131
<211> LENGTH: 8
<212> TYPE: PRT
<213> ORGANISM: Homo sapiens

<400> SEQUENCE: 131

Leu Val Leu Asp Ala Met Asp Tyr
1               5

<210> SEQ ID NO 132
<211> LENGTH: 12
<212> TYPE: PRT
<213> ORGANISM: Homo sapiens

<400> SEQUENCE: 132

Arg Ala Ser Gln Ser Leu Gly Ser Ser Tyr Leu Ala
1               5                   10

<210> SEQ ID NO 133
<211> LENGTH: 7
<212> TYPE: PRT
<213> ORGANISM: Homo sapiens

<400> SEQUENCE: 133

Gly Ala Ser Ser Arg Ala Pro
1               5

<210> SEQ ID NO 134
<211> LENGTH: 9
<212> TYPE: PRT
<213> ORGANISM: Homo sapiens

<400> SEQUENCE: 134

Gln Gln Tyr Ala Asp Ser Pro Ile Thr
1               5

<210> SEQ ID NO 135
<211> LENGTH: 120
<212> TYPE: PRT
<213> ORGANISM: Artificial Sequence
<220> FEATURE:
<223> OTHER INFORMATION: Felinized Sequence - Variable Heavy Region
      Engineered to Have Sequences from Homo sapiens and Felis

<400> SEQUENCE: 135

Asp Val Gln Leu Val Glu Ser Gly Gly Asp Leu Val Lys Pro Gly Gly
1               5                   10                  15

Ser Leu Arg Leu Thr Cys Val Ala Ser Gly Tyr Thr Phe Ser Ser Asn
            20                  25                  30

Val Met His Trp Val Arg Gln Ala Pro Gly Lys Gly Leu Gln Trp Val
        35                  40                  45
```

-continued

```
Ala Tyr Val Ile Pro Ile Val Asp Ile Ala Tyr Tyr Ala Asp Ser Val
    50                  55                  60

Lys Gly Arg Phe Thr Ile Ser Ile Asp Asn Ser Lys Asn Thr Leu Tyr
65                  70                  75                  80

Leu Gln Met Asn Ser Leu Lys Thr Glu Asp Thr Ala Thr Tyr Tyr Cys
                85                  90                  95

Ala Arg Thr Leu Gly Leu Val Leu Asp Ala Met Asp Tyr Trp Gly Gln
            100                 105                 110

Gly Thr Leu Val Thr Val Ser Ser
        115                 120

<210> SEQ ID NO 136
<211> LENGTH: 360
<212> TYPE: DNA
<213> ORGANISM: Artificial Sequence
<220> FEATURE:
<223> OTHER INFORMATION: Felinized Sequence - Variable Heavy Region
      Engineered to Have Sequences from Homo sapiens and Felis

<400> SEQUENCE: 136
gacgtgcagc tggtggagtc tggaggcgat ctggtgaagc caggaggcag cctgaggctg      60
acctgcgtgg cttctggcta cacattctcc agcaacgtga tgcactgggt gcggcaggct     120
ccaggcaagg gactgcagtg ggtggcttat gtgatcccta tcgtggacat cgcctactat     180
gctgattccg tgaagggcag gttcaccatc tctatcgaca actccaagaa tacactgtac     240
ctgcagatga atagcctgaa gaccgaggat accgccacat actattgtgc tcgcacactg     300
ggcctggtgc tggacgctat ggattattgg ggccagggca ccctggtgac agtctcgagc     360

<210> SEQ ID NO 137
<211> LENGTH: 108
<212> TYPE: PRT
<213> ORGANISM: Artificial Sequence
<220> FEATURE:
<223> OTHER INFORMATION: Felinized Sequence - Variable Light Region
      Engineered to Have Sequences from Homo sapiens and Felis

<400> SEQUENCE: 137

Asp Ile Val Met Thr Gln Ser Pro Gly Ser Leu Ala Gly Ser Pro Gly
1               5                  10                  15

Gln Gln Val Thr Met Asn Cys Arg Ala Ser Gln Ser Leu Gly Ser Ser
            20                  25                  30

Tyr Leu Ala Trp Tyr Gln Gln Lys Pro Gly Gln His Pro Glu Leu Leu
        35                  40                  45

Ile Tyr Gly Ala Ser Ser Arg Ala Pro Gly Val Pro Asp Arg Phe Ser
    50                  55                  60

Gly Ser Gly Ser Gly Thr Asp Phe Thr Leu Thr Ile Ser Asn Leu Gln
65                  70                  75                  80

Ala Glu Asp Val Ala Asn Tyr Tyr Cys Gln Gln Tyr Ala Asp Ser Pro
                85                  90                  95

Ile Thr Phe Gly Gln Gly Thr Lys Leu Glu Ile Lys
            100                 105

<210> SEQ ID NO 138
<211> LENGTH: 324
<212> TYPE: DNA
<213> ORGANISM: Artificial Sequence
<220> FEATURE:
<223> OTHER INFORMATION: Felinized Sequence - Variable Light Region
      Engineered to Have Sequences from Homo sapiens and Felis
```

-continued

```
<400> SEQUENCE: 138
gacatcgtga tgacccagtc ccctggcagc ctggctggaa gcccaggaca gcaggtgaca        60
atgaactgca gggccagcca gtctctgggc tccagctacc tggcttggta tcagcagaag       120
ccaggccagc accccgagct gctgatctac ggagcctctt ccagggctcc aggcgtgcct       180
gaccggttct ccggaagcgg atctggcacc gacttcaccc tgacaatctc taacctgcag       240
gccgaggacg tggctaatta ctattgtcag cagtatgctg attcccccat cacattcggc       300
cagggtacca agctggagat caaa                                              324
```

FELINE ANTIBODY VARIANTS

CROSS-REFERENCE TO RELATED APPLICATIONS

This application is a national phase application of PCT international patent application PCT/US2021/052579, filed Sep. 29, 2021, which claims priority to and the benefit of U.S. Provisional Patent Application 63/084,693, filed Sep. 29, 2020, both of which are incorporated by reference herein in their entirety.

FIELD OF THE INVENTION

The invention relates generally to feline antibody variants and uses thereof. Specifically, the invention relates to a mutation in the Fc constant region of feline antibody for improving half-life and other characteristics.

BACKGROUND OF THE INVENTION

Feline IgG monoclonal antibodies (mAbs) are being developed as effective therapeutics in veterinary medicine. Several years ago, feline IgG subclasses were identified and characterized (Strietzel et al., 2014, *Vet Immunol Immunopathol., vol.* 158(3-4), pages 214-223). However, not much work has been done on extending the half-life of feline IgGs.

Through a recycling mechanism, the neonatal Fc receptor (FcRn) prolongs the half-life of an IgG in a pH-dependent interaction with its fragment crystallizable (Fc) region. Specifically, the Fc region spanning the interface of CH2 and CH3 domains interacts with the FcRn on the surface of cells to regulate IgG homeostasis. This interaction is favored by an acidic interaction after IgG pinocytosis and thus IgG is protected from degradation. The endocytosed IgG is then recycled back to the cell surface and released into the blood stream at an alkaline pH thereby maintaining sufficient serum IgG for proper function. Accordingly, the pharmacokinetic profile of IgGs depend on to the structural and functional properties of their Fc regions.

Three feline IgG subclasses bind feline FcRn and have been compared to human IgG analogues. Half-life of feline IgG remains to be fully studied because, without any experimental support, one cannot expect or predict whether or not they will align closely with human IgGs.

Extended half-life of IgG could allow less frequent dosing and/or lower dose of the antibody drug, which in turn reduces veterinary visits, improves patient compliance, and lowers the concentration-dependent cytotoxicity/adverse events.

Accordingly, there exists a need to identify mutations in the Fc constant regions to improve half-life.

SUMMARY OF THE INVENTION

The invention relates to mutant feline IgGs that provide higher FcRn affinity and higher half-life, relative to wild-type feline IgGs. Specifically, the inventors of the instant application have found that substituting the amino acid residue serine (Ser or S) at position 428 or 434 with another amino acid surprisingly and unexpectedly enhanced the affinity to FcRn, and thereby increased the half-life of IgG.

In one aspect, the invention provides a modified IgG comprising: a feline IgG constant domain comprising at least one amino acid substitution relative to a wild-type feline IgG constant domain, wherein said substitution is at amino acid residue 428 or 434, numbered according to the EU index as in Kabat. In an exemplary embodiment, said substitution is a substitution of the serine at position 428 with leucine (S428L). In another exemplary embodiment, said substitution is a substitution of the serine at position 434 with histidine (S434H). In some embodiments, the feline IgG constant domain comprises substitutions of serines at both 428 and 434 positions with leucine and histidine, respectively.

In another aspect, the invention provides a polypeptide comprising: a feline IgG constant domain comprising one or more amino acid substitutions relative to a wild-type feline IgG constant domain, wherein said one or more substitutions are at amino acid residues 428, 434, or a combination thereof.

In yet another aspect, the invention provides an antibody or a molecule comprising: a feline IgG constant domain comprising one or more amino acid substitutions relative to a wild-type feline IgG constant domain, wherein said one or more substitutions are at amino acid residues 428, 434, or a combination thereof.

In a further aspect, the invention provides a method for producing or manufacturing an antibody or a molecule, the method comprising: providing a vector or a host cell having an antibody comprising a feline IgG constant domain, said feline IgG constant domain comprising one or more amino acid substitutions relative to a wild-type feline IgG constant domain, wherein said one or more substitutions are at amino acid residues 428, 434, or a combination thereof.

In another aspect, the invention provides a method for increasing an antibody serum half-life in a cat, the method comprising: administering said cat a therapeutically effective amount of an antibody comprising a feline IgG constant domain, said feline IgG constant domain comprising one or more amino acid substitutions relative to a wild-type feline IgG constant domain, wherein said one or more substitutions are at amino acid residues 428, 434, or a combination thereof.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIG. 2A shows the alignment of the amino acid sequences of wild-type (WT) human IgG1, WT feline IgG1a, WT feline IgG1b, WT feline IgG2 and mutant feline IgG2 having hinge mutation. The amino acid residues are numbered according to the Eu index as in Kabat. The CH1, hinge, CH2, and CH3 amino acid residues are in red, violet, blue, and green, respectively. FIG. 2B shows feline Fc IgG1a WT nucleotide sequence. FIG. 2C shows feline Fc IgG1a S434H nucleotide sequence. FIG. 2D shows feline Fc IgG1a S428L nucleotide sequence.

Figure 1:
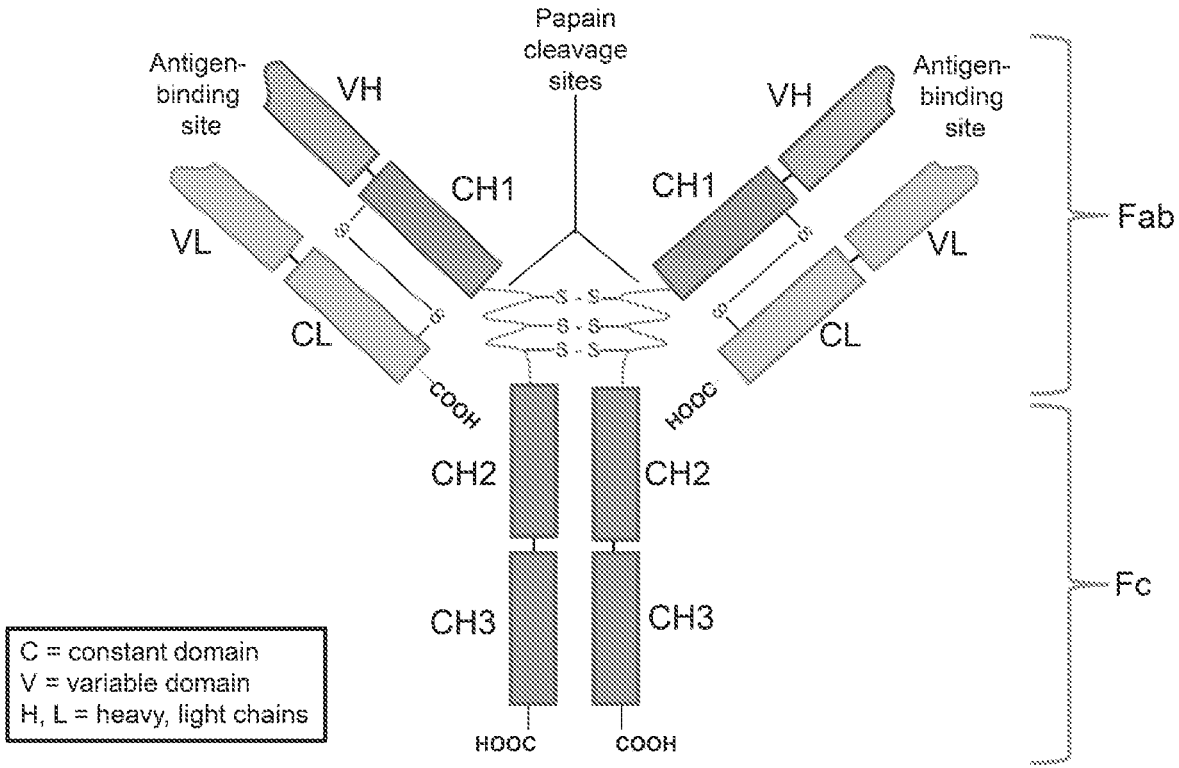
FIG. 1 illustrates domain structure of IgG. Fc mutations S428L and/or N434H were made in the CH3 domain to increase IgG half-life by increasing affinity to FcRn at pH6.
Figure 3:
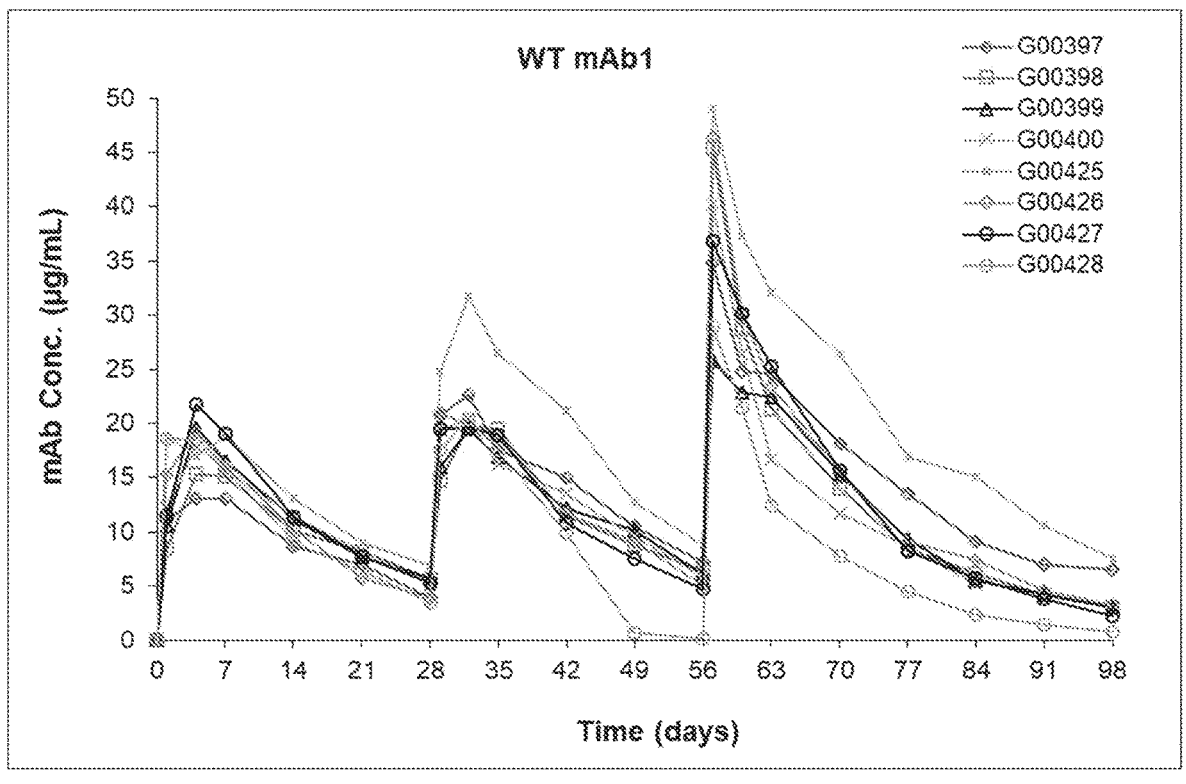
FIG. 3 shows individual serum concentrations for WT mAb1 IgG in 8 cats, 4 male (G00397, G00398, G00399, G00400) and 4 female (G00425, G00426, G00427, G00428) after three injections of 2 mg/kg (SC/SC/IV) measured over a 98 day period.
Figure 4:
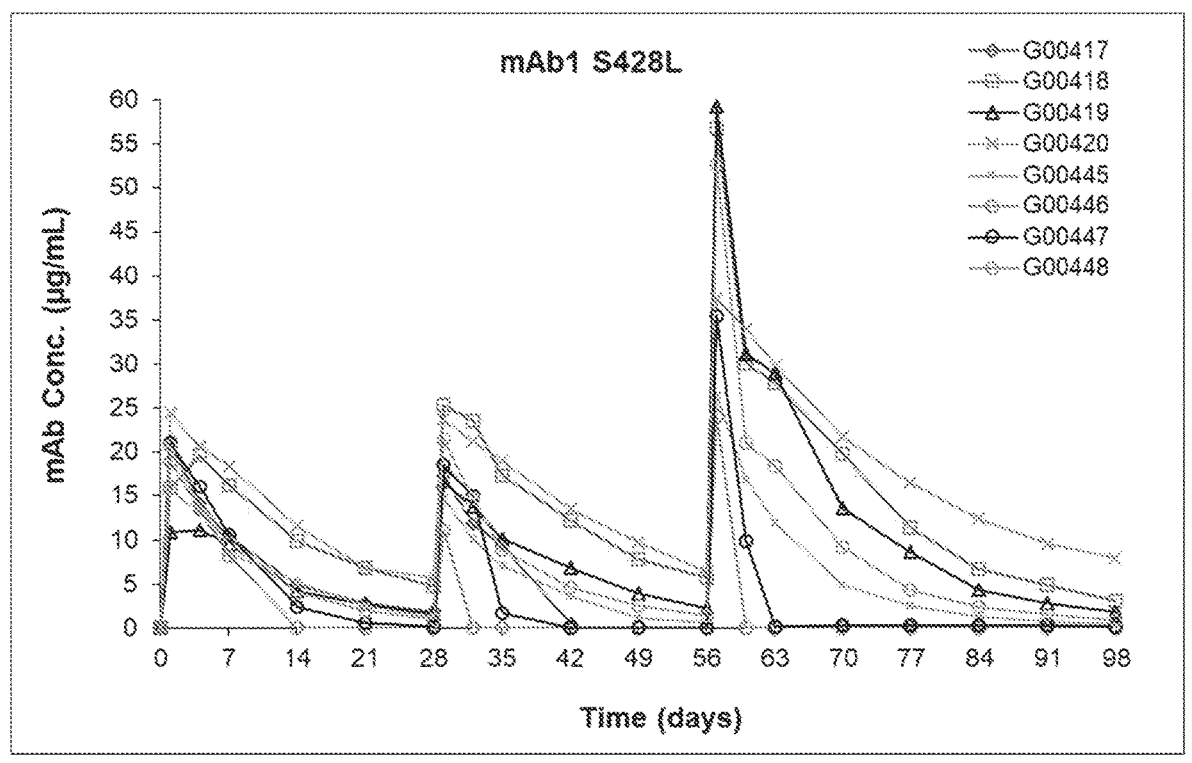
FIG. 4 shows individual serum concentrations for WT mAb1 IgG in 8 cats, 4 male (G00417, G00418, G00419, G00420) and 4 female (G00445, G00446, G00447, G0448) after three injections of 2 mg/kg (SC/SC/IV) measured over a 98 day period.
Figure 5:
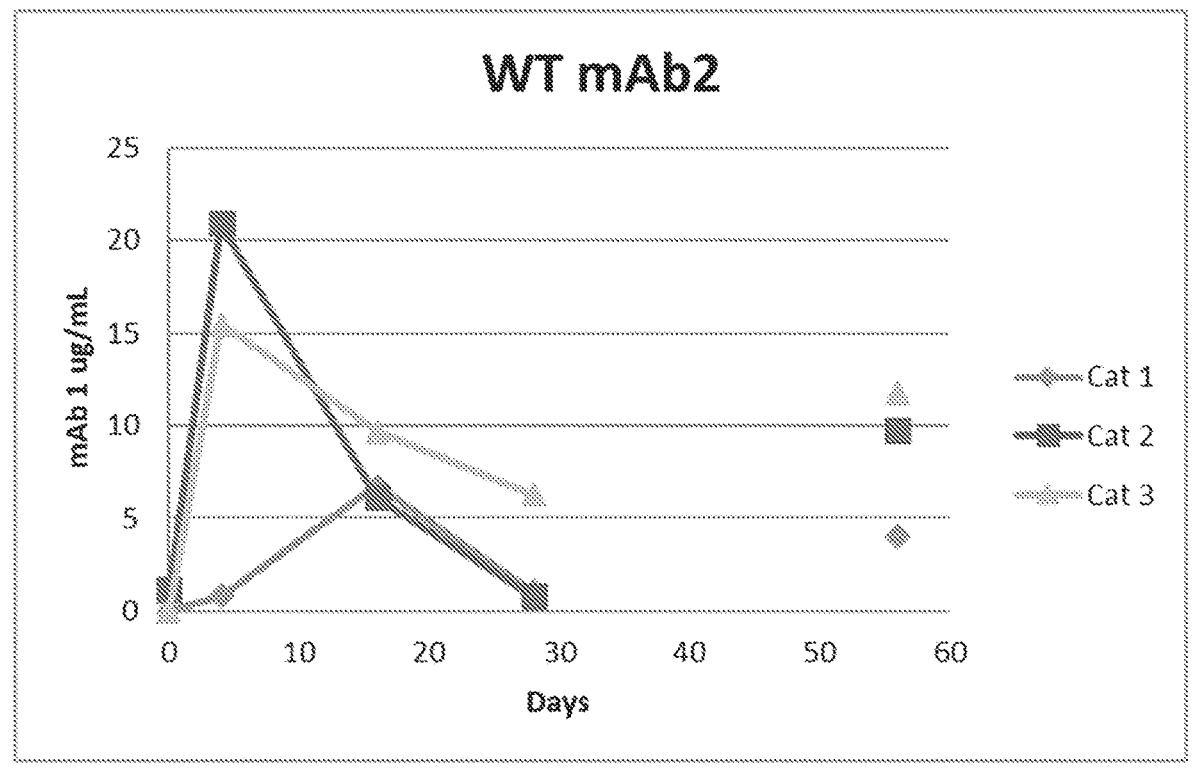
FIG. 5 shows individual serum concentrations for WT mAb2 in 3 cats after a single subcutaneous injection of 2 mg/kg measured over a 30 day period.
Figure 6:
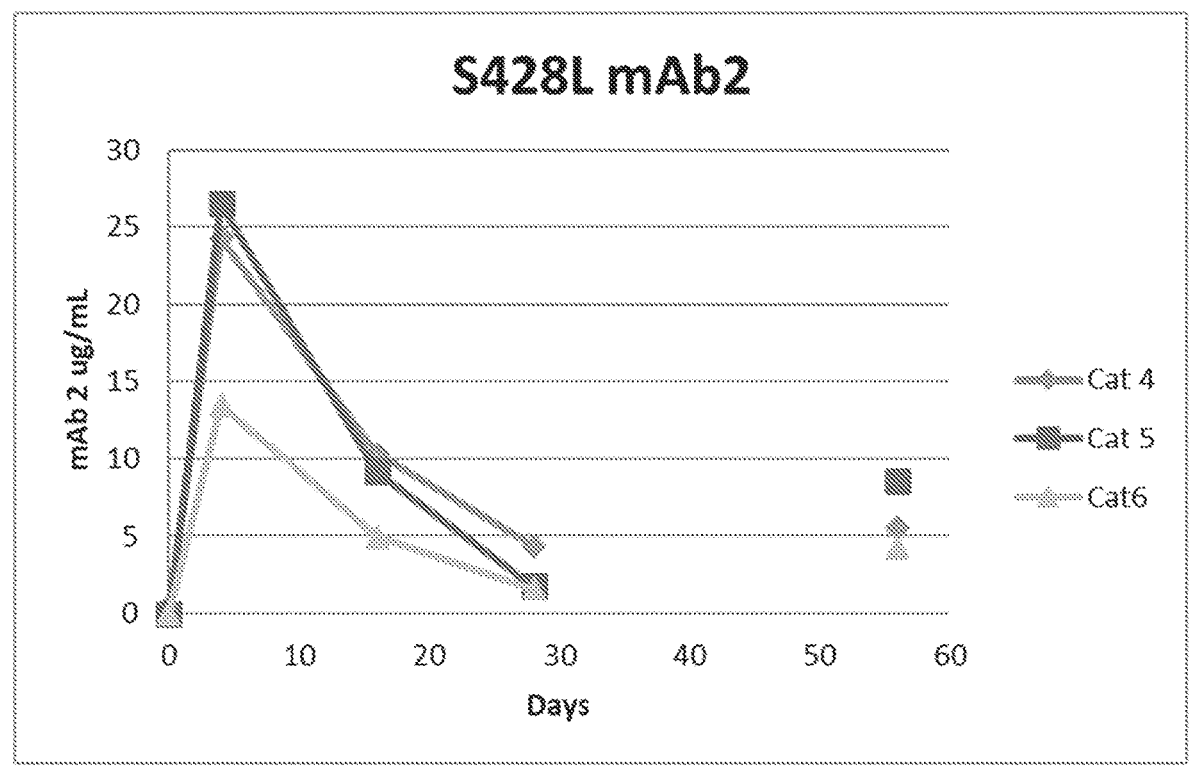
FIG. 6 shows individual serum concentrations for mutant S428L mAb2 in 3 cats after a single subcutaneous injection of 2 mg/kg measured over a 30 day period.
Figure 7:
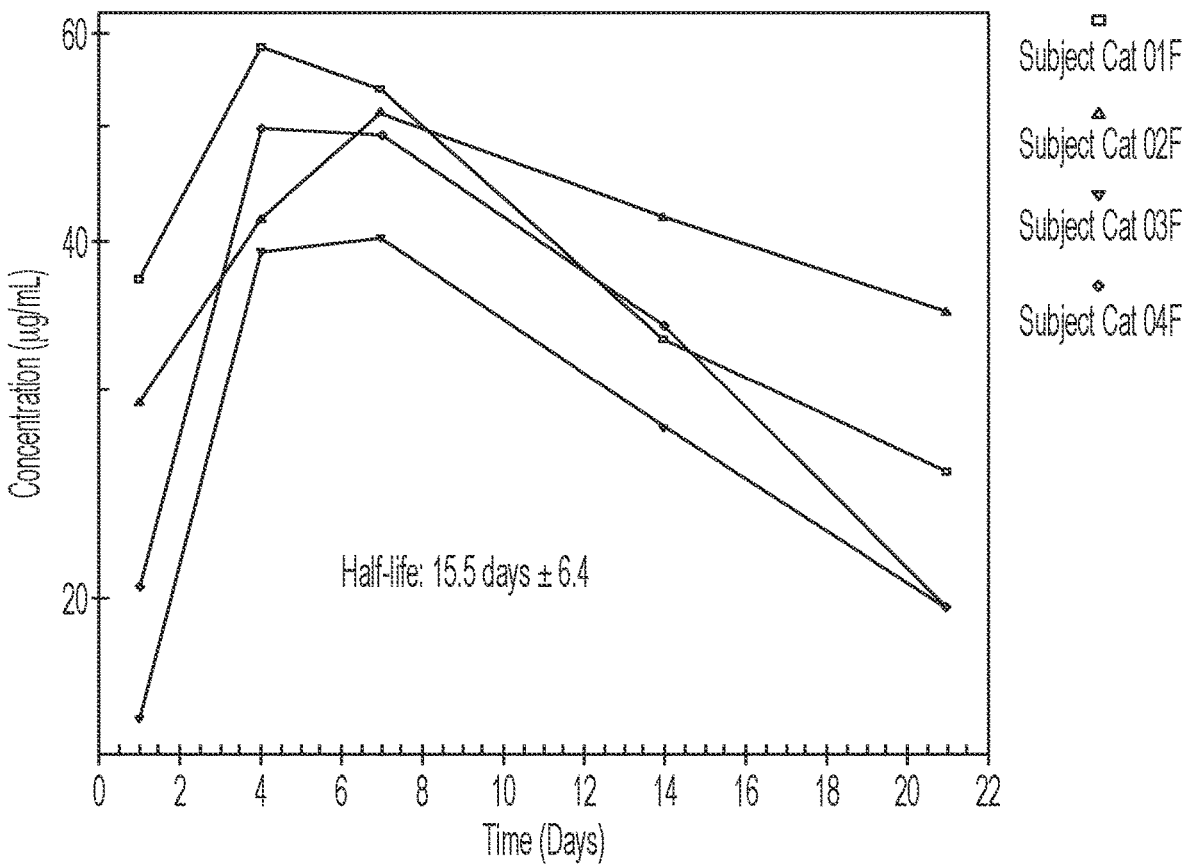
FIG. 7 shows individual serum concentrations for mutant S428L mAb3 in cats after a single subcutaneous injection of 2 mg/kg measured over a 21 day period.
Figure 8:
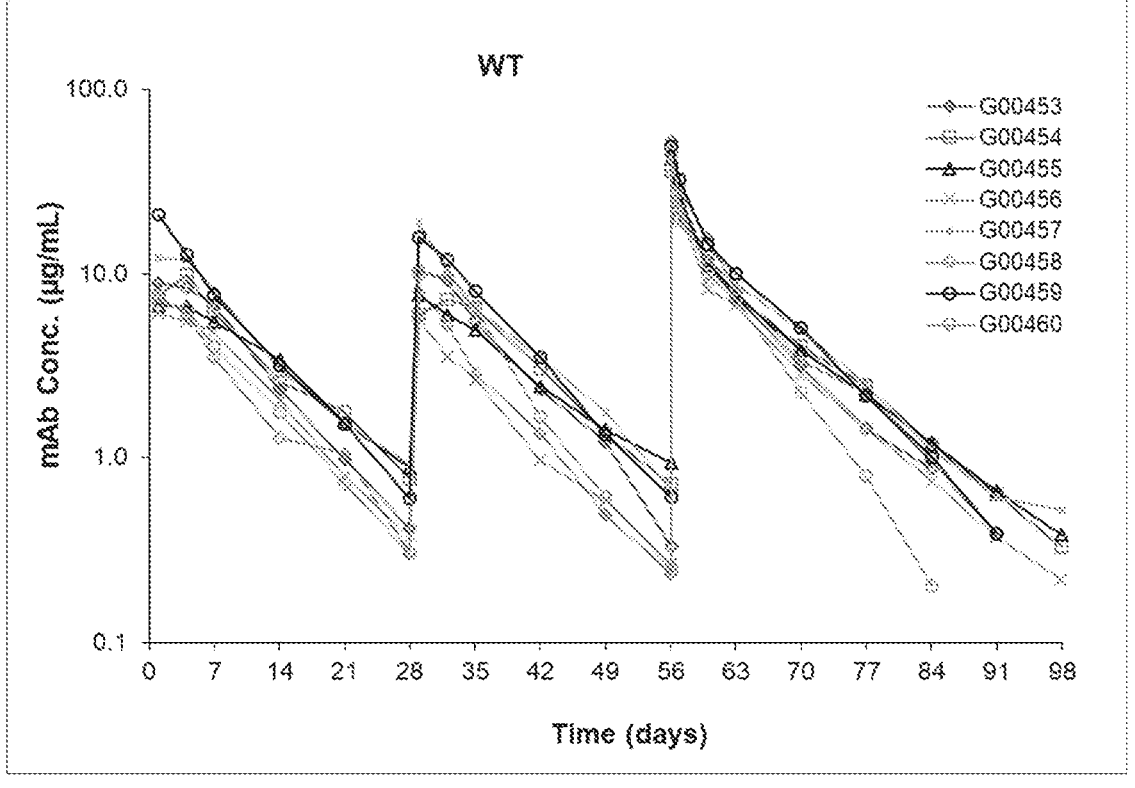
FIG. 8 shows individual serum concentrations for WT mAb3 IgG in 8 cats, 4 male (G00453, G00454, G00455, G00456) and 4 female (G00457, G00458, G00459, G00460) after three injections of 2 mg/kg (SC/SC/IV) measured over a 98 day period.
Figure 9:
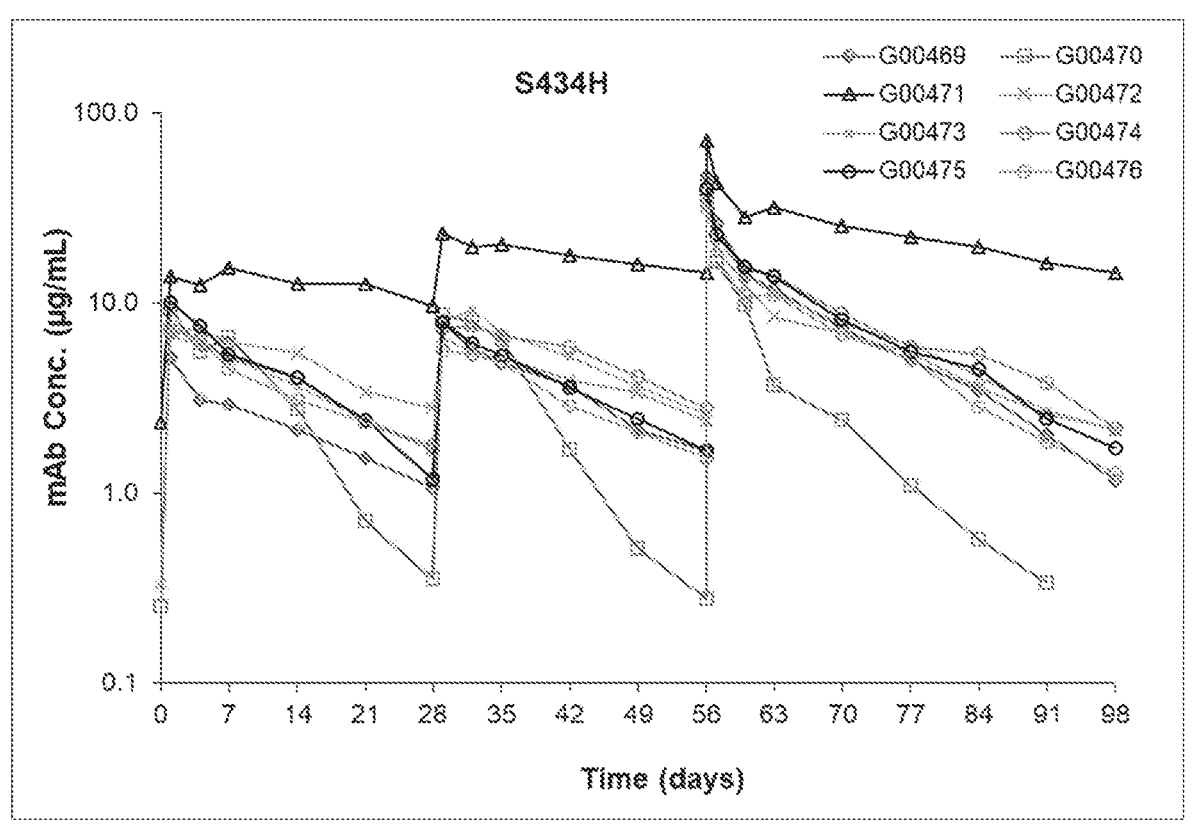
FIG. 9 shows individual serum concentrations for S434H mAb3 IgG in 8 cats, 4 male (G00469, G00470, G00471, G00472) and 4 female (G00473, G00474, G00475, G0476) after three injections of 2 mg/kg (SC/SC/IV) measured over a 98 day period.

BRIEF DESCRIPTION OF THE SEQUENCE
LISTING

SEQ ID NO.: 1 is the amino acid sequence of the mutant IgG1a constant domain having S428L mutation.

SEQ ID NO.: 2 is the amino acid sequence of the mutant IgG1a constant domain having S434H mutation.

SEQ ID NO.: 3 is the amino acid sequence of the wildtype IgG1a constant domain.

SEQ ID NO.: 4 is the nucleic acid sequence of the wildtype IgG1a constant domain.

SEQ ID NO.: 5 is the amino acid sequence of IgG1a CH1 domain.

SEQ ID NO.: 6 is the amino acid sequence of IgG1a hinge domain.

SEQ ID NO.: 7 is the amino acid sequence of IgG1a CH2 domain.

SEQ ID NO.: 8 is the amino acid sequence of IgG1a WT CH3 domain.

SEQ ID NO.: 9 is the nucleic acid sequence of IgG1a CH1 domain.

SEQ ID NO.: 10 is the nucleic acid sequence of IgG1a hinge domain.

SEQ ID NO.: 11 is the nucleic acid sequence of IgG1a CH2 domain.

SEQ ID NO.: 12 is the nucleic acid sequence of IgG1a WT CH3 domain.

SEQ ID NO.: 13 is the nucleic acid sequence of anti-IL31 antibody (ZTS-5864) Heavy Chain Variable Region.

SEQ ID NO.: 14 is the amino acid sequence of anti-IL31 antibody (ZTS-5864) Heavy Chain Variable Region.

SEQ ID NO.: 15 is the amino acid sequence of anti-IL31 antibody (ZTS-5864) Heavy Chain Variable Region CDR1.

SEQ ID NO.: 16 is the amino acid sequence of anti-IL31 antibody (ZTS-5864) Heavy Chain Variable Region CDR2.

SEQ ID NO.: 17 is the amino acid sequence of anti-IL31 antibody (ZTS-5864) Heavy Chain Variable Region CDR3.

SEQ ID NO.: 18 is the nucleic acid sequence of anti-IL31 antibody (ZTS-5864) Light Chain Variable Region.

SEQ ID NO.: 19 is the amino acid sequence of anti-IL31 antibody (ZTS-5864) Light Chain Variable Region.

SEQ ID NO.: 20 is the amino acid sequence of anti-IL31 antibody (ZTS-5864) Light Chain Variable Region CDR1.

SEQ ID NO.: 21 is the amino acid sequence of anti-IL31 antibody (ZTS-5864) Light Chain Variable Region CDR2.

SEQ ID NO.: 22 is the amino acid sequence of anti-IL31 antibody (ZTS-5864) Light Chain Variable Region CDR3.

SEQ ID NO.: 23 is the amino acid sequence of anti-NGF antibody (ZTS768) Heavy chain.

SEQ ID NO.: 24 is the amino acid sequence of anti-NGF antibody (ZTS768) Heavy chain CDR1.

SEQ ID NO.: 25 is the amino acid sequence of anti-NGF antibody (ZTS768) Heavy chain CDR2.

SEQ ID NO.: 26 is the amino acid sequence of anti-NGF antibody (ZTS768) Heavy chain CDR3.

SEQ ID NO.: 27 is the amino acid sequence of anti-NGF antibody (ZTS768) Light chain.

SEQ ID NO.: 28 is the amino acid sequence of anti-NGF antibody (ZTS768) Light chain CDR1.

SEQ ID NO.: 29 is the amino acid sequence of anti-NGF antibody (ZTS768) Light chain CDR2.

SEQ ID NO.: 30 is the amino acid sequence of anti-NGF antibody (ZTS768) Light chain CDR3.

SEQ ID NO.: 31 is the amino acid sequence of anti-NGF antibody (NV02) Heavy chain.

SEQ ID NO.: 32 is the amino acid sequence of anti-NGF antibody (NV02) Heavy chain CDR1.

SEQ ID NO.: 33 is the amino acid sequence of anti-NGF antibody (NV02) Heavy chain CDR2.

SEQ ID NO.: 34 is the amino acid sequence of anti-NGF antibody (NV02) Heavy chain CDR3.

SEQ ID NO.: 35 is the amino acid sequence of anti-NGF antibody (NV02) Kappa chain.

SEQ ID NO.: 36 is the amino acid sequence of anti-NGF antibody (NV02) Kappa chain CDR1.

SEQ ID NO.: 37 is the amino acid sequence of anti-NGF antibody (NV02) Kappa chain CDR2.

SEQ ID NO.: 38 is the amino acid sequence of anti-NGF antibody (NV02) Kappa chain CDR3.

SEQ ID NO: 39 is a variable heavy chain CDR1 of anti-TGFβ1,3 antibody referred to herein as ZTS-310;

SEQ ID NO: 40 is a variable heavy chain CDR2 of anti-TGFβ1,3 antibody referred to herein as ZTS-310;

SEQ ID NO: 41 is a variable heavy chain CDR3 of anti-TGFβ1,3 antibody referred to herein as ZTS-310;

SEQ ID NO: 42 is a variable light chain CDR1 of anti-TGFβ1,3 antibody referred to herein as ZTS-310;

SEQ ID NO: 43 is a variable light chain CDR2 of anti-TGFβ1,3 antibody referred to herein as ZTS-310;

SEQ ID NO: 44 is a variable light chain CDR3 of anti-TGFβ1,3 antibody referred to herein as ZTS-310;

SEQ ID NO: 45 is the amino acid sequence of a heavy chain of anti-TGFβ1,3 antibody referred to herein as ZTS-310;

SEQ ID NO: 46 is the nucleic acid sequence of a heavy chain of anti-TGFβ1,3 antibody referred to herein as ZTS-310.

SEQ ID NO: 47 is the amino acid sequence of a light chain of anti-TGFβ1,3 antibody referred to herein as ZTS-310;

SEQ ID NO: 48 is the nucleic acid sequence of a light chain of anti-TGFβ1,3 antibody referred to herein as ZTS-310;

SEQ ID NO: 49 is a variable heavy chain CDR1 of anti-TGFβ1,2,3 antibody referred to herein as ZTS-120-1;

SEQ ID NO: 50 is a variable heavy chain CDR2 of anti-TGFβ1,2,3 antibody referred to herein as ZTS-120-1;

SEQ ID NO: 51 is a variable heavy chain CDR3 of anti-TGFβ1,2,3 antibody referred to herein as ZTS-120-1;

SEQ ID NO: 52 is a variable light chain CDR1 of anti-TGFβ1,2,3 antibody referred to herein as ZTS-120-1;

SEQ ID NO: 53 is a variable light chain CDR2 of anti-TGFβ1,2,3 antibody referred to herein as ZTS-120-1;

SEQ ID NO: 54 is a variable light chain CDR3 of anti-TGFβ1,2,3 antibody referred to herein as ZTS-120-1;

SEQ ID NO: 55 is the amino acid sequence of a heavy chain of anti-TGFβ1,2,3 antibody referred to herein as ZTS-120-1;

SEQ ID NO: 56 is the nucleic acid sequence of a heavy chain of anti-TGFβ1,2,3 antibody referred to herein as ZTS-120-1;

SEQ ID NO: 57 is the amino acid sequence of a light chain of anti-TGFβ1,2,3 antibody referred to herein as ZTS-120-1;

SEQ ID NO: 58 is the nucleic acid sequence of a light chain of anti-TGFβ1,2,3 antibody referred to herein as ZTS-120-1;

SEQ ID NO: 59 is a variable heavy chain CDR1 of anti-TGFβ1,2,3 antibody referred to herein as ZTS-120-2;

SEQ ID NO: 60 is a variable heavy chain CDR2 of anti-TGFβ1,2,3 antibody referred to herein as ZTS-120-2;

SEQ ID NO: 61 is a variable heavy chain CDR3 of anti-TGFβ1,2,3 antibody referred to herein as ZTS-120-2;

SEQ ID NO: 62 is a variable light chain CDR1 of anti-TGFβ1,2,3 antibody referred to herein as ZTS-120-2;

SEQ ID NO: 63 is a variable light chain CDR2 of anti-TGFβ1,2,3 antibody referred to herein as ZTS-120-2;

SEQ ID NO: 64 is a variable light chain CDR3 of anti-TGFβ1,2,3 antibody referred to herein as ZTS-120-2;

SEQ ID NO: 65 is the amino acid sequence of a heavy chain of anti-TGFβ1,2,3 antibody referred to herein as ZTS-120-2;

SEQ ID NO: 66 is the nucleic acid sequence of a heavy chain of anti-TGFβ1,2,3 antibody referred to herein as ZTS-120-2;

SEQ ID NO: 67 is the amino acid sequence of a light chain of anti-TGFβ1,2,3 antibody referred to herein as ZTS-120-2;

SEQ ID NO: 68 is the nucleic acid sequence of a light chain of anti-TGFβ1,2,3 antibody referred to herein as ZTS-120-2;

SEQ ID NO: 69 is a variable heavy chain CDR1 of anti-TGFβ1,2,3 antibody referred to herein as ZTS-120-3;

SEQ ID NO: 70 is a variable heavy chain CDR2 of anti-TGFβ1,2,3 antibody referred to herein as ZTS-120-3;

SEQ ID NO: 71 is a variable heavy chain CDR3 of anti-TGFβ1,2,3 antibody referred to herein as ZTS-120-3;

SEQ ID NO: 72 is a variable light chain CDR1 of anti-TGFβ1,2,3 antibody referred to herein as ZTS-120-3;

SEQ ID NO: 73 is a variable light chain CDR2 of anti-TGFβ1,2,3 antibody referred to herein as ZTS-120-3;

SEQ ID NO: 74 is a variable light chain CDR3 of anti-TGFβ1,2,3 antibody referred to herein as ZTS-120-3;

SEQ ID NO: 75 is the amino acid sequence of a heavy chain of anti-TGFβ1,2,3 antibody referred to herein as ZTS-120-3;

SEQ ID NO: 76 is the nucleic acid sequence of a heavy chain of anti-TGFβ1,2,3 antibody referred to herein as ZTS-120-3;

SEQ ID NO: 77 is the amino acid sequence of a light chain of anti-TGFβ1,2,3 antibody referred to herein as ZTS-120-3;

SEQ ID NO: 78 is the nucleic acid sequence of a light chain of anti-TGFβ1,2,3 antibody referred to herein as ZTS-120-3;

SEQ ID NO: 79 is a variable heavy chain CDR1 of anti-TGFβ1,2,3 antibody referred to herein as ZTS-120-4;

SEQ ID NO: 80 is a variable heavy chain CDR2 of anti-TGFβ1,2,3 antibody referred to herein as ZTS-120-4;

SEQ ID NO: 81 is a variable heavy chain CDR3 of anti-TGFβ1,2,3 antibody referred to herein as ZTS-120-4;

SEQ ID NO: 82 is a variable light chain CDR1 of anti-TGFβ1,2,3 antibody referred to herein as ZTS-120-4;

SEQ ID NO: 83 is a variable light chain CDR2 of anti-TGFβ1,2,3 antibody referred to herein as ZTS-120-4;

SEQ ID NO: 84 is a variable light chain CDR3 of anti-TGFβ1,2,3 antibody referred to herein as ZTS-120-4;

SEQ ID NO: 85 is the amino acid sequence of a heavy chain of anti-TGFβ1,2,3 antibody referred to herein as ZTS-120-4;

SEQ ID NO: 86 is the nucleic acid sequence of a heavy chain of anti-TGFβ1,2,3 antibody referred to herein as ZTS-120-4;

SEQ ID NO: 87 is the amino acid sequence of a light chain of anti-TGFβ1,2,3 antibody referred to herein as ZTS-120-4;

SEQ ID NO: 88 is the nucleic acid sequence of a light chain of anti-TGFβ1,2,3 antibody referred to herein as ZTS-120-4;

SEQ ID NO: 89 is a variable heavy chain CDR1 of anti-TGFβ1,2,3 antibody referred to herein as ZTS-120-5;

SEQ ID NO: 90 is a variable heavy chain CDR2 of anti-TGFβ1,2,3 antibody referred to herein as ZTS-120-5;

SEQ ID NO: 91 is a variable heavy chain CDR3 of anti-TGFβ1,2,3 antibody referred to herein as ZTS-120-5;

SEQ ID NO: 92 is a variable light chain CDR1 of anti-TGFβ1,2,3 antibody referred to herein as ZTS-120-5;

SEQ ID NO: 93 is a variable light chain CDR2 of anti-TGFβ1,2,3 antibody referred to herein as ZTS-120-5;

SEQ ID NO: 94 is a variable light chain CDR3 of anti-TGFβ1,2,3 antibody referred to herein as ZTS-120-5;

SEQ ID NO: 95 is the amino acid sequence of a heavy chain of anti-TGFβ1,2,3 antibody referred to herein as ZTS-120-5;

SEQ ID NO: 96 is the nucleic acid sequence of a heavy chain of anti-TGFβ1,2,3 antibody referred to herein as ZTS-120-5;

SEQ ID NO: 97 is the amino acid sequence of a light chain of anti-TGFβ1,2,3 antibody referred to herein as ZTS-120-5;

SEQ ID NO: 98 is the nucleic acid sequence of a light chain of anti-TGFβ1,2,3 antibody referred to herein as ZTS-120-5;

SEQ ID NO: 99 is a variable heavy chain CDR1 of anti-TGFβ1,2,3 antibody referred to herein as ZTS-120-6;

SEQ ID NO: 100 is a variable heavy chain CDR2 of anti-TGFβ1,2,3 antibody referred to herein as ZTS-120-6;

SEQ ID NO: 101 is a variable heavy chain CDR3 of anti-TGFβ1,2,3 antibody referred to herein as ZTS-120-6;

SEQ ID NO: 102 is a variable light chain CDR1 of anti-TGFβ1,2,3 antibody referred to herein as ZTS-120-6;

SEQ ID NO: 103 is a variable light chain CDR2 of anti-TGFβ1,2,3 antibody referred to herein as ZTS-120-6;

SEQ ID NO: 104 is a variable light chain CDR3 of anti-TGFβ1,2,3 antibody referred to herein as ZTS-120-6;

SEQ ID NO: 105 is the amino acid sequence of a heavy chain of anti-TGFβ1,2,3 antibody referred to herein as ZTS-120-6;

SEQ ID NO: 106 is the nucleic acid sequence of a heavy chain of anti-TGFβ1,2,3 antibody referred to herein as ZTS-120-6;

SEQ ID NO: 107 is the amino acid sequence of a light chain of anti-TGFβ1,2,3 antibody referred to herein as ZTS-120-6;

SEQ ID NO: 108 is the nucleic acid sequence of a light chain of anti-TGFβ1,2,3 antibody referred to herein as ZTS-120-6;

SEQ ID NO: 109 is a variable heavy chain CDR1 of anti-TGFβ1,2,3 antibody referred to herein as ZTS-120-7;

SEQ ID NO: 110 is a variable heavy chain CDR2 of anti-TGFβ1,2,3 antibody referred to herein as ZTS-120-7;

SEQ ID NO: 111 is a variable heavy chain CDR3 of anti-TGFβ1,2,3 antibody referred to herein as ZTS-120-7;

SEQ ID NO: 112 is a variable light chain CDR1 of anti-TGFβ1,2,3 antibody referred to herein as ZTS-120-7;

SEQ ID NO: 113 is a variable light chain CDR2 of anti-TGFβ1,2,3 antibody referred to herein as ZTS-120-7;

SEQ ID NO: 114 is a variable light chain CDR3 of anti-TGFβ1,2,3 antibody referred to herein as ZTS-120-7;

SEQ ID NO: 115 is the amino acid sequence of a heavy chain of anti-TGFβ1,2,3 antibody referred to herein as ZTS-120-7;

SEQ ID NO: 116 is the nucleic acid sequence of a heavy chain of anti-TGFβ1,2,3 antibody referred to herein as ZTS-120-7;

SEQ ID NO: 117 is the amino acid sequence of a light chain of anti-TGFβ1,2,3 antibody referred to herein as ZTS-120-7;

SEQ ID NO: 118 is the nucleic acid sequence of a light chain of anti-TGFβ1,2,3 antibody referred to herein as ZTS-120-7;

SEQ ID NO: 119 is a variable heavy chain CDR1 of anti-TGFβ1,2,3 antibody referred to herein as ZTS-120-8;

SEQ ID NO: 120 is a variable heavy chain CDR2 of anti-TGFβ1,2,3 antibody referred to herein as ZTS-120-8;

SEQ ID NO: 121 is a variable heavy chain CDR3 of anti-TGFβ1,2,3 antibody referred to herein as ZTS-120-8;

SEQ ID NO: 122 is a variable light chain CDR1 of anti-TGFβ1,2,3 antibody referred to herein as ZTS-120-8;

SEQ ID NO: 123 is a variable light chain CDR2 of anti-TGFβ1,2,3 antibody referred to herein as ZTS-120-8;

SEQ ID NO: 124 is a variable light chain CDR3 of anti-TGFβ1,2,3 antibody referred to herein as ZTS-120-8;

SEQ ID NO: 125 is the amino acid sequence of a heavy chain of anti-TGFβ1,2,3 antibody referred to herein as ZTS-120-8;

SEQ ID NO: 126 is the nucleic acid sequence of a heavy chain of anti-TGFβ1,2,3 antibody referred to herein as ZTS-120-8;

SEQ ID NO: 127 is the amino acid sequence of a light chain of anti-TGFβ1,2,3 antibody referred to herein as ZTS-120-8;

SEQ ID NO: 128 is the nucleic acid sequence of a light chain of anti-TGFβ1,2,3 antibody referred to herein as ZTS-120-8;

SEQ ID NO: 129 is a variable heavy chain CDR1 of anti-TGFβ1,2,3 antibody referred to herein as ZTS-120-9;

SEQ ID NO: 130 is a variable heavy chain CDR2 of anti-TGFβ1,2,3 antibody referred to herein as ZTS-120-9;

SEQ ID NO: 131 is a variable heavy chain CDR3 of anti-TGFβ1,2,3 antibody referred to herein as ZTS-120-9;

SEQ ID NO: 132 is a variable light chain CDR1 of anti-TGFβ1,2,3 antibody referred to herein as ZTS-120-9;

SEQ ID NO: 133 is a variable light chain CDR2 of anti-TGFβ1,2,3 antibody referred to herein as ZTS-120-9;

SEQ ID NO: 134 is a variable light chain CDR3 of anti-TGFβ1,2,3 antibody referred to herein as ZTS-120-9;

SEQ ID NO: 135 is the amino acid sequence of a heavy chain of anti-TGFβ1,2,3 antibody referred to herein as ZTS-120-9;

SEQ ID NO: 136 is the nucleic acid sequence of a heavy chain of anti-TGFβ1,2,3 antibody referred to herein as ZTS-120-9;

SEQ ID NO: 137 is the amino acid sequence of a light chain of anti-TGFβ1,2,3 antibody referred to herein as ZTS-120-9;

SEQ ID NO: 138 is the nucleic acid sequence of a light chain of anti-TGFβ1,2,3 antibody referred to herein as ZTS-120-9.

DETAILED DESCRIPTION OF THE INVENTION

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

Definitions

In the present disclosure the singular forms "a," "an," and "the" include the plural reference, and reference to a particular numerical value includes at least that particular value, unless the context clearly indicates otherwise. Thus, for example, a reference to "a molecule" or "a compound" is a reference to one or more of such molecules or compounds and equivalents thereof known to those skilled in the art, and so forth. The term "plurality", as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

In the specification and claims, the numbering of the amino acid residues in an immunoglobulin heavy chain is that of the Eu index as in Kabat et al., Sequences of Proteins of Immunological Interest, 5th Ed. Public Health Service, National Institutes of Health, Bethesda, Md. (1991). The "Eu index as in Kabat" refers to the residue numbering of the IgG antibody and is reflected herein in FIG. 2A.

The term "isolated" when used in relation to a nucleic acid is a nucleic acid that is identified and separated from at least one contaminant nucleic acid with which it is ordinarily associated in its natural source. Isolated nucleic acid is in a form or setting different from that in which it is found in nature. Isolated nucleic acid molecules therefore are distinguished from the nucleic acid molecule as it exists in natural cells. An isolated nucleic acid molecule includes a nucleic acid molecule contained in cells that ordinarily express the polypeptide encoded therein where, for example, the nucleic acid molecule is in a plasmid or a chromosomal location different from that of natural cells. The isolated nucleic acid may be present in single-stranded or double-stranded form. When an isolated nucleic acid molecule is to be utilized to express a protein, the oligonucleotide or polynucleotide will contain at a minimum the sense or coding strand, but may contain both the sense and anti-sense strands (i.e., may be double-stranded).

A nucleic acid molecule is "operably linked" or "operably attached" when it is placed into a functional relationship with another nucleic acid molecule. For example, a promoter or enhancer is operably linked to a coding sequence of nucleic acid if it affects the transcription of the sequence; or a ribosome binding site is operably linked to a coding sequence of nucleic acid if it is positioned so as to facilitate translation. A nucleic acid molecule encoding a variant Fc region is operably linked to a nucleic acid molecule encoding a heterologous protein (i.e., a protein or functional fragment thereof which does not, as it exists in nature, comprise an Fc region) if it is positioned such that the expressed fusion protein comprises the heterologous protein or functional fragment thereof adjoined either upstream or downstream to the variant Fc region polypeptide; the heterologous protein may by immediately adjacent to the variant Fc region polypeptide or may be separated therefrom by a linker sequence of any length and composition. Likewise, a polypeptide (used synonymously herein with "protein") molecule is "operably linked" or "operably attached" when it is placed into a functional relationship with another polypeptide.

As used herein the term "functional fragment" when in reference to a polypeptide or protein (e.g., a variant Fc region, or a monoclonal antibody) refers to fragments of that protein which retain at least one function of the full-length polypeptide. The fragments may range in size from six amino acids to the entire amino acid sequence of the full-length polypeptide minus one amino acid. A functional fragment of a variant Fc region polypeptide of the present invention retains at least one "amino acid substitution" as herein defined. A functional fragment of a variant Fc region polypeptide retains at least one function known in the art to be associated with the Fc region (e.g., ADCC, CDC, Fc receptor binding, Clq binding, down regulation of cell surface receptors or may, e.g., increase the in vivo or in vitro half-life of a polypeptide to which it is operably attached).

The term "purified" or "purify" refers to the substantial removal of at least one contaminant from a sample. For example, an antigen-specific antibody may be purified by complete or substantial removal (at least 90%, 91%, 92%, 93%, 94%, 95%, or more preferably at least 96%, 97%, 98% or 99%) of at least one contaminating non-immunoglobulin protein; it may also be purified by the removal of immunoglobulin protein that does not bind to the same antigen. The removal of non-immunoglobulin proteins and/or the removal of immunoglobulins that do not bind a particular antigen results in an increase in the percent of antigen-specific immunoglobulins in the sample. In another example, a polypeptide (e.g., an immunoglobulin) expressed in bacterial host cells is purified by the complete or substantial removal of host cell proteins; the percent of the polypeptide is thereby increased in the sample.

The term "native" as it refers to a polypeptide (e.g., Fc region) is used herein to indicate that the polypeptide has an amino acid sequence consisting of the amino acid sequence of the polypeptide as it commonly occurs in nature or a naturally occurring polymorphism thereof. A native polypeptide (e.g., native Fc region) may be produced by recombinant means or may be isolated from a naturally occurring source.

The term "expression vector" as used herein refers to a recombinant DNA molecule containing a desired coding sequence and appropriate nucleic acid sequences necessary for the expression of the operably linked coding sequence in a particular host organism.

As used herein, the term "host cell" refers to any eukaryotic or prokaryotic cell (e.g., bacterial cells such as *E. coli*, CHO cells, yeast cells, mammalian cells, avian cells, amphibian cells, plant cells, fish cells, and insect cells), whether located in vitro or in situ, or in vivo As used herein, the term "Fc region" refers to a C-terminal region of an immunoglobulin heavy chain. The "Fc region" may be a native sequence Fc region or a variant Fc region. Although the generally accepted boundaries of the Fc region of an immunoglobulin heavy chain might vary, the feline IgG heavy chain Fc region is usually defined to stretch, for example, from an amino acid residue at position 231, to the carboxyl-terminus thereof. In some embodiments, variants comprise only portions of the Fc region and can include or not include the carboxy-terminus. The Fc region of an immunoglobulin generally comprises two constant domains, CH2 and CH3. In some embodiments, variants having one or more of the constant domains are contemplated. In other embodiments, variants without such constant domains (or with only portions of such constant domains) are contemplated.

The "CH2 domain" of a feline IgG Fc region usually extends, for example, from about amino acid 231 to about amino acid 340 (see FIG. 2A). The CH2 domain is unique in that it is not closely paired with another domain. Two N-linked branched carbohydrate chains are interposed between the two CH2 domains of an intact native IgG molecule.

The "CH3 domain" of a feline IgG Fc region generally is the stretch of residues C-terminal to a CH2 domain in an Fc region extending, for example, from about amino acid residue 341 to about amino acid residue 447 (see FIG. 2A).

A "functional Fc region" possesses an "effector function" of a native sequence Fc region. At least one effector function of a polypeptide comprising a variant Fc region of the present invention may be enhanced or diminished with respect to a polypeptide comprising a native Fc region or the parent Fc region of the variant. Examples of effector functions include, but are not limited to: Clq binding; complement dependent cytotoxicity (CDC); Fc receptor binding; antibody-depended cell-mediated cytotoxicity (ADCC); phagocytosis; down regulation of cell surface receptors (e.g., B cell receptor; BCR), etc. Such effector functions may require the Fc region to be operably linked to a binding domain (e.g., an antibody variable domain) and can be assessed using various assays (e.g., Fc binding assay, ADCC assays, CDC assays, target cell depletion from whole or fractionated blood samples, etc.).

A "native sequence Fc region" or "wild type Fc region" refers to an amino acid sequence that is identical to the amino acid sequence of an Fc region commonly found in nature. Exemplary native sequence feline Fc regions are shown in FIG. 2A and include, for example, a native sequence of feline IgG1a Fc region.

A "variant Fc region" comprises an amino acid sequence that differs from that of a native sequence Fc region (or fragment thereof) by virtue of at least one "amino acid substitution" as defined herein. In preferred embodiments, the variant Fc region has at least one amino acid substitution compared to a native sequence Fc region or in the Fc region of a parent polypeptide, preferably 1, 2, 3, 4 or 5 amino acid substitutions in a native sequence Fc region or in the Fc region of the parent polypeptide. In an alternative embodiment, a variant Fc region may be generated according to the methods herein disclosed and this variant Fc region can be fused to a heterologous polypeptide of choice, such as an antibody variable domain or a non-antibody polypeptide, e.g., binding domain of a receptor or ligand.

As used herein, the term "derivative" in the context of polypeptides refers to a polypeptide that comprises and amino acid sequence which has been altered by introduction of an amino acid residue substitution. The term "derivative" as used herein also refers to a polypeptide which has been modified by the covalent attachment of any type of molecule to the polypeptide. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative polypeptide may be produced by chemical modifications using techniques known to those of skill in the art, including, but not limited to specific chemical cleavage, acetylation, formylation, metabolic synthesis of tunicamycin, etc. Further, a derivative polypeptide possesses a similar or identical function as the polypeptide from which it was derived. It is understood that a polypeptide comprising a variant Fc region of the present invention may be a derivative as defined herein, preferably the derivatization occurs within the Fc region.

"Substantially of feline origin" as used herein in reference to a polypeptide (e.g., an Fc region or a monoclonal antibody), indicates the polypeptide has an amino acid sequence at least 80%, at least 85%, more preferably at least 90%, 91%, 92%, 93%, 94% or even more preferably at least 95%, 95%, 97%, 98% or 99% homologous to that of a native feline amino polypeptide.

The terms "Fc receptor" or "FcR" are used to describe a receptor that binds to an Fc region (e.g., the Fc region of an antibody). The preferred FcR is a native sequence FcR. Moreover, a preferred FcR is one which binds an IgG antibody (a gamma receptor) and includes receptors of the Fc gamma RI, Fc gamma RII, Fc gamma RIII subclasses, including allelic variants and alternatively spliced forms of these receptors. Another preferred FcR includes the neonatal receptor, FcRn, which is responsible for the transfer of maternal IgGs to the fetus (Guyer et al., J. Immunol. 117:587 (1976) and Kim et al., J. Immunol. 24:249 (1994)). Other FcRs, including those to be identified in the future, are encompassed by the term "FcR" herein.

The phrase "antibody-dependent cell-mediated cytotoxicity" and "ADCC" refer to a cell-mediated reaction in which nonspecific cytotoxic cells (e.g., nonspecific) that express FcRs (e.g., Natural Killer ("NK") cells, neutrophils, and macrophages) recognize bound antibody on a target cell and subsequently cause lysis of the target cells. The primary cells for mediating ADCC, NK cells, express Fc gamma MIT only, whereas monocytes express Fc gamma RI, Fc gamma MI and Fc gamma MIT As used herein, the phrase "effector cells" refers to leukocytes (preferably feline) which express one or more FcRs and perform effector functions. Preferably, the cells express at least Fc gamma MIT and perform ADCC effector function. Examples of leukocytes which mediate ADCC include PBMC, NK cells, monocytes, cytotoxic T cells and neutrophils. The effector cells may be isolated from a native source (e.g., from blood or PBMCs).

A variant polypeptide with "altered" FcRn binding affinity is one which has either enhanced (i.e., increased, greater or higher) or diminished (i.e., reduced, decreased or lesser) FcRn binding affinity compared to the variant's parent polypeptide or to a polypeptide comprising a native Fc region when measured at pH 6.0. A variant polypeptide which displays increased binding or increased binding affinity to an FcRn binds FcRn with greater affinity than the parent polypeptide. A variant polypeptide which displays decreased binding or decreased binding affinity to an FcRn, binds FcRn with lower affinity than its parent polypeptide. Such variants which display decreased binding to an FcRn may possess little or no appreciable binding to an FcRn, e.g., 0-20% binding to the FcRn compared to a parent polypeptide. A variant polypeptide which binds an FcRn with "enhanced affinity" as compared to its parent polypeptide, is one which binds FcRn with higher binding affinity than the parent polypeptide, when the amounts of variant polypeptide and parent polypeptide in a binding assay are essentially the same, and all other conditions are identical. For example, a variant polypeptide with enhanced FcRn binding affinity may display from about 1.10 fold to about 100 fold (more typically from about 1.2 fold to about 50 fold) increase in FcRn binding affinity compared to the parent polypeptide, where FcRn binding affinity is determined, for example, in an ELISA assay or other method available to one of ordinary skill in the art.

As used herein, an "amino acid substitution" refers to the replacement of at least one existing amino acid residue in a given amino acid sequence with another different "replacement" amino acid residue. The replacement residue or residues may be "naturally occurring amino acid residues" (i.e., encoded by the genetic code) and selected from: alanine (Ala); arginine (Arg); asparagine (Asn); aspartic acid (Asp); cysteine (Cys); glutamine (Gln); glutamic acid (Glu); glycine (Gly); histidine (H is); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residues (s) in a polypeptide chain. Examples of non-naturally occurring amino acid residues include norleucine, ornithine, norvaline, homoserine and other amino acid residue analogues such as those described in Ellman et al. Meth. Enzym. 202: 301-336 (1991).

The term "assay signal" refers to the output from any method of detecting protein-protein interactions, including but not limited to, absorbance measurements from colorimetric assays, fluorescent intensity, or disintegrations per minute. Assay formats could include ELISA, facs, or other methods. A change in the "assay signal" may reflect a change in cell viability and/or a change in the kinetic off-rate, the kinetic on-rate, or both. A "higher assay signal" refers to the measured output number being larger than another number (e.g., a variant may have a higher (larger) measured number in an ELISA assay as compared to the parent polypeptide). A "lower" assay signal refers to the measured output number being smaller than another number (e.g., a variant may have a lower (smaller) measured number in an ELISA assay as compared to the parent polypeptide).

The term "binding affinity" refers to the equilibrium dissociation constant (expressed in units of concentration) associated with each Fc receptor-Fc binding interaction. The binding affinity is directly related to the ratio of the kinetic off-rate (generally reported in units of inverse time, e.g., seconds$^{-1}$) divided by the kinetic on-rate (generally reported in units of concentration per unit time, e.g., molar/second). In general it is not possible to unequivocally state whether changes in equilibrium dissociation constants are due to differences in on-rates, off-rates or both unless each of these parameters are experimentally determined (e.g., by BIA-CORE or SAPIDYNE measurements).

As used herein, the term "hinge region" refers to the stretch of amino acids, for example, in feline IgG1a (e.g. stretching from position 216 to position 230 of feline IgG1a). Hinge regions of other IgG isotypes may be aligned with the IgG sequence by placing the first and last cysteine residues forming inter-heavy chain disulfide (S-S) bonds in the same positions.

"Clq" is a polypeptide that includes a binding site for the Fc region of an immunoglobulin. Clq together with two serine proteases, Clr and Cls, forms the complex Cl, the first component of the CDC pathway.

As used herein, the term "antibody" is used interchangeably with "immunoglobulin" or "Ig," is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity or functional activity. Single chain antibodies, and chimeric, feline, or felinized antibodies, as well as chimeric or CDR-grafted single chain antibodies, and the like, comprising portions derived from different species, are also encompassed by the present invention and the term "antibody". The various portions of these antibodies can be joined together chemically by conventional techniques, synthetically, or can be prepared as a contiguous protein using genetic engineering techniques. For example, nucleic acids encoding a chimeric or felinized chain can be expressed to produce a contiguous protein. See, e.g., U.S. Pat. Nos. 4,816,567; 4,816,397; WO 86/01533; U.S. Pat. Nos. 5,225, 539; and 5,585,089 and 5,698,762. See also, Newman, R. et al. BioTechnology, 10: 1455-1460, 1993, regarding primatized antibody, and Ladner et al., U.S. Pat. No. 4,946,778 and Bird, R. E. et al., Science, 242:423-426, 1988, regarding single chain antibodies. It is understood that all forms of the antibodies comprising an Fc region (or portion thereof) are encompassed herein within the term "antibody." Furthermore, the antibody may be labeled with a detectable label, immobilized on a solid phase and/or conjugated with a heterologous compound (e.g., an enzyme or toxin) according to methods known in the art.

As used herein, the term "antibody fragments" refers to a portion of an intact antibody. Examples of antibody fragments include, but are not limited to, linear antibodies; single-chain antibody molecules; Fc or Fc' peptides, Fab and Fab fragments, and multispecific antibodies formed from antibody fragments. The antibody fragments preferably retain at least part of the hinge and optionally the CH1 region of an IgG heavy chain. In other preferred embodiments, the antibody fragments comprise at least a portion of the CH2 region or the entire CH2 region.

As used herein, the term "functional fragment", when used in reference to a monoclonal antibody, is intended to refer to a portion of the monoclonal antibody that still retains a functional activity. A functional activity can be, for example, antigen binding activity or specificity, receptor binding activity or specificity, effector function activity and the like. Monoclonal antibody functional fragments include, for example, individual heavy or light chains and fragments thereof, such as VL, VH and Fd; monovalent fragments, such as Fv, Fab, and Fab'; bivalent fragments such as F(ab')2; single chain Fv (scFv); and Fc fragments. Such terms are described in, for example, Harlowe and Lane, Antibodies: A Laboratory Manual, Cold Spring Harbor Laboratory, New York (1989); Molec. Biology and Biotechnology: A Comprehensive Desk Reference (Myers, R. A. (ed.), New York: VCH Publisher, Inc.); Huston et al., Cell Biophysics, 22:189-224 (1993); Pluckthun and Skerra, Meth. Enzymol., 178:497-515 (1989) and in Day, E. D., Advanced Immunochemistry, Second Ed., Wiley-Liss, Inc., New York, N.Y. (1990). The term functional fragment is intended to include, for example, fragments produced by protease digestion or reduction of a monoclonal antibody and by recombinant DNA methods known to those skilled in the art.

As used herein, the term "fragment" refers to a polypeptide comprising an amino acid sequence of at least 5, 15, 20, 25, 40, 50, 70, 90, 100 or more contiguous amino acid residues of the amino acid sequence of another polypeptide. In a preferred embodiment, a fragment of a polypeptide retains at least one function of the full-length polypeptide.

As used herein, the term "chimeric antibody" includes monovalent, divalent or polyvalent immunoglobulins. A monovalent chimeric antibody is a dimer formed by a chimeric heavy chain associated through disulfide bridges with a chimeric light chain. A divalent chimeric antibody is a tetramer formed by two heavy chain-light chain dimers associated through at least one disulfide bridge. A chimeric heavy chain of an antibody for use in feline comprises an antigen-binding region derived from the heavy chain of a non-feline antibody, which is linked to at least a portion of a feline heavy chain constant region, such as CH1 or CH2. A chimeric light chain of an antibody for use in feline comprises an antigen binding region derived from the light chain of a non-feline antibody, linked to at least a portion of a feline light chain constant region (CL). Antibodies, fragments or derivatives having chimeric heavy chains and light chains of the same or different variable region binding specificity, can also be prepared by appropriate association of the individual polypeptide chains, according to known method steps. With this approach, hosts expressing chimeric heavy chains are separately cultured from hosts expressing chimeric light chains, and the immunoglobulin chains are separately recovered and then associated. Alternatively, the hosts can be co-cultured and the chains allowed to associate spontaneously in the culture medium, followed by recovery of the assembled immunoglobulin or fragment or both the heavy and light chains can be expressed in the same host cell. Methods for producing chimeric antibodies are well known in the art (see, e.g., U.S. Pat. Nos. 6,284,471; 5,807,715; 4,816,567; and 4,816,397).

As used herein, "felinized" forms of non-feline (e.g., murine) antibodies (i.e., felinized antibodies) are antibodies that contain minimal sequence, or no sequence, derived from non-feline immunoglobulin. For the most part, felinized antibodies are feline immunoglobulins (recipient antibody) in which residues from a hypervariable region of the recipient are replaced by residues from a hypervariable region of a non-feline species (donor antibody) such as mouse, rat, rabbit, human or nonhuman primate having the desired specificity, affinity, and capacity. In some instances, framework region (FR) residues of the feline immunoglobulin are replaced by corresponding non-feline residues. Furthermore, felinized antibodies may comprise residues that are not found in the recipient antibody or in the donor antibody. These modifications are generally made to further refine antibody performance. In general, the felinized antibody will comprise substantially all of at least one, and typically two, variable domains, in which all or substantially all of the hypervariable loops (CDRs) correspond to those of a non-feline immunoglobulin and all or substantially all of the FR residues are those of a feline immunoglobulin sequence. The felinized antibody may also comprise at least a portion of an immunoglobulin constant region (Fc), typically that of a feline immunoglobulin.

As used herein, the term "immunoadhesin" designates antibody-like molecules which combine the binding domain of a heterologous "adhesin" protein (e.g., a receptor, ligand or enzyme) with an immunoglobulin constant domain. Structurally, immunoadhesins comprise a fusion of the adhesin amino acid sequence with the desired binding specificity which is other than the antigen recognition and binding site (antigen combining site) of an antibody (i.e., is "heterologous") with an immunoglobulin constant domain sequence.

As used herein, the term "ligand binding domain" refers to any native receptor or any region or derivative thereof retaining at least a qualitative ligand binding ability of a corresponding native receptor. In certain embodiments, the receptor is from a cell-surface polypeptide having an extra-cellular domain that is homologous to a member of the immunoglobulin supergenefamily. Other receptors, which are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules (e.g., E-, L-, and P-selectins).

As used herein, the term "receptor binding domain" refers to any native ligand for a receptor, including, e.g., cell adhesion molecules, or any region or derivative of such native ligand retaining at least a qualitative receptor binding ability of a corresponding native ligand.

As used herein, an "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or non-proteinaceous solutes. In certain embodiments, the iso-lated polypeptide is purified (1) to greater than 95% by weight of polypeptides as determined by the Lowry method, and preferably, more than 99% by weight, (2) to a degree sufficient to obtain at least 15 residues of N-terminal or internal amino acid sequence by use of a spinning cup sequenator, or (3) to homogeneity by SDS-page under reducing or nonreducing conditions using Coomassie blue or silver stain. Isolated polypeptide includes the polypeptide in situ within recombinant cells since at least one component of the polypeptide's natural environment will not be present. Ordinarily, however, isolated polypeptide will be prepared by a least one purification step.

As used herein, the term "disorder" and "disease" are used interchangeably to refer to any condition that would benefit from treatment with a variant polypeptide (a polypeptide comprising a variant Fc region of the invention), including chronic and acute disorders or diseases (e.g., pathological conditions that predispose a patient to a particular disorder).

As used herein, the term "receptor" refers to a polypeptide capable of binding at least one ligand. The preferred receptor is a cell-surface or soluble receptor having an extracellular ligand-binding domain and, optionally, other domains (e.g., transmembrane domain, intracellular domain and/or mem-brane anchor). A receptor to be evaluated in an assay described herein may be an intact receptor or a fragment or derivative thereof (e.g. a fusion protein comprising the binding domain of the receptor fused to one or more heterologous polypeptides). Moreover, the receptor to be evaluated for its binding properties may be present in a cell or isolated and optionally coated on an assay plate or some other solid phase or labeled directly and used as a probe.

Feline Wildtype IgG

Feline IgGs are well known in the art and fully described, for example, in Strietzel et al., 2014, *Vet Immunol Immunopathol.*, vol. 158(3-4), pages 214-223. In one embodi-ment, feline IgG is IgG1a. In another embodiment, feline IgG is IgG1b. In yet another embodiment, feline IgG is IgG2. In a particular embodiment, feline IgG is IgG1a.

The amino acid and nucleic acid sequences of IgG1a, IgG1b, and IgG2 are also well known in the art.

In one example, IgG of the invention comprises a constant domain, for example, CH1, CH2, or CH3 domains, or a combination thereof. In another example, the constant domain of the invention comprises Fc region, including, for example, CH2 or CH3 domains or a combination thereof.

In a particular example, the wild-type constant domain comprises the amino acid sequence set forth in SEQ ID NO.: 3. In some embodiments, the wild-type IgG constant domain is a homologue, a variant, an isomer, or a functional frag-ment of SEQ ID NO.: 3, but without any mutation at position 428 or 434. Each possibility represents a separate embodi-ment of the present invention.

IgGs contant domains also include polypeptides with amino acid sequences substantially similar to the amino acid sequence of the heavy and/or light chain. Substantially the same amino acid sequence is defined herein as a sequence with at least 70%, 75%, 80%, 85%, 90%, 95%, or 99% identity to a compared amino acid sequence, as determined by the FASTA search method in accordance with Pearson and Lipman, Proc. Natl. Acad. Sci. USA 85:2444-2448 (1988).

The present invention also includes nucleic acid mol-ecules that encode IgGs or portion thereof, described herein. In one embodiment, the nucleic acids may encode an anti-body heavy chain comprising, for example, CH1, CH2, CH3 regions, or a combination thereof. In another embodiment, the nucleic acids may encode an antibody heavy chain comprising, for example, any one of the VH regions or a portion thereof, or any one of the VH CDRs, including any variants thereof. The invention also includes nucleic acid molecules that encode an antibody light chain comprising, for example, any one of the CL regions or a portion thereof, any one of the VL regions or a portion thereof or any one of the VL CDRs, including any variants thereof. In certain embodiments, the nucleic acid encodes both a heavy and light chain, or portions thereof.

The amino acid sequence of the wild-type constant domain set forth in SEQ ID NO.: 3 is encoded by the nucleic acid sequence set forth in in SEQ ID NO.: 4.

Modified Feline IgG

The inventors of the instant application have found that substituting the amino acid residue serine (Ser or S) at position 428 or 434 with another amino acid surprisingly and unexpectedly enhanced the affinity to FcRn and increased the half-life of IgG. The terms, position 428 or position 434, as used herein, refers to a position numbered according to the EU index as in Kabat (Kabat et al., Sequences of Proteins of Immunological Interest, 5th Ed. Public Health Service, National Institutes of Health, Bethesda, Md. (1991)).

Accordingly, in one embodiment, the invention provides a modified IgG comprising: a feline IgG constant domain comprising at least one amino acid substitution relative to a wild-type feline IgG constant domain, wherein said substitution is at amino acid residue 428, numbered according to the EU index as in Kabat. The serine at position 428 can be substituted with any other amino acid. For example, the serine at position 428 can be substituted with leucine (i.e., S428L), asparagine (i.e., S428N), alanine (i.e., S428A), phenylalanine (i.e., S428F), glycine (i.e., S428G), isoleucine (i.e., S428I), lysine (i.e., S428K), histidine (i.e., S428H), methionine (i.e., S428M), glutamine (i.e., S428Q), arginine (i.e., S428R), threonine (i.e., S428T), valine (i.e., S428V), tryptophan (i.e., S428W), tyrosine (i.e., S428Y), cysteine (i.e., S428C), aspartic acid (i.e., S428D), glutamic acid (i.e., S428E), or proline (i.e., S428P). In a particular embodiment, the substitution is a substitution with leucine (i.e., S428L).

In a particular example, the mutant constant domain of the invention comprises the amino acid sequence set forth in SEQ ID NO.: 1. In some embodiments, the mutant IgG constant domain is a homologue, a variant, an isomer, or a functional fragment of SEQ ID NO.: 1, but with mutation at position 428. Each possibility represents a separate embodiment of the present invention.

The amino acid sequence of the mutant constant domain set forth in SEQ ID NO.: 1 is encoded by its corresponding mutant nucleic acid sequence, for example, a mutant form of the nucleic acid sequence set forth in in SEQ ID NO.: 4.

In another embodiment, the invention provides a modified IgG comprising: a feline IgG constant domain comprising at least one amino acid substitution relative to a wild-type feline IgG constant domain, wherein said substitution is at amino acid residue 434, numbered according to the EU index as in Kabat. The serine at position 434 can be substituted with any other amino acid. For example, the serine at position 434 can be substituted with histidine (i.e., S434H), asparagine (i.e., S434N), alanine (i.e., S434A), phenylalanine (i.e., S434F), glycine (i.e., S434G), isoleucine (i.e., S434I), lysine (i.e., S434K), leucine (i.e., S434L), methionine (i.e., S434M), glutamine (i.e., S434Q), arginine (i.e., S434R), threonine (i.e., S434T), valine (i.e., S434V), tryptophan (i.e., S434W), tyrosine (i.e., S434Y), cysteine (i.e., S434C), aspartic acid (i.e., S434D), glutamic acid (i.e., S434E), or proline (i.e., S434P). In a particular embodiment, the substitution is a substitution with histidine (i.e., S434H).

In a particular example, the mutant constant domain of the invention comprises the amino acid sequence set forth in SEQ ID NO.: 2. In some embodiments, the mutant IgG constant domain is a homologue, a variant, an isomer, or a functional fragment of SEQ ID NO.: 2, but with mutation at position 434. Each possibility represents a separate embodiment of the present invention.

The amino acid sequence of the mutant constant domain set forth in SEQ ID NO.: 2 is encoded by its corresponding mutant nucleic acid sequence, for example, a mutant form of the nucleic acid sequence set forth in in SEQ ID NO.: 4.

In some embodiments, the feline IgG constant domain comprises substitutions of serines at both 428 and 434 positions with leucine and histidine, respectively.

The modified IgG of the invention provides the half-life for a period ranging from about 8 days to about 26 days. In one embodiment, the modified IgG of the invention provides the half-life for about 10, 12, 15, 17, 20, 23, or 26 days. In a particular embodiment, the modified IgG of the invention provides the half-life for more than 10 days.

Methods for Making Antibody Molecules of the Invention

Methods for making antibody molecules are well known in the art and fully described in U.S. Pat. Nos. 8,394,925; 8,088,376; 8,546,543; 10,336,818; and 9,803,023 and U.S. Patent Application Publication 20060067930, which are incorporated by reference herein in their entirety. Any suitable method, process, or technique, known to one of skilled in the art, can be used. An antibody molecule having a variant Fc region of the invention may be generated according to the methods well known in the art. In some embodiments, the variant Fc region can be fused to a heterologous polypeptide of choice, such as an antibody variable domain or binding domain of a receptor or ligand.

With the advent of methods of molecular biology and recombinant technology, a person of skilled in the art can produce antibody and antibody-like molecules by recombinant means and thereby generate gene sequences that code for specific amino acid sequences found in the polypeptide structure of the antibodies. Such antibodies can be produced by either cloning the gene sequences encoding the polypeptide chains of said antibodies or by direct synthesis of said polypeptide chains, with assembly of the synthesized chains to form active tetrameric (H2L2) structures with affinity for specific epitopes and antigenic determinants. This has permitted the ready production of antibodies having sequences characteristic of neutralizing antibodies from different species and sources.

Regardless of the source of the antibodies, or how they are recombinantly constructed, or how they are synthesized, in vitro or in vivo, using transgenic animals, large cell cultures of laboratory or commercial size, using transgenic plants, or by direct chemical synthesis employing no living organisms at any stage of the process, all antibodies have a similar overall 3 dimensional structure. This structure is often given as H2L2 and refers to the fact that antibodies commonly comprise two light (L) amino acid chains and 2 heavy (H) amino acid chains. Both chains have regions capable of interacting with a structurally complementary antigenic target. The regions interacting with the target are referred to as "variable" or V" regions and are characterized by differences in amino acid sequence from antibodies of different antigenic specificity. The variable regions of either H or L chains contain the amino acid sequences capable of specifically binding to antigenic targets.

As used herein, the term "antigen binding region" refers to that portion of an antibody molecule which contains the amino acid residues that interact with an antigen and confer on the antibody its specificity and affinity for the antigen. The antibody binding region includes the "framework" amino acid residues necessary to maintain the proper conformation of the antigen-binding residues. Within the variable regions of the H or L chains that provide for the antigen binding regions are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure.

The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have three CDR regions, each non-contiguous with the others. In all mammalian species, antibody peptides contain constant (i.e., highly conserved) and variable regions, and, within the latter, there are the CDRs and the so-called "framework regions" made up of amino acid sequences within the variable region of the heavy or light chain but outside the CDRs.

The present invention further provides a vector including at least one of the nucleic acids described above. Because the genetic code is degenerate, more than one codon can be used to encode a particular amino acid. Using the genetic code, one or more different nucleotide sequences can be identified, each of which would be capable of encoding the amino acid. The probability that a particular oligonucleotide will, in fact, constitute the actual encoding sequence can be estimated by considering abnormal base pairing relationships and the frequency with which a particular codon is actually used (to encode a particular amino acid) in eukaryotic or prokaryotic cells expressing an antibody or portion. Such "codon usage rules" are disclosed by Lathe, et al., 183 J. Molec. Biol. 1-12 (1985). Using the "codon usage rules" of Lathe, a single nucleotide sequence, or a set of nucleotide sequences that contains a theoretical "most probable" nucleotide sequence capable of encoding feline IgG sequences can be identified. It is also intended that the antibody coding regions for use in the present invention could also be provided by altering existing antibody genes using standard molecular biological techniques that result in variants of the antibodies and peptides described herein. Such variants include, but are not limited to deletions, additions and substitutions in the amino acid sequence of the antibodies or peptides.

For example, one class of substitutions is conservative amino acid substitutions. Such substitutions are those that substitute a given amino acid in a feline antibody peptide by another amino acid of like characteristics. Typically seen as conservative substitutions are the replacements, one for another, among the aliphatic amino acids Ala, Val, Leu, and lie; interchange of the hydroxyl residues Ser and Thr, exchange of the acidic residues Asp and Glu, substitution between the amide residues Asn and Gin, exchange of the basic residues Lys and Arg, replacements among the aromatic residues Phe, Tyr, and the like. Guidance concerning which amino acid changes are likely to be phenotypically silent is found in Bowie et al., 247 *Science* 1306-10 (1990).

Variant feline antibodies or peptides may be fully functional or may lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis. Cunningham et al., 244 *Science* 1081-85 (1989). The latter procedure introduces single alanine mutations at every residue in the molecule. The resulting mutant molecules are then tested for biological activity such as epitope binding or in vitro ADCC activity. Sites that are critical for ligand-receptor binding can also be determined by structural analysis such as crystallography, nuclear magnetic resonance, or photoaffinity labeling. Smith et al., 224 *J Mol. Biol.* 899-904 (1992); de Vos et al., 255 *Science* 306-12 (1992).

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill in the art and have been described in great detail in the scientific literature. Several particularly common modifications, glycosylation, lipid attachment, sulfation, gamma-carboxylation of glutamic acid residues, hydroxylation and ADP ribosylation, for instance, are described in most basic texts, such as Proteins-Structure and Molecular Properties (2nd ed., T. E. Creighton, W. H. Freeman & Co., N.Y., 1993). Many detailed reviews are available on this subject, such as by Wold, Posttranslational Covalent Modification of proteins, 1-12 (Johnson, ed., Academic Press, N.Y., 1983); Seifter et al. 182 *Meth. Enzymol.* 626-46 (1990); and Rattan et al. 663 *Ann. NY Acad. Sci.* 48-62 (1992).

In another aspect, the invention provides antibody derivatives. A "derivative" of an antibody contains additional chemical moieties not normally a part of the protein. Covalent modifications of the protein are included within the scope of this invention. Such modifications may be introduced into the molecule by reacting targeted amino acid residues of the antibody with an organic derivatizing agent that is capable of reacting with selected side chains or terminal residues. For example, derivatization with bifunctional agents, well-known in the art, is useful for cross-linking the antibody or fragment to a water-insoluble support matrix or to other macromolecular carriers.

Derivatives also include radioactively labeled monoclonal antibodies that are labeled. For example, with radioactive iodine (251,1311), carbon (4C), sulfur (35S), indium, tritium ($H^3$) or the like; conjugates of monoclonal antibodies with biotin or avidin, with enzymes, such as horseradish peroxidase, alkaline phosphatase, beta-D-galactosidase, glucose oxidase, glucoamylase, carboxylic acid anhydrase, acetylcholine esterase, lysozyme, malate dehydrogenase or glucose 6-phosphate dehydrogenase; and also conjugates of monoclonal antibodies with bioluminescent agents (such as luciferase), chemoluminescent agents (such as acridine esters) or fluorescent agents (such as phycobiliproteins).

Another derivative bifunctional antibody of the invention is a bispecific antibody, generated by combining parts of two separate antibodies that recognize two different antigenic groups. This may be achieved by crosslinking or recombinant techniques. Additionally, moieties may be added to the antibody or a portion thereof to increase half-life in vivo (e.g., by lengthening the time to clearance from the blood stream. Such techniques include, for example, adding PEG moieties (also termed pegylation), and are well-known in the art. See U.S. Patent. Appl. Pub. No. 20030031671.

In some embodiments, the nucleic acids encoding a subject antibody are introduced directly into a host cell, and the cell is incubated under conditions sufficient to induce expression of the encoded antibody. After the subject nucleic acids have been introduced into a cell, the cell is typically incubated, normally at 37° C., sometimes under selection, for a period of about 1-24 hours in order to allow for the expression of the antibody. In one embodiment, the antibody is secreted into the supernatant of the media in which the cell is growing. Traditionally, monoclonal antibodies have been produced as native molecules in murine hybridoma lines. In addition to that technology, the present invention provides for recombinant DNA expression of the antibodies. This allows the production of antibodies, as well as a spectrum of antibody derivatives and fusion proteins in a host species of choice.

A nucleic acid sequence encoding at least one antibody, portion or polypeptide of the invention may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., MOLECULAR CLONING, LAB. MANUAL, (Cold Spring Harbor Lab. Press, N Y, 1982 and 1989), and Ausubel et al. 1993 supra, may be used to construct nucleic acid sequences which encode an antibody molecule or antigen binding region thereof.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides or antibody portions in recoverable amounts. The precise nature of the regulatory regions needed for gene expression may vary from organism to organism, as is well known in the analogous art. See, e.g., Sambrook et al., 2001 supra; Ausubel et al., 1993 supra.

The present invention accordingly encompasses the expression of an antibody or peptide, in either prokaryotic or eukaryotic cells. Suitable hosts include bacterial or eukaryotic hosts including bacteria, yeast, insects, fungi, bird and mammalian cells either in vivo, or in situ, or host cells of mammalian, insect, bird or yeast origin. The mammalian cell or tissue may be of human, primate, hamster, rabbit, rodent, cow, pig, sheep, horse, goat, dog or cat origin. Any other suitable mammalian cell, known in the art, may also be used.

In one embodiment, the nucleotide sequence of the invention will be incorporated into a plasmid or viral vector capable of autonomous replication in the recipient host. Any of a wide variety of vectors may be employed for this purpose. See, e.g., Ausubel et al., 1993 supra. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in *E. coli* (such as, for example, pBR322, CoIE1, pSC101, pACYC 184, .pi.vX). Such plasmids are, for example, disclosed by Maniatis et at, 1989 supra; Ausubel et al, 1993 supra. Bacillus plasmids include pC194, pC221, pT127, etc. Such plasmids are disclosed by Gryczan, in THE MOLEC. BIO. OF THE BACILLI 307-329 (Academic Press, N Y, 1982). Suitable Streptomyces plasmids include 01101 (Kendall et al., 169 J. Bacteriol. 4177-83 (1987), and Streptomyces bacteriophages such as phLC31 (Chater et al., in SIXTH INT'L SYMPOSIUM ON ACTINOMYCETALES BIO. 45-54 (Akademiai Kaido, Budapest, Hungary 1986). Pseudomonas plasmids are reviewed in John et al., 8 Rev. Infect. Dis. 693-704 (1986); lzaki, 33 Jpn. J. Bacteriol. 729-42 (1978); and Ausubel et al., 1993 supra.

Alternatively, gene expression elements useful for the expression of cDNA encoding antibodies or peptides include, but are not limited to, (a) viral transcription promoters and their enhancer elements, such as the SV40 early promoter (Okayama et al., 3 Mol. Cell. Biol. 280 (1983), Rous sarcoma virus LTR (Gorman et al., 79 Proc. Natl. Acad. Sci., USA 6777 (1982), and Moloney murine leukemia virus LTR (Grosschedl et al., 41 Cell 885 (1985); (b) splice regions and polyadenylation sites such as those derived from the SV40 late region (Okayarea et al., 1983), and (c) polyadenylation sites such as in SV40 (Okayama et al., 1983).

Immunoglobulin cDNA genes can be expressed as described by Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements. For immunoglobulin genes comprised of part cDNA, part genomic DNA (Whittle et al., 1 Protein Engin. 499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In one embodiment, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene can be assembled in, or inserted into, an expression vector. Recipient cells capable of expressing the immunoglobulin chain gene product are then transfected singly with a peptide or H or L chain-encoding gene, or are co-transfected with H and L chain gene. The transfected recipient cells are cultured under conditions that permit expression of the incorporated genes and the expressed immunoglobulin chains or intact antibodies or fragments are recovered from the culture.

In one embodiment, the fused genes encoding the peptide or H and L chains, or portions thereof are assembled in separate expression vectors that are then used to cotransfect a recipient cell. Alternatively the fused genes encoding the H and L chains can be assembled on the same expression vector. For transfection of the expression vectors and production of the antibody, the recipient cell line may be a myeloma cell. Myeloma cells can synthesize, assemble and secrete immunoglobulins encoded by transfected immunoglobulin genes and possess the mechanism for glycosylation of the immunoglobulin. Myeloma cells can be grown in culture or in the peritoneal cavity of a mouse, where secreted immunoglobulin can be obtained from ascites fluid. Other suitable recipient cells include lymphoid cells such as B lymphocytes of feline or non-feline origin, hybridoma cells of feline or non-feline origin, or interspecies heterohybridoma cells.

The expression vector carrying an antibody construct or polypeptide of the invention can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment. Johnston et al., 240 *Science* 1538 (1988).

Yeast may provide substantial advantages over bacteria for the production of immunoglobulin H and L chains. Yeasts carry out post-translational peptide modifications including glycosylation. A number of recombinant DNA strategies now exist which utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Int'l Conference on Yeast, Genetics & Molec. Biol. (Montpelier, France, 1982).

Yeast gene expression systems can be routinely evaluated for the levels of production, secretion and the stability of peptides, antibodies, fragments and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast. See Vol. II DNA Cloning, 45-66, (Glover, ed.,) IRL Press, Oxford, U K 1985).

Bacterial strains can also be utilized as hosts for the production of antibody molecules or peptides described by this invention. Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of antibodies, fragments and regions or antibody chains encoded by the cloned immunoglobulin cDNAs in bacteria (see Glover, 1985 supra; Ausubel, 1993 supra; Sambrook, 2001 supra; Colligan et al., eds. Current Protocols in Immunology, John Wiley & Sons, NY, N.Y. (1994-2001); Colligan et al., eds. Current Protocols in Protein Science, John Wiley & Sons, NY, N.Y. (1997-2001).

Host mammalian cells may be grown in vitro or in vivo. Mammalian cells provide posttranslational modifications to immunoglobulin protein molecules including leader peptide removal, folding and assembly of H and L chains, glycosylation of the antibody molecules, and secretion of functional antibody protein. Mammalian cells which can be useful as hosts for the production of antibody proteins, in addition to the cells of lymphoid origin described above, include cells of fibroblast origin, such as Vero (ATCC CRL 81) or CHO-K 1 (ATCC CRL 61) cells. Many vector systems are available for the expression of cloned peptides H and L chain genes in mammalian cells (see Glover, 1985 supra). Different approaches can be followed to obtain complete H2L2 antibodies. It is possible to co-express H and L chains in the same cells to achieve intracellular association and linkage of H and L chains into complete tetrameric H2L2 antibodies and/or peptides. The co-expression can occur by using either the same or different plasmids in the same host. Genes for both H and L chains and/or peptides can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. cell lines producing peptides and/or H2L2 molecules via either route could be transfected with plasmids encoding additional copies of peptides, H, L, or H plus L chains in conjunction with additional selectable markers to generate cell lines with enhanced properties, such as higher production of assembled H2L2 antibody molecules or enhanced stability of the transfected cell lines.

For long-term, high-yield production of recombinant antibodies, stable expression may be used. For example, cell lines, which stably express the antibody molecule may be engineered. Rather than using expression vectors which contain viral origins of replication, host cells can be transformed with immunoglobulin expression cassettes and a selectable marker. Following the introduction of the foreign DNA, engineered cells may be allowed to grow for 1-2 days in enriched media, and then are switched to a selective media. The selectable marker in the recombinant plasmid confers resistance to the selection and allows cells to stably integrate the plasmid into a chromosome and grow to form foci which in turn can be cloned and expanded into cell lines. Such engineered cell lines may be particularly useful in screening and evaluation of compounds/components that interact directly or indirectly with the antibody molecule.

Once an antibody of the invention has been produced, it may be purified by any method known in the art for purification of an immunoglobulin molecule, for example, by chromatography (e.g., ion exchange, affinity, particularly affinity for the specific antigen after Protein A, and sizing column chromatography), centrifugation, differential solubility, or by any other standard technique for the purification of proteins. In many embodiments, antibodies are secreted from the cell into culture medium and harvested from the culture medium.

In another aspect, the invention provides an antibody comprising: a feline IgG constant domain comprising at least one amino acid substitution relative to a wild-type feline IgG constant domain, wherein said substitution is at amino acid residue 428, 434, or a combination thereof. In one embodiment, the substitution is a substitution of serine at position 428 with leucine (S428L). In another embodiment, the substitution is a substitution of serine at position 434 with histidine (S434H).

The antibody having the substitution can be any suitable antibody known to one of skilled in the art. In one example, the antibody is an anti-IL31 antibody. In another example, the antibody is an anti-NGF antibody. In yet another example, the antibody is an anti-TGFβ antibody.

Anti-IL31 antibody, without the substitution described herein, is well known in the art and fully described in, for example, U.S. Pat. Nos. 10,526,405; 10,421,807; 9,206,253; and 8,790,651. Also, anti-NGF antibody, without the substitution described herein, is also well known in the art and fully described in, for example, U.S. Pat. Nos. 10,125,192; 10,093,725; 9,951,128; 9,617,334; and 9,505,829. Furthermore, anti-TGFβ antibody, without the substitution described herein, is also well known in the art and fully described in, for example, U.S. patent applications Ser. Nos. 63/248,679 and 63/036,092 and PCT International Patent Application PCT/US2021/036347.

In one embodiment, the anti-IL31 antibody of the invention (i.e., antibody having the substitution) reduces, inhibits, or neutralizes an IL-31-mediated pruritic or allergic condition. In another embodiment, the anti-IL31 antibody of the invention reduces, inhibits, or neutralizes IL-31 activity in a cat.

VL, VH, and CDR sequences of the anti-IL31 antibodies are well known in the art and fully described in, for example, U.S. Pat. Nos. 10,526,405; 10,421,807; 9,206,253; and 8,790,651. In one example, the anti-IL31 antibody of the invention may include at least one of the following complementary determining region (CDR) sequences: variable heavy (VH)-CDR1 of SEQ ID NO: 15, VH-CDR2 of SEQ ID NO: 16, VH-CDR3 of SEQ ID NO: 17, variable light (VL)-CDR1 of SEQ ID NO: 20, VL-CDR2 of SEQ ID NO: 21, and VL-CDR3 of SEQ ID NO: 22. In some embodiments, the anti-IL31 antibody of the invention may include at least one CDR described herein.

In one embodiment, the anti-IL31 antibody of the invention may include a variable light chain comprising the amino acid sequence set forth in SEQ ID NO: 19. In another embodiment, the anti-IL31 antibody of the invention may include a variable heavy chain comprising the amino acid sequence set forth in SEQ ID NO: 14.

In one embodiment, the mutant anti-NGF antibody of the invention (i.e., antibody having the substitution) reduces, inhibits, or neutralizes NGF activity in an animal, and/or enhanced ability to inhibit NGF binding to Trk A and p'75, in order to treat an NGF-mediated pain or condition.

VL, VH, and CDR sequences of the anti-NGF antibodies are also well known in the art and fully described in, for example, U.S. Pat. Nos. 10,125,192; 10,093,725; 9,951,128; 9,617,334; and 9,505,829. In one example, the anti-NGF antibody of the invention may include at least one of the following complementary determining region (CDR) sequences: variable heavy (VH)-CDR1 of SEQ ID NO: 24, VH-CDR2 of SEQ ID NO: 25, VH-CDR3 of SEQ ID NO: 26, variable light (VL)-CDR1 of SEQ ID NO: 28, VL-CDR2 of SEQ ID NO: 29, and VL-CDR3 of SEQ ID NO: 30.

In another example, the anti-NGF antibody of the invention may include at least one of the following complementary determining region (CDR) sequences: variable heavy (VH)-CDR1 of SEQ ID NO: 32, VH-CDR2 of SEQ ID NO: 33, VH-CDR3 of SEQ ID NO: 34, variable light (VL)-CDR1 of SEQ ID NO: 36, VL-CDR2 of SEQ ID NO: 37, and VL-CDR3 of SEQ ID NO: 38.

In one embodiment, the anti-NGF antibody of the invention may include a variable light chain comprising the amino acid sequence set forth in SEQ ID NO: 27 or 35.

In another embodiment, the anti-NGF antibody of the invention may include a variable heavy chain comprising a variable sequence of the amino acid sequence set forth in SEQ ID NO: 23 or 31.

In one embodiment, the anti-TGFβ antibody of the invention (i.e., antibody having the substitution) reduces, inhibits, or neutralizes an TGFβ-mediated disease or condition, for example, chronic kidney disease. In another embodiment, the anti-TGFβ antibody of the invention reduces, inhibits, or neutralizes TGFβ activity in a cat. The anti-TGFβ antibody of the invention can bind to TGFβ1, 2, 3, or a combination thereof. For instance, in one embodiment, the anti-TGFβ antibody of the invention binds to TGFβ1. In another embodiment, the anti-TGFβ antibody of the invention binds to TGFβ2. In another embodiment, the anti-TGFβ antibody of the invention binds to TGFβ3. In yet another embodiment, the anti-TGFβ antibody of the invention binds to TGFβ1, TGFβ2, TGFβ3, or a combination thereof.

VL, VH, and CDR sequences of the anti-TGFβ antibodies are well known in the art and fully described in, for example, U.S. patent applications Ser. Nos. 63/036,092 and 63/248, 679 and PCT International Patent Application PCT/US2021/036347. In one example, the anti-TGFβ antibody of the invention may include at least one of the following combinations of complementary determining region (CDR) sequences: (1) ZTS-310: variable heavy (VH)-CDR1 of SEQ ID NO: 39, VH-CDR2 of SEQ ID NO: 40, VH-CDR3 of SEQ ID NO: 41, variable light (VL)-CDR1 of SEQ ID NO: 42, VL-CDR2 of SEQ ID NO: 43, and VL-CDR3 of SEQ ID NO: 44; or (2) ZTS-120-1: variable heavy (VH)-CDR1 of SEQ ID NO: 49, VH-CDR2 of SEQ ID NO: 50, VH-CDR3 of SEQ ID NO: 51, variable light (VL)-CDR1 of SEQ ID NO: 52, VL-CDR2 of SEQ ID NO: 53, and VL-CDR3 of SEQ ID NO: 54; or (3) ZTS-120-2: VH-CDR1 of SEQ ID NO: 59, VH-CDR2 of SEQ ID NO: 60, VH-CDR3 of SEQ ID NO: 61, VL-CDR1 of SEQ ID NO: 62, VL-CDR2 of SEQ ID NO: 63, and VL-CDR3 of SEQ ID NO: 64; or (4) ZTS-120-3: VH-CDR1 of SEQ ID NO: 69, VH-CDR2 of SEQ ID NO: 70, VH-CDR3 of SEQ ID NO: 71, VL-CDR1 of SEQ ID NO: 72, VL-CDR2 of SEQ ID NO: 73, and VL-CDR3 of SEQ ID NO: 74; or (5) ZTS-120-4: VH-CDR1 of SEQ ID NO: 79, VH-CDR2 of SEQ ID NO: 80, VH-CDR3 of SEQ ID NO: 81, VL-CDR1 of SEQ ID NO: 82, VL-CDR2 of SEQ ID NO: 83, and VL-CDR3 of SEQ ID NO: 84; or (6) ZTS-120-5: VH-CDR1 of SEQ ID NO: 89, VH-CDR2 of SEQ ID NO: 90, VH-CDR3 of SEQ ID NO: 91, VL-CDR1 of SEQ ID NO: 92, VL-CDR2 of SEQ ID NO: 93, and VL-CDR3 of SEQ ID NO: 94; or (7) ZTS-120-6: VH-CDR1 of SEQ ID NO: 99, VH-CDR2 of SEQ ID NO: 100, VH-CDR3 of SEQ ID NO: 101, VL-CDR1 of SEQ ID NO: 102, VL-CDR2 of SEQ ID NO: 103, and VL-CDR3 of SEQ ID NO: 104; or (8) ZTS-120-7: VH-CDR1 of SEQ ID NO: 109, VH-CDR2 of SEQ ID NO: 110, VH-CDR3 of SEQ ID NO: 111, VL-CDR1 of SEQ ID NO: 112, VL-CDR2 of SEQ ID NO: 113, and VL-CDR3 of SEQ ID NO: 114; or (9) ZTS-120-8: VH-CDR1 of SEQ ID NO: 119, VH-CDR2 of SEQ ID NO: 120, VH-CDR3 of SEQ ID NO: 121, VL-CDR1 of SEQ ID NO: 122, VL-CDR2 of SEQ ID NO: 123, and VL-CDR3 of SEQ ID NO: 124; or

(10) ZTS-120-9: VH-CDR1 of SEQ ID NO: 129, VH-CDR2 of SEQ ID NO: 130, VH-CDR3 of SEQ ID NO: 131, VL-CDR1 of SEQ ID NO: 132, VL-CDR2 of SEQ ID NO: 133, and VL-CDR3 of SEQ ID NO: 134.

In some embodiments, the anti-TGFβ antibody of the invention may include at least one CDR described herein.

In one embodiment, the anti-TGFβ antibody of the invention may include a variable heavy chain comprising the amino acid sequence set forth in SEQ ID NO: 45 (ZTS-310), SEQ ID NO: 55 (ZTS-120-1), SEQ ID NO: 65 (ZTS-120-2), SEQ ID NO: 75 (ZTS-120-3), SEQ ID NO: 85 (ZTS-120-4), SEQ ID NO: 95 (ZTS-120-5), SEQ ID NO: 105 (ZTS-120-6), SEQ ID NO: 115 (ZTS-120-7), SEQ ID NO: 125 (ZTS-120-8), or SEQ ID NO: 135 (ZTS-120-9).

In another embodiment, the anti-TGFβ antibody of the invention may include a variable light chain comprising the amino acid sequence set forth in SEQ ID NO: 47 (ZTS-310), SEQ ID NO: 57 (ZTS-120-1), SEQ ID NO: 67 (ZTS-120-2), SEQ ID NO: 77 (ZTS-120-3), SEQ ID NO: 87 (ZTS-120-4), SEQ ID NO: 97 (ZTS-120-5), SEQ ID NO: 107 (ZTS-120-6), SEQ ID NO: 117 (ZTS-120-7), SEQ ID NO: 127 (ZTS-120-8), or SEQ ID NO: 137 (ZTS-120-9).

Pharmaceutical and Veterinary Applications

The invention also provides a pharmaceutical composition comprising molecules of the invention and one or more pharmaceutically acceptable carriers. More specifically, the invention provides for a pharmaceutical composition comprising a pharmaceutically acceptable carrier or diluent and, as active ingredient, an antibody or peptide according to the invention.

"Pharmaceutically acceptable carriers" include any excipient which is nontoxic to the cell or animal being exposed thereto at the dosages and concentrations employed. The pharmaceutical composition may include one or additional therapeutic agents.

"Pharmaceutically acceptable" refers to those compounds, materials, compositions, and/or dosage forms which are, within the scope of sound medical judgment, suitable for contact with the tissues of animals without excessive toxicity, irritation, allergic response, or other problem complications commensurate with a reasonable benefit/risk ratio.

Pharmaceutically acceptable carriers include solvents, dispersion media, buffers, coatings, antibacterial and antifungal agents, wetting agents, preservatives, buggers, chelating agents, antioxidants, isotonic agents and absorption delaying agents.

Pharmaceutically acceptable carriers include water; saline; phosphate buffered saline; dextrose; glycerol; alcohols such as ethanol and isopropanol; phosphate, citrate and other organic acids; ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; EDTA; salt forming counterions such as sodium; and/or nonionic surfactants such as TWEEN, polyethylene glycol (PEG), and PLURONICS; isotonic agents such as sugars, polyalcohols such as mannitol and sorbitol, and sodium chloride; as well as combinations thereof.

The pharmaceutical compositions of the invention may be formulated in a variety of ways, including for example, liquid, semi-solid, or solid dosage forms, such as liquid solutions (e.g., injectable and infusible solutions), dispersions or suspensions, liposomes, suppositories, tablets, pills, or powders. In some embodiments, the compositions are in the form of injectable or infusible solutions. The composition can be in a form suitable for intravenous, intraarterial, intramuscular, subcutaneous, parenteral, transmucosal, oral, topical, or transdermal administration. The composition may be formulated as an immediate, controlled, extended or delayed release composition.

The compositions of the invention can be administered either as individual therapeutic agents or in combination with other therapeutic agents. They can be administered alone, but are generally administered with a pharmaceutical carrier selected on the basis of the chosen route of administration and standard pharmaceutical practice. Administration of the antibodies disclosed herein may be carried out by any suitable means, including parenteral injection (such as intraperitoneal, subcutaneous, or intramuscular injection), orally, or by topical administration of the antibodies (typically carried in a pharmaceutical formulation) to an airway surface. Topical administration to an airway surface can be carried out by intranasal administration (e.g., by use of dropper, swab, or inhaler). Topical administration of the antibodies to an airway surface can also be carried out by inhalation administration, such as by creating respirable particles of a pharmaceutical formulation (including both solid and liquid particles) containing the antibodies as an aerosol suspension, and then causing the subject to inhale the respirable particles. Methods and apparatus for administering respirable particles of pharmaceutical formulations are well known, and any conventional technique can be employed.

In some desired embodiments, the antibodies are administered by parenteral injection. For parenteral administration, antibodies or molecules can be formulated as a solution, suspension, emulsion or lyophilized powder in association with a pharmaceutically acceptable parenteral vehicle. For example, the vehicle may be a solution of the antibody or a cocktail thereof dissolved in an acceptable carrier, such as an aqueous carrier such vehicles are water, saline, Ringer's solution, dextrose solution, trehalose or sucrose solution, or 5% serum albumin, 0.4% saline, 0.3% glycine and the like. Liposomes and nonaqueous vehicles such as fixed oils can also be used. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody in these formulations can vary widely, for example from less than about 0.5%, usually at or at least about 1% to as much as 15% or 20% by weight and will be selected primarily based on fluid volumes, viscosities, etc., in accordance with the particular mode of administration selected. The vehicle or lyophilized powder can contain additives that maintain isotonicity (e.g., sodium chloride, mannitol) and chemical stability (e.g., buffers and preservatives). The formulation is sterilized by commonly used techniques. Actual methods for preparing parenterally administrable compositions will be known or apparent to those skilled in the art and are described in more detail in, for example, REMINGTON'S PHARMA. SCI. (15th ed., Mack Pub. Co., Easton, Pa., 1980).

The antibodies or molecules of the invention can be lyophilized for storage and reconstituted in a suitable carrier prior to use. This technique has been shown to be effective with conventional immune globulins. Any suitable lyophilization and reconstitution techniques can be employed. It will be appreciated by those skilled in the art that lyophilization and reconstitution can lead to varying degrees of antibody activity loss and that use levels may have to be adjusted to compensate. The compositions containing the present antibodies or a cocktail thereof can be administered for prevention of recurrence and/or therapeutic treatments for existing disease. Suitable pharmaceutical carriers are described in the most recent edition of REMINGTON'S PHARMACEUTICAL SCIENCES, a standard reference text in this field of art. In therapeutic application, compositions are administered to a subject already suffering from a disease, in an amount sufficient to cure or at least partially arrest or alleviate the disease and its complications.

Effective doses of the compositions of the present invention, for treatment of conditions or diseases as described herein vary depending upon many different factors, including, for example, but not limited to, the pharmacodynamic characteristics of the particular agent, and its mode and route of administration; target site; physiological state of the animal; other medications administered; whether treatment is prophylactic or therapeutic; age, health, and weight of the recipient; nature and extent of symptoms kind of concurrent treatment, frequency of treatment, and the effect desired.

Single or multiple administrations of the compositions can be carried out with dose levels and pattern being selected by the treating veterinarian. In any event, the pharmaceutical formulations should provide a quantity of the antibody(ies) of this invention sufficient to effectively treat the subject. In some embodiments, the composition is administered bimonthly, once-in-three months, once-in-four months, once-in-five months, once-in-six months, or once-in-seven months.

Treatment dosages may be titrated using routine methods known to those of skill in the art to optimize safety and efficacy.

The pharmaceutical compositions of the invention may include a "therapeutically effective amount." A "therapeutically effective amount" refers to an amount effective, at dosages and for periods of time necessary, to achieve the desired therapeutic result. A therapeutically effective amount of a molecule may vary according to factors such as the disease state, age, sex, and weight of the individual, and the ability of the molecule to elicit a desired response in the individual. A therapeutically effective amount is also one in which any toxic or detrimental effects of the molecule are outweighed by the therapeutically beneficial effects.

In another aspect, the compositions of the invention can be used, for example, in the treatment of various diseases and disorders in cats. As used herein, the terms "treat" and "treatment" refer to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. Those in need of treatment include those already with the disease or condition as well as those prone to having the disease or condition or those in which the disease or condition is to be prevented.

The composition having mutant molecule of the invention can be used to treat any suitable disease or disorder. For example, the mutant anti-IL31 antibody of the invention can be used to treat an IL-31-mediated pruritic or allergic condition. The examples of IL-31-mediated pruritic condition include, for example, but not limited to, atopic dermatitis, eczema, psoriasis, scleroderma, and pruritis. The examples of IL-31-mediated allergic condition include, for example, but not limited to, allergic dermatitis, summer eczema, urticaria, heaves, inflammatory airway disease, recurrent airway obstruction, airway hyper-responsiveness, chronic obstruction pulmonary disease, and inflammatory processes resulting from autoimmunity.

The mutant anti-NGF antibody of the invention can be used to treat an NGF-mediated pain or a condition. The examples of a pain include, for example, but not limited to, a chronic pain, an inflammatory pain, a post-operative incision pain, a neuropathic pain, a fracture pain, an osteoporotic fracture pain, a post-herpetic neuralgia, a cancer pain, a pain resulting from burns, a pain associated with wounds, a pain associated with trauma, a neuropathic pain, a pain associated with a musculoskeletal disorder, a rheumatoid arthritis, an osteoarthritis, an ankylosing spondylitis, a seronegative (non-rheumatoid) an arthropathies, a non-articular rheumatism, a periarticular disorder, or a peripheral neuropathy. In a particular embodiment, the pain is an osteoarthritis pain.

The mutant anti-TGFβ antibody of the invention can be used to treat a TGFβ-mediated disease or a condition. The examples of a TGFβ-mediated disease or a condition include, for example, but not limited to, a chronic kidney disease.

All patents and literature references cited in the present specification are hereby incorporated by reference in their entirety.

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

EXAMPLES

Example 1

Construction of Feline IgG Fc Mutants

Construction of all feline IgGs (FIG. 1) was carried out as described by Strietzel et. al. (Strietzel et al., 2014, *Vet Immunol Immunopathol., vol.* 158(3-4), pages 214-223), in which plasmids containing sequence encoding for feline constant regions for the IgG sub-class 1 Allele a (IgG1a) were utilized and VH/VL sequences for each mAb investigated herein were inserted upstream and in frame with the nucleotides encoding for the constant domains. Mutations were incorporated into position S434 and S428 of the CH3 domain (FIG. 2) of each plasmid using Agilent's QuikChange II Mutagenesis and associated Agilent primer design tools for single-site directed mutagenesis (https://www.agilent.com/store/primerDesignProgram.jsp).

Antibody constructs were transiently expressed either in HEK 293 cells using a standard lipofectarnine transfection protocol (Invitrogen Life Technologies, Carlsbad, CA, USA) or into CHO cells using the ExpiCHO transient system (ThermoFisher Scientific) kit protocols. ExpiCHO expression followed protocols outlined by ThermoFisher for a co-transfection of plasmid containing gene sequence encoding for an IgG light and an IgG heavy chain. For HEK293 expression, equal amounts by weight of heavy chain plasmid and light chain plasmid were co-transfected. Cells were allowed to grow for 7 days after which supernatants were collected for antibody purification. Antibodies were screened for binding to protein. A sensors via Octet QKe quantitation (Pall ForteBio Corp, Menlo Park, CA, USA). Constructs which bound to protein A were purified and quantified as described in Strietzel el al, for protein quality.

Example 2

Target Binding Affinity and Potency Assay

Affinity for each mAb was assessed by Biacore and the IC50 was determined via a suitable cell based potency assay. Surface Plasmon Resonance was performed on a Biacore T200 (GE Healthcare, Pittsburgh, PA) to measure binding affinities of each antibody to its target, 2.5 µg/ml of each target protein was immobilized by amine coupling using EDC/NHS for a final density ~250 RU (resonance unit) on CM5 sensor flow cells 2-4, respectively.

Flow cell 1 was used as an internal reference to correct running buffer effects. Antibody binding was measured at 15° C. with a contact time of 250 s and flow rate of 30111/min. The dissociation period was 300 s. Regeneration was performed with regeneration buffers (10 mM Glycine pH1.5 and 10 mM NaOH) and flow rate at 20111/min for 60 s each. Running/dilution buffer (1×HBS-EP, GE Healthcare, BR-1006-69, 10×-including 100 mM HEPES, 150 mM NaCl, 30 mM EDTA and 0.5% v/v surfactant P20, pH7.4, 1:10 in filtered MQ H2O) was used as negative control at the same assay format.

Data were analyzed with Biacore T200 Evaluation software by using the method of double referencing. The resulting curve was fitted with the 1:1 binding model. No differences in binding affinities or IC50 were observed between wild-type and S434 and S428 mutant IgGs (Table 1).

TABLE 1

Affinities and potencies of WT and S434 and S428 mutant IgGs.
No differences were measured between the WT and mutant IgGs:

| mAb | Wild-Type Affinity for target | IC50 | S434H Mutant Affinity for target | IC50 | S428L Mutant Affinity for target | IC50 |
|---|---|---|---|---|---|---|
| mAb1 | 2.23E-11 | ND | | | 2.28E-11 | ND |
| mAb2 | 2.30E-11 | 0.69 nM | | | 8.00E-12 | 0.58 nM |
| mAb3 | 5.82E-13 | 0.036 nM | 1.32E-12 | | | |
| mAb6 | 3.75E-12 | 9 nM | | | 8.43E-11 | 10 nM |

ND refers to not-determined.
mAb1 refers to felinized anti-IL31 antibody. Anti-IL31 antibody is well known in the art. See e.g., U.S. Pat. Nos. 10,526,405; 10,421,807; 9,206,253; 8,790,651. mAb2 and mAb3 refer to felinized anti-NGF antibodies. Anti-NGF antibody is also well known in the art. See e.g., U.S. Pat. Nos. 10,125,192; 10,093,725; 9,951,128; 9,617,334; and 9,505,829. mAb6 refers to felinized anti-TGFβ antibody. Anti-TGFβ antibody is also well known in the art. See e.g., U.S. Patent Applications 63/036,092 and 63/248,679.

Example 3

In Vitro FcRn Binding Assay

Feline FcRn was isolated, prepared and mutant Fc IgGs were assayed against feline FcRn according to Strietzelg et. al. Standard RACE PCR was used to amplify feline FcRn-α subunit and β-microglobulin. FcRn-α subunit and β-microglobulin were co-transfected into HEK 293 cells and the FcRn complex was purified by IMAC affinity purification via the c-terminal His tag. KD's were measured by Biacore 3000 or Biacore T200 (GE Healthcare, Pittsburgh, PA, USA) using a CM5 sensor chip.

FcRn was immobilized on the surface of the sensor using the standard amine immobilization method to reach the desired surface density. HBS-EP was used as the immobilization running buffer and 10 mM MES; 150 mM NaCl; 0.005% Tween20; 0.5 mg/mL BSA; pH6 and pH7.2 and PBS; 0.005% Tween20; 0.5 mg/mL BSA; pH7.4 were used for method running buffers and titrations. Fc mutant IgGs were flowed over receptor surfaces and affinity was determined using Scrubber2 software analysis (BioLogic Software Pty, Ltd., Campbell, Australia) or T200 evaluation software (Table 2). Blank runs containing buffer only were subtracted out from all runs. Flow cells were regenerated using 50 mM Tris pH8. Runs were performed at 15° C.

Mutations made at position 434 and 428 have a marked effect on the affinity of the IgG to FcRn at pH6. This study reveals that the increase in FcRn affinity for IgG is not dependent on the VHVL domains, and is universal for any feline IgG1a.

TABLE 2

Binding of wild-type (WT), N434 and S428 mutant IgGs to Feline FcRn measured by surface plasmon resonance (Biacore):

| mAb | Wild-Type FcRn pH 6 | Wild-Type FcRn pH 7.2 | S434H Mutant FcRn pH 6 | S434H Mutant FcRn pH 7.2 | S428L Mutant FcRn pH 6 | S428L Mutant FcRn pH 7.2 |
|---|---|---|---|---|---|---|
| mAb1 | 1.21E-08 | NBO | | | 3.77E-09 | 1.80E-07 |
| mAb2 | 2.50E-08 | 3.80E-07 | | | 1.51E-09 | 6.00E-08 |
| mAb3 | 2.95E-09 | 8.63E-06 | 1.02E-09 | 5.24E-10 | | |
| mAb6 | 1.20E-07 | NBO | | | 1.50E-08 | 2.30E-07 |

NBO refers to no binding observed.
mAb1 refers to felinized anti-IL31 antibody, as discussed in Table 1. mAb2 and mAb3 refer to felinized anti-NGF antibodies, as discussed in Table 1. mAb6 refers to felinized anti-TGFβ antibody, as discussed in Table 1.

TABLE 3

Binding of wild-type (WT) and N434 mutant IgGs to Feline FcRn measured by surface plasmon resonance (Biacore):

| | Wild-Type FcRn pH 6 | Wild-Type FcRn pH 7.2 | Mutant FcRn pH 6 | Mutant FcRn pH 7.2 |
|---|---|---|---|---|
| Wild-Type | 2.95E-09 | 8.63E-06 | | |
| S434A | | | 4.49E-09 | 4.59E-12 |
| S434C | | | 1.18E-08 | 2.91E-12 |
| S434D | | | 5.66E-09 | 5.34E-07 |
| S434E | | | 3.35E-09 | 1.25E-09 |
| S434F | | | 7.45E-10 | 2.10E-08 |
| S434G | | | 9.58E-09 | 2.16E-08 |
| S434I | | | 1.44E-08 | 1.81E-08 |
| S434K | | | 6.76E-09 | 5.06E-09 |
| S434L | | | 8.67E-09 | 6.57E-09 |
| S434M | | | 2.80E-09 | 1.92E-09 |
| S434N | | | 6.94E-09 | 8.47E-12 |
| S434P | | | 5.64E-09 | 1.57E-11 |
| S434Q | | | 4.80E-09 | 8.01E-11 |
| S434R | | | 1.19E-09 | 1.63E-08 |
| S434T | | | 1.06E-08 | 4.12E-12 |
| S434V | | | 3.71E-09 | 4.30E-12 |
| S434W | | | 7.71E-10 | 2.16E-08 |
| S434Y | | | 4.33E-10 | 1.44E-08 |

Anti-NGF antibody was used.

Example 4

Fc Mutant IgG PK Studies in Cats

Pharmacokinetic (PK) studies were conducted to show the effect of the half-life extension mutations S434H and S428L on a IgG1a subclass with mAbs raised against multiple targets. Study designs varied but essentially two types of studies were conducted:

Study design 1: The mAb was administered to groups of 4 male and 4 female domestic short hair cats at 2 mg/kg per dose. The first and second doses were administered subcutaneously 28 days apart. The third dose was administered intravenously 28 days later. Serum samples were collected weekly for 14 weeks.

Study design 2: The mAb was administered as a single dose of 2 mg/kg subcutaneously or intravenously to groups of 3 or 4 domestic short hair cats. Serum samples were collected weekly.

Pharmacokinetic calculations were performed using the noncompartmental approach (linear trapezoidal rule for AUC calculations) with the aid of Watson™. Additional calculations were performed with Excel™, including correction of the AUC for the overlap of the concentration-time profiles after the 2nd and 3rd injections of drug. Summaries of concentration-time data and pharmacokinetic data with simple statistics (mean, standard deviation, coefficient of variation) were calculated using Excel™ or Watson™. No other statistical analyses were conducted.

TABLE 4

| Calculated Half-Life's for wild-type and S428L and S434H mutant feline IgGs: | |
| --- | --- |
| IgG | Half-Life (days) |
| mAb1 WT | 11.3 |
| mAb1 S428L | 26 |
| mAb2 WT | 7.9 |
| mAb2 S428L | 23 |
| mAb3 WT | 10.1 |
| mAb3 S434H | 13.2 |
| mAb6 WT | 5.9 |
| mAb6 S428L | 15.5 | mAb1 refers to felinized anti-IL31 antibody. Anti-IL31 antibody is well known in the art. See e.g., U.S. Pat. Nos. 10,526,405; 10,421,807; 9,206,253; 8,790,651. mAb2 and mAb3 refer to felinized anti-NGF antibodies. Anti-NGF antibody is also well known in the art. See e.g., U.S. Pat. Nos. 10,125,192; 10,093,725; 9,951,128; 9,617,334; and 9,505,829. mAb6 refers to felinized anti-TGFβ antibody. Anti-TGFβ antibody is also well known in the art. See e.g., U.S. Patent Applications 63/036,092 and 63/248,679.

The feline IgG1a point mutation S428L has been shown to increase the half-life of three different feline IgGs by 2.5 to 3 fold in domestic short hair cats. For mAb1 the half-life increased from 11 days to 26 days, and for mAb2 from 7.9 days to 23 days, and for mAb4 from 5.9 days to days. The feline IgG1a point mutation S434H has been shown to increase the half-life of one mAb from 10.1 days to 13.2 days.

The mechanism of action is via enhancing affinity to feline FcRn at pH6 and it has been demonstrated with multiple feline IgGs, that bind very different and distinct soluble targets. Therefore, it has been demonstrated that the half-life extension of S428L and N434 mutations of feline IgG1a is independent of the VHVL domains.

Example 5

FcRn Binding Assay

Feline FcRn was isolated, prepared and mutant Fc IgGs were assayed against feline FcRn according to Strietzel et. al., discussed above. Standard PCR was used to amplify feline FcRn-α subunit and β-microglobulin. FcRn-α subunit and β-microglobulin were co-transfected into HEK 293 cells and the FcRn complex was purified by IMAC affinity purification via the c-terminal His tag. FcRn complex was biotin labeled through BirA enzymatic biotinylatoin reaction. KD's were measured by Biacore T200 (GE Healthcare, Pittsburgh, PA, USA) or Biacore 8K (Cytiva, Marlborough, MA, USA) using a SA sensor chip.

FcRn was captured on the surface of the sensor using a modified SA capture method. 10 mM MES; 150 mM NaCl; 0.005% Tween20; 0.5 mg/mL BSA; pH6 was used as capture, method running buffer and titrations. 1×HBS-P, 0.5 mg/mL BSA; pH7.4 was also used for method running buffer and titrations. Fc mutant IgGs were flowed over receptor surfaces and affinity was determined using T200 evaluation software or Biacore Insight Evaluation software. Blank runs containing buffer only were subtracted out from all runs. Flow cells were regenerated using 50 mM Tris pH8 or pH9. Runs were performed at 15° C.

Mutations made at respective positions have a marked effect on the affinity of the IgG to FcRn at pH6. Binding of wild-type (WTs) and mutant IgGs to feline FcRn were measured by surface plasmon resonance (Biacore).

The marked effect on the affinity was observed in completely different and structurally different antibodies that bind different targets (i.e., anti-IL31 and anti-NGF antibodies) and also different versions of antibodies that bind the same target (i.e., different versions of anti-IL31 and anti-NGF antibodies) (Tables 1-5). Therefore, the increase in FcRn affinity for IgG is not dependent on the VHVL domains or CDR regions. In addition, the marked effect on the affinity was observed in multiple IgG subclasses. Generally, the results show that the increase in FcRn affinity for IgG is independent of feline IgG subclass.

TABLE 5A

| | Binding of wild-type (WT) and S428 and S434 mutant IgGs to feline FcRn | | | | | | |
| --- | --- | --- | --- | --- | --- | --- | --- |
| | Feline | | mAb4 | | | mAb3 | |
| Mutations | IgG subclass | ID No. | KD pH 6 | KD pH 7.4 | ID No. | KD pH 6 | KD pH 7.4 |
| WT | IgG1a | 1 | 3.20E−08 | NBO | 88 | 2.60E−08 | NBO |
| S428A | IgG1a | 2 | 6.64E−08 | NBO | 89 | 2.23E−08 | NBO |
| S428C | IgG1a | 3 | 2.90E−08 | NBO | 90 | 2.62E−08 | NBO |
| S428D | IgG1a | 4 | 1.90E−07 | NBO | 91 | 5.68E−08 | NBO |
| S428E | IgG1a | 5 | 3.79E−08 | NBO | 92 | 5.74E−08 | NBO |
| S428F | IgG1a | 6 | 2.97E−08 | NBO | 93 | 6.75E−09 | NBO |
| S428G | IgG1a | 7 | NBO | NBO | 94 | 8.77E−08 | NBO |
| S428H | IgG1a | 8 | 2.55E−08 | NBO | 95 | 5.33E−08 | NBO |
| S428I | IgG1a | 9 | 1.67E−08 | NBO | 96 | 2.22E−08 | NBO |

TABLE 5A-continued

Binding of wild-type (WT) and S428 and S434 mutant IgGs to feline FcRn

| Mutations | IgG subclass | mAb4 | | | mAb3 | | |
|---|---|---|---|---|---|---|---|
| | | ID No. | KD pH 6 | KD pH 7.4 | ID No. | KD pH 6 | KD pH 7.4 |
| S428K | IgG1a | 10 | 2.14E-08 | NBO | 97 | 2.22E-08 | NBO |
| S428L | IgG1a | 11 | 1.55E-08 | NBO | 98 | 1.54E-08 | NBO |
| S428M | IgG1a | 12 | 1.88E-08 | NBO | 99 | 6.89E-09 | NBO |
| S428N | IgG1a | 13 | 4.90E-08 | NBO | 100 | 1.12E-08 | NBO |
| S428P | IgG1a | 14 | NBO | NBO | 101 | 1.78E-08 | NBO |
| S428Q | IgG1a | 15 | NBO | NBO | 102 | 7.13E-08 | NBO |
| S428R | IgG1a | 16 | NBO | NBO | 103 | 2.73E-08 | NBO |
| S428T | IgG1a | 17 | NBO | NBO | 104 | 2.58E-08 | NBO |
| S428V | IgG1a | 18 | 6.39E-08 | NBO | 105 | 1.71E-08 | NBO |
| S428W | IgG1a | 19 | NBO | NBO | 106 | 1.85E-08 | NBO |
| S428Y | IgG1a | 20 | 6.34E-08 | NBO | 107 | 5.82E-08 | NBO |
| S428L and S434H | IgG1a | 22 | 1.77E-08 | NBO | 109 | 1.31E-08 | NBO |
| S428L and S434F | IgG1a | 23 | 8.47E-08 | NBO | 110 | 3.38E-09 | 2.00E+07 |
| S428L and S434L | IgG1a | 24 | 9.72E-08 | NBO | 111 | 3.12E-10 | 2.04E+14 |
| S428L and S434P | IgG1a | 25 | 2.25E-06 | NBO | 112 | 1.88E-08 | NBO |
| S428L and S434W | IgG1a | 26 | 1.72E-08 | NBO | 113 | 2.36E-08 | NBO |
| S428Y and S434H | IgG1a | 27 | 1.88E-08 | NBO | 114 | 3.25E-09 | 1.17E+11 |
| S428Y and S434F | IgG1a | 28 | 1.89E-08 | NBO | 115 | 2.94E-09 | 3.62E+08 |
| S428Y and S434L | IgG1a | 29 | 4.40E-08 | NBO | 116 | 3.43E-08 | NBO |
| S428Y and S434P | IgG1a | 30 | 4.06E-08 | NBO | 117 | 1.66E-08 | NBO |
| S428Y and S434W | IgG1a | 31 | 7.80E-09 | 4.31E-07 | 118 | 8.12E-10 | 2.55E+06 |
| S428M and S434H | IgG1a | 32 | 1.72E-08 | NBO | | | |
| S428M and S434F | IgG1a | 33 | 4.29E-09 | 4.01E-06 | | | |
| S428M and S434L | IgG1a | 34 | 2.83E-08 | NBO | | | |
| S428M and S434P | IgG1a | 35 | 4.20E-08 | NBO | | | |
| S428M and S434W | IgG1a | 36 | 6.83E-09 | 5.01E-06 | | | |
| S428M and S434L | IgG1a | 49 | 1.86E-08 | NBO | 131 | 1.39E-08 | NBO |
| S428M and S434P | IgG1a | 50 | 3.98E-08 | NBO | 132 | 2.61E-08 | NBO |
| S434H | IgG1a | 00 | 4.88E-09 | NBO | 00 | 2.60E-09 | NBO |
| WT | IgG1b | 56 | 9.08E-08 | NBO | 138 | 2.91E-09 | NBO |
| S428L | IgG1b | 57 | 1.66E-08 | NBO | 139 | 8.44E-08 | NBO |
| S434H | IgG1b | 58 | 1.51E-08 | NBO | 140 | 9.85E-09 | NBO |
| WT | IgG2_hinge | 59 | 4.44E-08 | NBO | 141 | 2.79E-08 | NBO |
| S428L | IgG2_hinge | 60 | 2.45E-08 | NBO | 142 | 1.12E-08 | NBO |
| S428M | IgG2_hinge | 61 | 8.10E-08 | NBO | 143 | 1.51E-08 | NBO |
| S434H | IgG2_hinge | 62 | 2.55E-08 | NBO | 144 | 1.31E-08 | NBO |
| S434F | IgG2_hinge | 63 | 1.91E-08 | NBO | 145 | 4.04E-09 | 3.61E-05 |
| S428L and S434H | IgG2_hinge | 64 | 2.07E-08 | NBO | 146 | 2.45E-09 | 7.42E-06 |
| S428L and S434F | IgG2_hinge | 65 | 6.31E-09 | NBO | 147 | 3.48E-10 | 4.93E-08 |
| S428M and S434H | IgG2_hinge | 66 | 2.41E-08 | NBO | 148 | 6.67E-09 | 2.39E-05 |
| S428M and S434F | IgG2_hinge | 67 | 1.07E-08 | NBO | 149 | 1.43E-09 | 1.08E-07 | mAb4 and mAb3 refer to felinized anti-IL31 (ZTS-5864) and anti-NGF (ZTS-768) antibodies, respectively. mAb3 in this table and Tables 1, 2, and 4 above are the same (i.e., ZTS-768). However, mAb3 in this table has different VL, VH, and CDR regions, relative to mAb2 antibody listed in Tables 1, 2, and 4.
NBO = No binding Observed.

TABLE 5B

Binding of wild-type (WT) and S428 and S434 mutant IgGs to feline FcRn

| Mutations | IgG subclass | mAb4 | | | mAb5 | | |
|---|---|---|---|---|---|---|---|
| | | ID No. | KD pH 6 | KD pH 7.4 | ID No. | KD pH 6 | KD pH 7.4 |
| S428L | IgG1a | 11 | 1.55E-08 | NBO | 68 | 8.65E-09 | NBO |
| S428M and S434L | IgG1a | 49 | 1.86E-08 | NBO | 81 | 1.86E-08 | NBO |

TABLE 5B-continued

Binding of wild-type (WT) and S428 and S434 mutant IgGs to feline FcRn

| Mutations | IgG subclass | mAb4 | | | mAb5 | | |
|---|---|---|---|---|---|---|---|
| | | ID No. | KD pH 6 | KD pH 7.4 | ID No. | KD pH 6 | KD pH 7.4 |
| S428M and S434P | IgG1a | 50 | 3.98E-08 | NBO | 82 | 3.32E-08 | NBO | mAb4 and mAb5 refer to felinized anti-IL31 antibodies. mAb4 has different VL, VH, and CDR regions, relative to mAb5.
NBO = No binding Observed.

Example 6

FcRn Binding Assay

As discussed in the above Example section, Feline FcRn was isolated, prepared and mutant Fc IgGs were assayed against feline FcRn according to Strietzelg et. al. Standard RACE PCR was used to amplify feline FcRn-α subunit and β-microglobulin. FcRn-α subunit and β-microglobulin were co-transfected into HEK 293 cells and the FcRn complex was purified by IMAC affinity purification via the c-terminal His tag. KD's were measured by Biacore 3000 or Biacore T200 (GE Healthcare, Pittsburgh, PA, USA) using a CM5 sensor chip.

FcRn was captured on the surface of the sensor using a modified SA capture method. 10 mM MES; 150 mM NaCl;

0.005% Tween20; 0.5 mg/mL BSA; pH6 was used as capture, method running buffer and titrations. 1×HBS-P, 0.5 mg/mL BSA; pH7.4 was also used for method running buffer and titrations. Fc mutant IgGs were flowed over receptor surfaces and affinity was determined using T200 evaluation software or Biacore Insight Evaluation software. Blank runs containing buffer only were subtracted out from all runs. Flow cells were regenerated using 50 mM Tris pH8 or pH9. Runs were performed at 15° C.

Mutations made at position 434 and 428 have a marked effect on the affinity of the IgG to FcRn at pH6. This study reveals that the increase in FcRn affinity for IgG is not dependent on the VHVL domains.

TABLE 6a

Binding of wild-type (WT) and N434 mutant IgGs to feline FcRn measured by surface plasmon resonance (Biacore):

| WT/ Mutant | ID No. | Target 3 + mAb6 KD at pH 6 | KD at pH 7.4 | ID No. | Target 3 + mAb6 KD at pH 6 | KD at pH 7.4 | ID No. | Target 3 + mAb6 KD at pH 6 | KD at pH 7.4 | ID No. | Target 3 + mAb6 KD at pH 6 | KD at pH 7.4 | ID No. | Target 3 + mAb6 KD at pH 6 | KD at pH 7.4 |
|---|---|---|---|---|---|---|---|---|---|---|---|---|---|---|---|
| WT | 1 | 1.47E−07 | NBO | 12 | 3.52E−08 | NBO | 14 | 2.23E−08 | NBO | 16 | 2.05E−08 | NBO | 18 | 1.96E−08 | NBO |
| S434H | 2 | 2.21E−08 | NBO | 13 | 2.78E−09 | NBO | 15 | 2.10E−09 | 7.08E−07 | 17 | 2.16E−09 | 1.26E−07 | 19 | 2.05E−09 | NBO |

Feline IgG1a subclass B was used.

NBO = No binding Observed;

Nucleic acid codon for WT and S434H mutant is AGC and CAC, respectively.

ID numbers 1, 12, 14, 16, and 18 represent wildtype mAb6 anti-TGFβ antibodies ZTS-310, ZTS-120-1, ZTS-120-2, ZTS-120-3, and ZTS-120-4, respectively.
ID numbers 2, 13, 15, 17, and 19 represent mutant mAb6 anti-TGFβ antibodies ZTS-310, ZTS-120-1, ZTS-120-2, ZTS-120-3, and ZTS-120-4, respectively.

TABLE 6b

Binding of wild-type (WT) and N434 mutant IgGs to feline FcRn measured by surface plasmon resonance (Biacore):

| WT/ Mutant | ID No. | Target 3 + mAb6 KD at pH 6 | KD at pH 7.4 | ID No. | Target 3 + mAb6 KD at pH 6 | KD at pH 7.4 | ID No. | Target 3 + mAb6 KD at pH 6 | KD at pH 7.4 | ID No. | Target 3 + mAb6 KD at pH 6 | KD at pH 7.4 | ID No. | Target 3 + mAb6 KD at pH 6 | KD at pH 7.4 |
|---|---|---|---|---|---|---|---|---|---|---|---|---|---|---|---|
| WT | 20 | 3.16E−08 | NBO | 22 | 1.43E−08 | NBO | 24 | 3.02E−08 | NBO | 26 | 3.57E−08 | NBO | 28 | 4.43E−08 | NBO |
| S434H | 21 | 2.67E−09 | NBO | 23 | 2.02E−09 | NBO | 25 | 2.47E−09 | NBO | 27 | 2.45E−09 | NBO | 29 | 2.73E−09 | NBO |

Feline IgG1a subclass B was used.

NBO = No binding Observed;

Nucleic acid codon for WT and S434H mutant is AGC and CAC, respectively.

ID numbers 20, 22, 24, 26, and 28 represent wildtype mAb6 anti-TGFβ antibodies ZTS-120-5, ZTS-120-6, ZTS-120-7, ZTS-120-8, and ZTS-120-9, respectively.
ID numbers 21, 23, 25, 27, and 29 represent mutant mAb6 anti-TGFB antibodies ZTS-120-5, ZTS-120-6, ZTS-120-7, ZTS-120-8, and ZTS-120-9, respectively.

TABLE 6c

Binding of wild-type (WT) and N434 mutant IgGs to feline
FcRn measured by surface plasmon resonance (Biacore):

| Codon | # of mutations | | ID No. | Target 3 + mAb6 | |
|---|---|---|---|---|---|
| | 1 | 2 | | KD at pH 6 | KD at pH 7.4 |
| AGC | WT | | 1 | 1.47E–07 | NBO |
| CAC | S434H | | 2 | 2.21E–08 | NBO |
| TTC | S434F | | 3 | 6.13E–09 | NBO |
| TAC | S434Y | | 4 | 7.73E–09 | NBO |
| CTG | S434L | | 5 | 3.83E–05 | NBO |
| CCC | S434P | | 6 | 8.38E–07 | NBO |
| TGG | S434W | | 7 | 1.81E–08 | NBO |
| CAC/CTG | S434H | S428L | 8 | 9.13E–09 | NBO |
| TTC/CTG | S434F | S428L | 9 | 1.55E–09 | 4.07E–06 |

TABLE 6c-continued

Binding of wild-type (WT) and N434 mutant IgGs to feline
FcRn measured by surface plasmon resonance (Biacore):

| Codon | # of mutations | | ID No. | Target 3 + mAb6 | |
|---|---|---|---|---|---|
| | 1 | 2 | | KD at pH 6 | KD at pH 7.4 |
| CAC/ATG | S434H | S428M | 10 | 4.97E–09 | NBO |
| TTC/ATG | S434F | S428M | 11 | 1.10E–09 | 1.91E–07 |

Feline IgG1a subclass B was used.
NBO = No binding Observed.
ID numbers 1 represents wildtype anti-TGFβ antibodies ZTS-310.
ID numbers 2-11 represent mutant forms of anti-TGFβ antibodies ZTS-310.

Having described preferred embodiments of the invention, it is to be understood that the invention is not limited to the precise embodiments, and that various changes and modifications may be effected therein by those skilled in the art without departing from the scope or spirit of the invention as defined in the appended claims.

What is claimed is:

1. A modified IgG comprising:

a feline IgG constant domain comprising at least one amino acid substitution relative to a wild-type feline IgG constant domain, wherein said substitution is at amino acid residue 434, numbered according to the EU index as in Kabat, wherein said substitution is a substitution of serine at position 434 with histidine (S434H), wherein said IgG is an anti-TGFβ molecule, and wherein the anti-TGFβ molecule comprises a variable heavy (VH) chain having the amino acid sequence set forth in SEQ ID NO.: 45, 55, 65, 75, 85, 95, 105, 115, 125, or 135 and a variable light (VL) chain having the amino acid sequence set forth in SEQ ID NO.: 47, 57, 67, 77, 87, 97, 107, 117, 127, or 137.

2. The modified IgG of claim 1, wherein said feline IgG constant domain comprises another substitution, wherein said another substitution is at amino acid residue 428.

3. The modified IgG of claim 2, wherein said another substitution is a substitution of serine at position 428 with leucine (S428L).

4. The modified IgG of claim 1, wherein the modified IgG has a higher affinity for FcRn than an IgG having the wild-type feline IgG constant domain.

5. The modified IgG of claim 1, wherein the modified IgG has a higher half-life than an IgG having the wild-type feline IgG constant domain.

6. The modified IgG of claim 1, wherein the modified IgG comprises an Fc constant region having CH2 or CH3 domain, or a combination thereof.

7. The modified IgG of claim 1, wherein the wild-type feline IgG constant domain comprises the amino acid sequence set forth in SEQ ID NO.: 3.

8. A pharmaceutical composition comprising the modified IgG of claim 1 and a pharmaceutically acceptable carrier.

9. A kit comprising the modified IgG of claim 1, in a container, and instructions for use.

10. A fusion molecule comprising the modified IgG of claim 1.

11. A method for increasing the serum half-life of a feline IgG molecule in a cat, the method comprising: administering said cat a composition comprising a modified IgG, said modified IgG comprising a feline IgG constant domain, said feline IgG constant domain comprising at least one amino acid substitution relative to a wild-type feline IgG constant domain, wherein said substitution is at amino acid residue 434, numbered according to the EU index as in Kabat, wherein said substitution is a substitution of serine at position 434 with histidine (S434H), wherein said IgG is an anti-TGFβ molecule, and wherein the anti-TGFβ molecule comprises a variable heavy (VH) chain having the amino acid sequence set forth in SEQ ID NO.: 45, 55, 65, 75, 85, 95, 105, 115, 125, or 135 and a variable light (VL) chain having the amino acid sequence set forth in SEQ ID NO.: 47, 57, 67, 77, 87, 97, 107, 117, 127, or 137.

12. The method of claim 11, wherein said feline IgG constant domain further comprising a substitution at amino acid residue 428, numbered according to the EU index as in Kabat.

13. The method of claim 12, wherein said substitution is a substitution of serine at position 428 with leucine (S428L).

14. The method of claim 11, wherein the modified IgG comprises an Fc constant region having CH2 or CH3 domain, or a combination thereof.

15. The method of claim 11, wherein the wild-type feline IgG constant domain comprises the amino acid sequence set forth in SEQ ID NO.: 3.

* * * * *